US008518646B2

(12) United States Patent  (10) Patent No.: US 8,518,646 B2
Jean et al.  (45) Date of Patent: Aug. 27, 2013

(54) **DETECTION OF *STAPHYLOCOCCUS AUREUS* AND IDENTIFICATION OF METHICILLIN-RESISTANT *STAPHYLOCOCCUS AUREUS***

(75) Inventors: Véronique Jean, Lac Beauport (CA); Mélanie Guillot, Québec (CA); Frank Courjal, Québec (CA); Chantal Savoye, Québec (CA)

(73) Assignee: Geneohm Sciences, Inc., Franklin Lakes, NJ (US)

( * ) Notice: Subject to any disclaimer, the term of this patent is extended or adjusted under 35 U.S.C. 154(b) by 1107 days.

(21) Appl. No.: 11/959,337

(22) Filed: Dec. 18, 2007

(65) Prior Publication Data

US 2011/0151452 A1  Jun. 23, 2011

Related U.S. Application Data

(60) Provisional application No. 60/870,823, filed on Dec. 19, 2006.

(51) Int. Cl.
*C12Q 1/68* (2006.01)
*C12P 19/34* (2006.01)
*C07H 21/04* (2006.01)

(52) U.S. Cl.
USPC .... 435/6.12; 435/91.2; 536/24.32; 536/24.33

(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 5,272,236 | A | 12/1993 | Lai et al. |
| 5,437,978 | A | 8/1995 | Ubukata et al. |
| 5,496,706 | A | 3/1996 | Kuusela et al. |
| 5,702,895 | A | 12/1997 | Matsunaga et al. |
| 5,776,712 | A | 7/1998 | Kuusela et al. |
| 5,780,610 | A | 7/1998 | Collins et al. |
| 5,783,638 | A | 7/1998 | Lai et al. |
| 5,866,366 | A | 2/1999 | Kallender |
| 6,083,587 | A | 7/2000 | Smith et al. |
| 6,090,592 | A | 7/2000 | Adams et al. |
| 6,117,635 | A | 9/2000 | Nazarenko et al. |
| 6,117,986 | A | 9/2000 | Nardone et al. |
| 6,156,507 | A | 12/2000 | Hiramatsu et al. |
| 6,271,351 | B1 | 8/2001 | Gawryl et al. |
| 6,380,370 | B1 | 4/2002 | Doucette-Stamm et al. |
| 7,449,289 | B2 * | 11/2008 | Huletsky et al. ............. 435/6.15 |
| 7,838,221 | B2 | 11/2010 | Huletsky et al. |
| 8,017,337 | B2 | 9/2011 | Paitan |
| 8,362,228 | B2 | 1/2013 | Paitan |
| 2005/0019893 | A1 | 1/2005 | Huletsky et al. |
| 2006/0252078 | A1 | 11/2006 | Huletsky et al. |
| 2007/0082340 | A1 | 4/2007 | Huletsky et al. |
| 2008/0227087 | A1 | 9/2008 | Huletski et al. |

FOREIGN PATENT DOCUMENTS

| | | |
|---|---|---|
| CA | 2348042 A1 | 12/2002 |
| EP | 0 527 628 | 2/1993 |
| EP | 0 543 942 A1 | 6/1993 |
| EP | 0 887 424 A2 | 12/1998 |
| EP | 1 529 847 A | 5/2005 |
| EP | 1 397 510 B1 | 11/2009 |
| EP | 2 322 655 A1 | 5/2011 |
| EP | 2 322 661 A1 | 5/2011 |
| EP | 2 322 663 A1 | 5/2011 |
| EP | 2 322 664 A1 | 5/2011 |
| EP | 2 322 930 A2 | 5/2011 |
| EP | 2 325 643 A2 | 5/2011 |
| EP | 2 325 644 A2 | 5/2011 |
| EP | 2 325 645 A2 | 5/2011 |
| EP | 2 325 646 A2 | 5/2011 |
| EP | 2 325 647 A2 | 5/2011 |
| JP | 11056371 | 3/1999 |
| WO | WO 92/02638 | 2/1992 |
| WO | WO 92/05281 | 4/1992 |
| WO | WO 95/13395 | 5/1995 |
| WO | WO 97/31125 | 8/1997 |
| WO | WO 01/23604 A2 | 4/2001 |
| WO | WO 02/099034 A2 | 12/2002 |
| WO | WO 2005/014857 | 2/2005 |
| WO | WO 2006/111028 | 10/2006 |
| WO | WO 2007/044873 | 4/2007 |
| WO | WO 2007/130951 A2 | 11/2007 |

OTHER PUBLICATIONS

Fang, H. et al. Rapid screening and identification of methicillin-resistant *Staphylococcus aureus* from clinical samples by selective-broth and real-time PCR assay. J Clin Microbiol., vol. 41, No. 7, pp. 2894-2899, 2003.*
Ralser, M et al. An efficient and economic enhancer mix for PCR. BBRC, vol. 347, pp. 747-751, Jul. 2006.*
Spiess, ANL. et al. Trehalose is a potent PCR enhancer: lowering of DNA melting temperature and thermal stabilization of Taq polymerase by the disaccharide trehalose. Clin Chem., vol. 50, No. 7, pp. 1256-1259, 2004.*
Archer, et al. "Origin and evolution of DNA associated with resistance to methicillin in staphylococci." Trends in Microbiology. 2(10):343-347 (1994).
Archer, et al. "Dissemination among staphylococci of DNA sequences associated with methicillin resistance." Antimicrobial Agents and Chemotherapy. 38(3):447-54 (1994).
Baba, et al. "Genome and virulence determinants of high virulence community-acquired MRSA." Lancet. 359: 1819-1827 (2002).
Barberis-Maino. IS431, a staphylococcal insertion sequence-like element related to IS26 from *Proteus vulgaris*. Gene. 59:107-13 (1983).
Berger-Bächi, et al. "Insertional inactivation of staphylococcal methicillin resistance by Tn551." J. Bacter. 154(1):479-87 (1983).
Buck, et al. "Design strategies and performance of custom DNA sequencing primers." Biotechniques, 27(3): 528-536, (Sep. 1999).

(Continued)

*Primary Examiner* — Prabha Chunduru

(74) *Attorney, Agent, or Firm* — Knobbe Martens Olson & Bear LLP

(57) ABSTRACT

Aspects of the present invention relate to methods and compositions for the detection and/or quantification of *S. aureus* from a sample, as well as methods and compositions useful for the detection and/or quantification of *S. aureus* and MRSA in a single assay. Embodiments include nucleic acids that hybridize to *S. aureus*-specific nuc sequences and MREJ sequences.

21 Claims, 4 Drawing Sheets

(56) References Cited

OTHER PUBLICATIONS

De Lencastre, et al. Methicillin-resistant *Staphylococcus aureus* disease in a Portuguese Hospital: Characterization of clonal types by a combination of DNA typing methods. Eur. J. Clin. Microbiol. Infect. Dis. 13(1): 64-73 (1994).

Deplano, et al. "In Vivo deletion of the methicillin resistance *mec* region from the chromosome of *Staphylococcus aureus* strains." J. Antimicrob. Chemother., 46-617-619 (2000).

Derbise, et al. "Mapping the regions carrying the three contiguous antibiotic resistance genes aadE, sat4, and aphA-3 in the genomes of staphylococci." Antimicro. Agen. Chemother. 41(5): 1024-32 (1997).

Dubin, et al. "Physical mapping of the *mec* region of an American methicillin-resistant *Staphylococcus aureus* strain." Antimicrob. Agents Chemother. 35(8):1661-65 (1991).

Egholm,et al. "PNA hybridizes to complementary oligonucleotides obeying the Watson-Crick hydrogen-bonding rules." Nature. 365: 566-568 (1993).

Flores, et. al. "A rapid, inexpensive method for eluting DNA from Agarose or Acrylamide gel slices without using toxic or chaotropic materials." Biotechniques. 13(2): 205-206 (1992).

Gerberding, et al. Comparison of conventional susceptibility tests with direct detection of penicillin-binding protein 2a in borderline oxacillin-resistant strains of *Staphylococcus aureus*. Antimicrob. Agents Chemother. 35(12):2574-79 (1991).

Hiramatsu, et al. "Molecular cloning and nucleotide sequence determination of the regulator region of *mecA* gene in methicillin-resistant *Staphylococcus aureus*." FEBS. 298(2.3):133-36 (1992).

Hiramatsu, et al. "The emergence and evolution of methicillin-resistant *Staphylococcus aureus*." Trends in Microbiology. 9(10): 486-493 (2001).

Hiramatsu et al. "*Staphylococcus aureus* DNA, type-IV.1." GenBank accession No. AB063172, version AB063172.2, Jun. 12, 2001.

Holden et al. "*Staphylococcus aureus* subsp. Aureus strain MRSA252, complete genome." GenBank accession No. BX571856, version BX571856.1, Jun. 23, 2004.

Holden, et al. "Complete genomes of two clinical *Staphylococcus aureus* strains: Evidence for the rapid evolution of virulence and drug resistance." PNAS. 101(26):9786-9791 (2004).

Inglis, et al. "Induced deletions within a cluster of resistance genes in the mec region of the chromosome of *Staphylococcus aureus*." Gen. Microbiol. 136(11):2231-2239 (1990).

Inglis, et al. "Methicillin-sensitive and -resistant homologues of *Staphylococcus aureus* occur together among clinical isolates." J. Infect. Dis. 167(2):323-328 (1993).

Ito, et al. "Acquisition of methicillin resistance and progression of multiantibiotic resistance in methicillin-resistant *Staphylococcus aureus*." Yonsei Med. J. 39(6):526-33 (1998).

Ito et al. GenBank accession No. AB014440, version AB014440.1, Jul. 6, 1999.

Ito et al. "*Staphylococcus aureus* DNA, 3' flanking region of mecDNA, strain 61/6219." accession No. AB014433, Jan. 7, 2000—Abstract only.

Ito et al. "*Staphylococcus aureus* DNA, type III staphylococcal cassette chromosome *mec*, strain 85/2082." GenBank accession No. AB037671, version AB037671.1, May 14, 2001.

Ito et al. GenBank accession No. AB121219, version AB121219.1, Sep. 26, 2003.

Kellogg, et al. "TaqStart Antibody™: "Hot Start" PCR facilitated by a neutralizing monoclonal antibody directed against Taq DNA Polymerase." Biotechniques. 16:1134-1137 (1994).

Kimmerly et al. "Staphylococcus epidermidis strains SR1 clone step. 1043h05 genomic sequence." GenBank accession No. AF270046, version AF270046.1, Aug. 1, 2000.

Kitagawa, et al. "Rapid diagnosis of methicillin-resistant *Staphylococcus aureus* bacteremia by nested polymerase chain reaction." Annals of Surgery. 224(5):665-71 (1996).

Kluytmans, et al. "Food-initiated outbreak of methicillin-resistant *Staphylococcus aureus* analyzed by Pheno- and Genotyping." J. Clin. Microbio. 33(5):1121-28 (1995).

Koshkin, et al. "LNA (locked nucleic acids): Synthesis of the adenine, cytosine, guanine, 5-methylcytosine, thymine and uracil bicyclonucleoside monomers, oligomerisation, and unprecedented nucleic acid recognition." Tetrahedron. 54:3607-3630 (1998).

Kuroda, et al. "Whole genome sequencing of meticillin-resistant *Staphylococcus aureus*." The Lancet. 357: 1225-1240 (2001).

Lawrence et al. "Consecutive isolation of homologous strains of methicillin-resistant and methicillin-susceptible *Staphylococcus aureus* from a hospitalized child." J. Hosp. Infect. 33:49-53 (1996).

Lawrence, et al. "Use of the coagulase gene typing method for detection of carriers of methicillin-resistant *Staphylococcus aureus*." J. Antimicro. Chemo. 37:687-96 (1996).

Lin, et al. "Sequence analysis and molecular characterization of genes required for the biosynthesis of type 1 capsular polysaccharide in *Staphylococcus aureus*." J. Bacter. 176(22):7005-16 (1994).

Lin et al. "*Staphylococcus aureus* M type 1 capsular polysaccharide biosynthesis gene cluster, complete sequence and unknown genes." GenBank accession No. U10927, version U10927.2, Nov. 1, 2001.

Luchansky et al. "Isolation of transposon Tn551 insertions near chromosomal markers of interest in *Staphylococcus aureus*." J. Bacter. 159(3):894-99 (1984).

Luijendijk, et al. "Comparison of five tests for identification of *Staphylococcus aureus* clinical samples." J. Clin. Microbio. 34(9):2267-69 (1996).

Luong, et al. "Type I capsule genes of *Staphylococcus aureus* are carried in a staphyloccal cassette chromosome genetic element." J Bacter. 184(13):3623-3629 (2002).

Martineau, et. al. "Correlation between the resistance genotype determined by multiplex PCR assays and the antibiotic susceptibility patterns of *Staphylococcus aureus* and *Staphylococcus epidermidis*." Antimicrob. Chemotherapy. 44(2): 231-238 (2000).

Mongkolrattanothai et al. "TPA exp: *Staphylococcus epidermidis* ATCC 12228 composite island SCCpbp4 region." GenBank accession No. BK001539, version BK001539.1, Aug. 15, 2003.

Mulligan, et al. "Methicillin-resistant *Staphylococcus aureus*: A consensus review of the microbiology, pathogenesis, and epidemiology with implications for prevention and management." Am J Med. 94(3):313-28 (1993).

Muraki, et al. Detection of methicillin-resistant *Staphylococcus aureus* using PCR and non-radioactive DNA probes (II). Rinsho Byori. 41(10): 1159-66 (1993).

Nichols, et al. "A universal nucleoside for use at ambiguous sites in DNA primers." Nature. 369:492-493 (1994).

Oliveira et al. "Genetic organization of the downstream region of the *mecA* element in methicillin-resistant *Staphylococcus aureus* isolates carrying different polymorphisms of this region." Antimicrob. Agents Chemother. 44(7):1906-1910 (2000).

Oliveira, et al. "Multiplex PCR strategy for rapid identification of structural types and variants of the *mec* element in methicillin-resistant *Staphylococcus aureus*." Antimicrob. Agents Chemother. 46:2155-2161 (2002).

Oliveira et al. "*Staphylococcus aureus* staphylococcal cassette chromosome *mec* type III sequence; and putative transposase gene, partial cds." GenBank Accession Version No. AF422691, Apr. 29, 2002, pp. 2. (Abstract Only).

Oliveira et al. "*Staphylococcus aureus* strain HDG2 genomic sequence downstream of *mecA*." GenBank Accession Version No. AF411934, Mar. 5, 2002, pp. 2. (Abstract Only).

Pattee, et al. "Genetic and physical mapping of the chromosome of *Staphylococcus aureus*." Molecular Biology of the Staphylococci. VCH Publishers.pp. 41-58 (1990).

Piccirilli et al. "Enzymatic incorporation of a new base pair into DNA and RNA extends the genetic alphabet." Nature. 343:33-37 (1990).

Simor, et al. "Characterization and proposed nomenclature of epidemic strains of methicillin-resistant *Staphylococcus aureus* in Canada." CCDR 25(12):105-112 (1999).

Stewart, et al. "IS257 and small plasmid insertions in the *mec* region of the chromosome of *Staphylococcus aureus*." Plasmid. 31:12-20 (1994).

Suzuki, et al. "Survey of methicillin-resistant clinical strains of coagulase-negative Staphylococci for *mecA* gene distribution." Antimicrob. Agents Chemother. 36(2): 429-434 (1992).

Suzuki, et al. "Distribution of *mec* regulator genes in methicillin-resistant *Staphylococcus* clinical strains." Antimicro. Agents Chemother.. 37(6):1219-26 (1993).
Taylor et al. GenBank accession No. AF270046, version AF270046.1, May 22, 2000.
Tokue, et al. "Comparison of a polymerase chain reaction assay and a conventional microbiologic method for detection of methicillin-resistant *Staphylococcus aureus*." Antimicro. Agents Chemother. 36(1):6-9 (1992).
Ubukata, et al. "Restriction maps of the regions coding for methicillin and tobramycin resistances on chromosomal DNA in methicillin-resistant Staphylococci." Antimicrob. Agents Chemother. 33(9):1624-26 (1989).
Ünal, et al. "Detection of methicillin-resistant Staphylococci by using the polymerase chain reaction." J Clin. Microbiol. 30(7):1685-91 (1992).
Ünal, et al. "Comparison of tests for detection of methicillin-resistant *Staphylococci aureus* in a clinical microbiology laboratory." Antimicrob. Agents Chemother. 38(2):345-47 (1994).
Van Belkum, et al. "Comparison of phage typing and DNA fingerprinting by polymerase chain reaction of discrimination of methicillin-resistant *Staphylococcus aureus* strains." J. Clin. Microbiol. 31(4):798-803 (1993).
Wada, et al. "Southern hybridization analysis of the *mecA* deletion from methicillin-resistant *Staphylococcus aureus*." Biochem. Biophys. Res. Comm., 176(3):1319-1326 (1991).
Wallet, et al. "Choice of a routine method for detecting methicillin-resistance in staphylococci." J. Antimicrob. Chemother. 37:901-909 (1996).
Westin, et al. "Anchored multiplex amplification on a microelectronic chip array." Nat. Biotechnol. 18:199-204 (2000).
Wu, et al. "Genetic organization of the *mecA* region in methicillin-susceptible and methicillin-resistant strains of *Staphylococcus sciuri*." J. Bacter. 180(2):236-42 (1998).
Xue, et al. "*Staphylococcus aureus* DNA, type-V staphylococcal cassette chromosome mec: strain JCSC3624." GenBank accession No. AB121219, Jan. 7, 2000—Abstract only.
Zhang, et al. "Genome-based analysis of virulence genes in a non-biofilm-forming *Staphylococcus epidermidis* strain (ATCC 12228)." Molecular Microbiology. 49(6): 1577-1593 (2003).
Partial International Search Report for International Application No. PCT/CA 02/00824 dated Jun. 4, 2002.
International Search Report dated Sep. 24, 2003 for International Patent Application No. PCT/CA02/000824, filed Jun. 4, 2002.
International Search Report and Written Opinion dated Nov. 23, 2007 for International Patent Application No. PCT/US06/39996, filed Oct. 10, 2006.
International Preliminary Report on Patentability (Rule 44*bis*)dated Apr. 16, 2008 for International Patent Application No. PCT/US06/39996, filed Oct. 10, 2006.
Supplementary European Search Report dated Apr. 7, 2009 for European Application No. 06825875.5.
International Preliminary Report on Patentability and Written Opinion dated Jul. 2, 2009 for International Application No. PCT/US072/088004, filed Dec. 18, 2007.
European Search Report dated Dec. 3, 2009 for European Application No. 07874372.1, filed Dec. 18, 2007.
Al-Soud et al., "Capacity of nine thermostable DNA polymerases to mediate DNA amplification in the presence of PCR-inhibiting samples", *Appl. Environ. Microbiol* (1998) 64(10):3748-53.
Al-Soud et al., "Effects of amplification facilitators on diagnostic PCR in the presence of blood, feces, and meat", *J. Clin. Microbiol.* (2000) 38(12):4463-70.
Arnheim et al., "Polymerase Chain Reaction", *C&EN* (1990) 36-47.
Ausubel et al., *Current Protocols in Molecular Biology*, 3rd Ed. Wiley Interscience Publishers (1995) [Table of Contents Only].
Barringer et al., "Blunt-end and single-strand ligations by *Escherichia coli* ligase: influence on an in vitro amplification scheme", *Gene* (1990) 89:117-122.
Bastos et al., "Molecular characterization and transfer among Staphylococcus strains of a plasmid conferring high-level resistance to mupirocin", *Eur. J. Clin. Microbiol. Infect. Dis.* (1999) 18(6):393-8.

Becker et al., "Thermonuclease gene as a target for specific identification of *Staphylococcus intermedius* isolates: use of a PCR-DNA enzyme immunoassay", *Diagn. Microbiol. Infect. Dis.* (2005) 51(4):237-44.
Brakstad et al., "Detection of *Staphylococcus aureus* by polymerase chain reaction amplification of the nuc gene", *J. Clin. Microbiol.* (1992) 30(7):1654-60.
Brakstad et al., "Comparison of tests designed to identify *Staphylococcus aureus* thermostable nuclease", *APMIS* (1995) 103(3):219-24.
Chakrabarti et al., "Novel sulfoxides facilitate GC-rich template amplification", *Biotechniques* (2002) 32(4):866, 868-874.
Chesneau et al., "Thermonuclease gene as a target nucleotide sequence for specific recognition of *Staphylococcus aureus*", *Mol. Cell. Probes.* (1993) 7(4):301-10.
Chongtrakool et al., "Staphylococcal cassette chromosome *mec* (SCC*mec*) typing of methicillin-resistant *Staphylococcus aureus* strains isolated in 11 Asian countries: a proposal for a new nomenclature for SCC*mec* elements", *Antimicrob. Agents Chemother.* (2006) 50(3):1001-12.
Costa et al., "Rapid detection of *mec*A and *nuc* genes in Staphylococci by real-time multiplex polymerase chain reaction", *Diagn. Microbiol. Infect. Dis.* (2005) 51(1):13-17.
Database Geneseq [Online]. "Polymorphic right extremity junction (MREJ) DNA #1." EBI accession No. GSN:ACD02065; Database accession No. ACD02065 (2003).
Elghanian et al., "Selective colorimetric detection of polynucleotides based on the distance-dependent optical properties of gold nanoparticles", *Science* (1997) 277(5329):1078-81.
Grisold et al., "Use of hybridization probes in a real-time PCR assay on the LightCycler® for the detection of methicillin-resistant *Staphylococcus aureus*", *Methods Mol. Biol.* (2006) 345:79-89.
Guatelli et al., "Isothermal, in vitro amplification of nucleic acids by a multienzyme reaction modeled after retroviral replication", *Proc. Natl. Acad. Sci. USA* (1990) 87(5):1874-8.
Hagen et al., "Development of a real-time PCR assay for rapid identification of methicillin-resistant *Staphylococcus aureus* from clinical samples", *Int. J. Med. Microbiol.* (2005) 295(2):77-86.
Hiramatsu et al., "Analysis of borderline-resistant strains of methicillin-resistant *Staphylococcus aureus* using polymerase chain reaction", *Microbiol. Immunol.* (1992) 36(5):445-53.
Hiramatsu et al., "Genetic basis for molecular epidemiology of MRSA", *J. Infect. Chemother.* (1996) 2:117-219.
Hjelmevoll et al. "The SYBR-MRSA PCR: A multiplex verification method for methicillin resistant *Staphylococcus aureus*." Abstracts of the General Meeting of the American Society for Microbiology. 103:C-083 URL (2003).
Huletsky et al., "New real-time PCR assay for rapid detection of methicillin-resistant *Staphylococcus aureus* directly from specimens containing a mixture of Staphylococci", *J. Clin. Microbiol.* (2004) 42(5):1875-84.
Innis et al Eds. PCR Protocols, A Guide to Methods and Applications, Academic Press (1990) Table of Contents.
Ito et al., "Cloning and nucleotide sequence determination of the entire mec DNA of pre-methicillin-resistant *Staphylococcus aureus* N315", *Antimicrob. Agents. Chemother.* (1999) 43(6):1449-58.
Ito et al., "Structural comparison of three types of staphylococcal cassette chromosome mec integrated in the chromosome in methicillin-resistant *Staphylococcus aureus*", *Antimicrob. Agents. Chemother.* (2001) 45(5):1323-36.
Ito et al., "Novel type V staphylococcal cassette chromosome mec driven by a novel cassette chromosome recombinase, ccrC", *Antimicrob. Agents Chemother.* (2004) 48(7):2637-51.
Kang et al., "The enhancement of PCR amplification of a random sequence DNA library by DMSO and betaine: application to in vitro combinatorial selection of aptamers", *J Biochem Biophys Methods.* (2005) 64(2):147-51.
Katayama et al., "A new class of genetic element, staphylococcus cassette chromosome mec, encodes methicillin resistance in *Staphylococcus aureus*", *Antimicrob. Agents Chemother.* (2000) 44(6):1549-55.

Kearns, et al. "Rapid detection of methicillin-resistant staphylococci by multiplex PCR." Journal of Hospital Infection. 43(1):33-37 (1999).

Kimmel et al., "Preparation of cDNA and the generation of cDNA libraries: overview", *Methods Enzymol.* (1987) 152:307-16.

Kloos et al., "Updated on clinical significance of coagulase-negative staphylococci", *Clin. Microbiol. Rev.* (1994) 7(1):117-40.

Kovacevic et al., "Secretion of staphylococcal nuclease by *Bacillus subtilis*", *J. Bacteriol.* (1985), 162(2):521-8.

Kwoh et al., "Transcription-based amplification system and detection of amplified human immunodeficiency virus type 1 with a bread-based sandwich hybridization format", *Proc. Natl. Acad. Sci. USA* (1989) 86(4):1173-7.

Landegren, "A ligase-mediated gene detection technique", *Science* (1988) 241(4869):1077-80.

Leach et al., "Theoretical investigations of novel nucleic acid bases", *J. Am. Chem. Soc.* (1992) 114:3675-3683.

Levi et al., "Detection of methicillin-resistant *Staphylococcus aureus* (MRSA) in blood with the EVIGENE MRSA detection kit", *J. Clin. Microbiol.* (2003) 41(8):3890-2.

Lomell et al., "Quantitative assays based on the use of replicatable hybridization probes", *J. Clin. Chem.* (1989) 35:1826-1831.

Ma et al., "Novel type of staphylococcal cassette chromosome mec identified in community-acquired methicillin-resistant *Staphylococcus aureus* strains", *Antimicrob. Agents Chemother.* (2002) 46(4):1147-52.

Maes et al., "Evaluation of a triplex PCR assay to discriminate staphylococcus aureus from coagulase-negative Staphylococci and determine methicillin resistance from blood cultures", *J. Clin. Microbiol.* (2002) 40(4):1514-7.

Mantsch et al., "Structural and enzymatic properties of adenine 1-oxide nucleotides", *Biochemistry* (1975) 14(26):5593-601.

McDonald et al., "Development of a triplex real-time PCR assay for detection of Panton-Valentine leukocidin toxin genes in clinical isolates of methicillin-resistant *Staphylococcus aureus*", *J. Clin. Microbiol.* (2005) 43(12):6147-9.

Murakami et al., "Identification of methicillin-resistant strains of staphylococci by polymerase chain reaction", *J. Clin. Microbiol.* (1991) 29(10):2240-4.

Murray et al., *Manual of Clinical Microbiology*, 8th Ed., ASM Press (2003) [Content pages only].

Newton et al., "Instrumentation, reagents and consumables", *PCR*, 2nd Ed., Springer-Verlag (2004), pp. 13.

Oliveira et al., "The evolution of pandemic clones of methicillin-resistant *Staphylococcus aureus*: identification of two ancestral genetic backgrounds and the associated mec elements", *Microb. Drug Resist.* (2001) 7(4):349-61.

Oliveira et al., "Secrets of success of a human pathogen: molecular evolution of pandemic clones of meticillin-resistant *Staphylococcus aureus*", *Lancet Infect. Dis.* (2002) 2(3):180-9.

Oliveira et al., "Redefining a structural variant of staphylococcal cassette chromosome mec, SCCmec type VI", *Antimicrob. Agents Chemother.* (2006) 50(10):3457-9.

*PCR Methods and Applications*, Cold Spring Harbor Laboratory Press (from 1991 to 1995), Contents pages only.

*PCR Strategies*, Academic Press, Inc. (1995), Contents pages only.

Persing et al., *Diagnostic Molecular Microbiology: Principles and Applications*, American Society for Microbiology, Washington, D.C. (1993), Contents pages only.

Piccirilli et al., "Enzymatic incorporation of a new base pair into DNA and RNA extends the genetic alphabet", (1990) *Nature* 343:33-37.

Poulsen et al., "Detection of methicillin resistance in coagulase-negative staphylococci and in staphylococci directly from simulated blood cultures using the EVIGENE MRSA Detection Kit", *J. Antimicrob. Chemother.* (2003) 51(2):419-21.

Ralser et al., "An efficient and economic enhancer mix for PCR", *Biochem. Biophys. Res. Communi.* (2006) 347(3):747-51.

Saito et al., "Immunological detection of penicillin-binding protein 2' of methicillin-resistant staphylococci by using monoclonal antibodies prepared from synthetic peptides", *J. Clin. Microbiol.* (1995) 33(9):2493-500.

Schuenck et al., "Improved and rapid detection of methicillin-resistant *Staphylococcus aureus* nasal carriage using selective broth and multiplex PCR", *Res. Microbiol.* (2006) 157(10):971-5.

Shittu et al., "Molecular identification and characterization of mannitol-negative methicillin-resistant *Staphylococcus aureus*", *Diagn. Microbiol. Infect Dis.* (2007) 57(1):93-5.

Sooknanan et al., "NASBA: A detection and amplification system uniquely suited for RNA", *Biotechnology* (1995) 13:563-564.

Switzer et al., "Enzymatic recognition of the base pair between isocytidine and isoguanosine", *Biochemistry* (1993) 32:10489-10496.

Thelwell et al., "Mode of action and application of Scorpion primers to mutation detection", *Nucl. Acids Res.* (2000) 28(19):3752-61.

Tor et al., "Site-Specific Enzymatic Incorporation of an Unnatural Base, N6 -(6-Aminohexyl) isoguanosine, into RNA", *J. Am. Chem. Soc.* (1993) 115:4461-4467.

Tyagi et al., "Molecular beacons: probes that fluoresce upon hybridization", *Nat. Biotechnol.* (1996) 14(3):303-8.

Ubukata et al., "Homology of mecA gene in methicillin-resistant *Staphylococcus haemolyticus* and Staphylococcus simulans to that of *Staphylococcus aureus*", *Antimicrob. Agents Chemother.* (1990) 34(1):170-2.

Ubukata et al., "Rapid detection of the mecA gene in methicillin-resistant staphylococci by enzymatic detection of polymerase chain reaction products" *J. Clin. Microbiol.* (1992) 30:1728-33.

Van Brunt, "Amplifying genes: PCR and its alternatives", *Biotechnology* (1990) 8(4):291-4.

Vannuffel et al. Specific detection of methicillin-resistant Staphylococcus species by multiplex PCR. Journal of Clinical Microbiology. 33(11):2864-2867 (1995).

White, "Molecular Cloning to Genetic Engineering", in *Methods in Molecular Biology* Humana Press (1997) vol. 67, Contents pages only.

Wilson et al., "Detection of enterotoxigenic *Staphylococcus aureus* in dried skimmed milk: use of the polymerase chain reaction for amplification and detection of staphylococcal enterotoxin genes entB and entC1 and the thermonuclease gene nuc", *Appl. Environ. Microbiol.* (1991) 57:1793-8.

Wilson, "Inhibition and facilitation of nucleic acid amplification", *Appl. Environ. Microbiol.* (1997) 63(10):3741-51.

Wu et al., "The ligation amplification reaction (LAR)—amplification of specific DNA sequences using sequential rounds of template-dependent ligation", *Genomics* (1989) 4(4):560-9.

Zhang et al., "Novel multiplex PCR assay for characterization and concomitant subtyping of staphylococcal cassette chromosome mec types I to V in methicillin-resistant *Staphylococcus aureus.*", *J. Clin. Microbiol.* (2005) 43(10): 5026-33.

Zhang et al., "New quadriplex PCR assay for detection of methicillin and mupirocin resistance and simultaneous discrimination of *Staphylococcus aureus* from coagulase-negative staphylococci", *J. Clin. Microbiol.* (2004) 42(11):4947-55.

Partial International Search Report for International Application No. PCT/US2007/088004 dated Dec. 19, 2008.

Baba et al. "*Staphylococcus aureus* subsp. Aureus MW2 DNA, complete genome", retrieved from EBI Database accession No. AP004822 (May 27, 2002), replaced by Accession No. BA000033.

Cheng et al., "Effective amplification of long targets from cloned inserts and human genomic DNA," Proc Natl Acad Sci. USA, (Jun. 1994) 91: 5695-5699.

Crisóstomo et al., "The evolution of methicillin resistance in *Staphylococcus aureus*: Similarity of genetic backgrounds in historically early methicillin-susceptible and -resistant isolates and contemporary epidemic clones", Proc Natl Acad Sci USA, (Aug. 2001) 98(17): 9865-9870.

Database Geneseq [Online]. Sequence provided in Fig. 4 of JP11056371. Retrieved from EBI accession No. GSN:AAX32450 (Jun. 22, 1999).

Database Geneseq [Online]. "Identification method" JP1999056371, Retrieved from EBI accession No. EM-PRO:E60314 (Feb. 22, 2001).

Database Geneseq [Online]. "Sequence of Primer KC1". Retrieved from EBI accession No. GSN:AAX32446 (Jun. 22, 1999).

Diefenbach, Dveksler. "PCR Primer: A Laboratory Manual", 1995, Cold Spring Harbor Laboratory Press (Cover & Contents pages only).
Edwards et al., "Multiplex PCR: advantages, development, and applications", Genome Res. (1994) 3: S65-75.
Ito et al. "*Staphylococcus aureus* DNA, 3' flanking region of mecDNA, strain 64/4176." GenBank accession No. AB014434, Jan. 7, 2000—Abstract only.
Kobayashi et al., "Genomic diversity of *mec* regulator genes in methicillin-resistant *Staphylococcus aureus* and *Staphylococcus epidermidis*", Epidemiol Infect. (1996) 117(2): 289-295.
Lee et al., "Nucleic Acid Amplification Technologies: Application to Disease Diagnosis", 1997, Eaton Publishing (Cover pages Only).
Lewin, "Genes IV", 1990, John Wiley & Sons, Chapter 3, Genes are Mutable Units, pp. 41-56.
Ma et al. "*Staphylococcus aureus* DNA, type-IV.2 (Ivb) staphylococcal cassette chromosome mec: strain JCSC1978 (8/6-3P)", EBI GenBank accession No. AB063173, Nov. 21, 2001.
Oliveira et al. "*Staphylococcus aureus* strain HDE288 type-VI SCCmec element, complete sequence" GenBank Accession Version No. AF411935, Mar. 5, 2002, pp. 8.
Oliveira et al. "*Staphylococcus aureus* strain PL72 genomic sequence upstream of mecA" GenBank Accession Version No. AF411936, Mar. 5, 2002, pp. 3.
Sambrook et al., "Molecular Cloning: A Laboratory Manual", 1989 Cold Spring Harbor Laboratory Press (Cover & Contents pages only).
Seki et al., Amplification of long targets of approximately 50 kb from cloned cosmid inserts of *Arabidopsis thaliana*, DNA Research (Jul. 1996) 3: 107-108.
Turbeville et al., "Amplification of the complete mitochondrial genome of two protostome worms: a useful technique for comparative studies of metazoan mitochondrial DNA", Mol Marine Bio Biotech., 6(2): 141-143 (1997).
Van Leeuwen et al., "Genetic diversification of methicillin-resistant *Staphylococcus aureus* as a function of prolonged geographic dissemination and as measured by binary typing and other genotyping methods," Res Microbiol, 149: 497-507 (1998).
Watson et al., "Molecular Biology of the Gene", 1987, The Benjamin/Cummings Publishing Company (Cover pages only).
Walker, et al., "Isothermal in vitro Amplification of DNA by a Restriction Enzyme/DNA Polymerase System," Proc Natl Acad Sci. USA, 89: 392-396 (Jan. 1992).
Ciardo et al., "GeneXpert Captures Unstable Methicillin-Resistant *Staphylococcus aureus* Prone to Rapidly Losing the *mecA*Gene," J. Clin. Microbio. (Aug. 2010) 48(8):3030-3031.
Database EMBL [Online]. "*Staphylococcus aureus* DNA, 3' flanking region of MecDNA, strain 64/4176", Retrieved from EBI accession No. AB014434 (Jan. 7, 2000).
Database EMBL [Online]. "*Staphylococcus aureus* M type 1 capsular polysaccharide biosynthesis gene cluster, complete sequence and unknown genes", Retrieved from EBI accession No. SA10927 (Nov. 8, 1994).
Database EMBL [Online]. "*Staphylococcus aureus* DNA, type-IV.1 (Iva) staphylococcal cassette chromosome mec: strain CA05 (JCSC1968)", retrieved from EBI accession No. AB063172 (Nov. 21, 2001).
Database Geneseq [Online]. "*Staphylococcus aureus* downstream junction sequence Psj10-3J3rc.", Retrieved from EBI accession No. GSN:AAT84818 (Mar. 23, 1998).
GenBank accession No. D86934.1, "*Staphylococcus aureus* genes, mec region, partial and complete cds.", Jul. 3, 1999.
Huletsky, et al. "Identification of Methicillin-Resistant *Staphylococcus aureus* Carriage in Less than 1 Hour during a Hospital Surveillance Program." Clin. Infect. Dis. (Apr. 2005) 40: 976-981.
Kobayashi et al., "Analysis on distribution of insertion sequence IS431 in clinical isolates of *staphylococci*", Diag. Micro. Infect. Dis. (2001) 39: 61-64.
Bartels et al., "An unexpected location of the Arginine Catabolic Mobile Element (ACME) in a USA300-related MRSA." PLoS ONE 6(1): e16193 (Jan. 2011).
BLAST Sequence-Alignment 1 between AB037671 (strain 85/2082) and Seq ID No. 42, printed on Apr. 1, 2011, pp. 2.

Cuny et al., "PCR for the identification of methicillin-resistant *Staphylococcus aureus* (MRSA) strains using a single primer pair specific for SCC*mec* elements and the neighbouring chromosome-borne *orfX*."—Research Note, Clin Microbio Infect., 11(10): 834-837 (Oct. 2005).
Domann et al. "Schneller and zuverlaessiger Nachweis multiresistenter multiplex-PCR." Deutsche Medizinische Wochenschrift. 125(20): 613-618 (2000), abstract only.
GenBank accession No. AB037671, "*Staphylococcus aureus* DNA, type-III staphylococcal cassette chromosome mec and SCCmercury: strain 85/2082", May 12, 2000, pp. 30.
Hanssen et al., "Local Variants of Staphylococcal Cassette Chromosome *mec* in Sporadic Methicillin-Resistant *Staphylococcus aureus* and Methicillin-Resistant Coagulase-Negative Staphylococci: Evidence of Horizontal Gene Transfer?" Antimicrob Agents Chemothera., 48(1): 285-296 (Jan. 2004).
Hanssen et al., Mini Review "SCC*mecin* staphylococci: genes on the move." FEMS Immunol Med Microbiol., 46: 8-20 (Sep. 2005).
NCBI BLAST Sequence Alignment 1 between AB037671 (strain 85/2082) and Seq ID No. 42, printed on Apr. 1, 2011.
Okuma et al., "Dissemination of new methicillin-resistant *Staphylococcus aureus* clones in the community." J Clin Microbio., 40(11): 4289-4294 (Nov. 2002).
Wisplinghoff et al., "Related clonges containing SCC*mec* type IV predominate among clinically significant *Staphylococcus epidermidis* Isolates." Antimicrob Agents Chemothera. 47(11): 3574-3579 (2003).
Sequence Alignment 3 printed on Mar. 31, 2011 aligning the Nucleotide Sequence of Staphylococcal aureus strains 85/2082, HDG2, and N315(d86934) downs stream of mecA, pp. 10.
European Office Action dated Sep. 28, 2011 for European Application No. 07874372.1, filed Dec. 18, 2007.
Electronic File History of Inter Partes Reexamination Control No. 95/001599, filed Apr. 8, 2011 containing Office Actions dated Apr. 19, 2011, Jun. 1, 2011 and Dec. 29, 2011, Requestor submissions Apr. 8, 2011, and Aug. 31, 2011 and Applicant Response filed Aug. 5, 2011.
European Extended Search Report dated Apr. 18, 2011 in European Patent Application No. 10181533.0, filed Jun. 4, 2002.
European Extended Search Report dated Apr. 18, 2011 in European Patent Application No. 10181534.8, filed Jun. 4, 2002.
European Extended Search Report dated Apr. 18, 2011 in European Patent Application No. 10181535.8, filed Jun. 4, 2002.
European Extended Search Report dated Apr. 15, 2011 in European Patent Application No. 10181536.3, filed Jun. 4, 2002.
European Office Action dated Apr. 26, 2011 in European Patent Application No. 09174581.0, filed Jun. 4, 2002.
Partial European Search Report dated Mar. 31, 2011 for European Patent Application No. 10016072.0, filed Oct. 10, 2006.
Extended European Search Report dated Aug. 10, 2011 for European Patent Application No. 10016072.0, filed Oct. 10, 2006.
Partial European Search Report dated Mar. 31, 2011 for European Patent Application No. 10016073.8, filed Oct. 10, 2006.
Extended European Search Report dated Aug. 10, 2011 for European Patent Application No. 10016073.8, filed Oct. 10, 2006.
Partial European Search Report dated Mar. 10, 2011 for European Patent Application No. 10016074.6, filed Oct. 10, 2006.
Extended European Search Report dated Jul. 20, 2011 for European Patent Application No. 10016074.6, filed Oct. 10, 2006.
Partial European Search Report dated Mar. 31, 2011 for European Patent Application No. 10016031.6, filed Oct. 10, 2006.
Extended European Search Report dated Aug. 10, 2011 for European Patent Application No. 10016031.6, filed Oct. 10, 2006.
Partial European Search Report dated Mar. 30, 2011 for European Patent Application No. 10016019.1, filed Oct. 10, 2006.
Extended European Search Report dated Aug. 10, 2011 for European Patent Application No. 10016019.1, filed Oct. 10, 2006.
Partial European Search Report dated Mar. 30, 2011 for European Patent Application No. 10016020.9, filed Oct. 10, 2006.
Extended European Search Report dated Aug. 10, 2011 for European Patent Application No. 10016020.9, filed Oct. 10, 2006.
Third Party Observations dated Jan. 17, 2008 in European Patent Application No. 02740158.7, filed Jun. 4, 2002.

Notice of Opposition dated Aug. 4, 2010 in European Patent Application No. 02740158.7, filed Jun. 4, 2002.
Notice of Opposition dated Aug. 3, 2010 in European Patent Application No. 02740158.7, filed Jun. 4, 2002.
EPO Communication dated Sep. 10, 2010 in European Patent Application No. 02740158.7, filed Jun. 4, 2002.
Patentee Response to Opposition dated Mar. 17, 2011 European Patent Application No. 02740158.7, filed Jun. 4, 2002.
Notice of Opposition & Discussion filed Oct. 19, 2011against European Patent No. 1934613, issued Jan. 19, 2011 (Koenig et al.).
Notice of Opposition and Statement filed Oct. 18, 2011 against European Patent No. 1934613, issued Jan. 19, 2011 (BC).
EPO Communication dated Nov. 25, 2011 in European Patent No. 1934613, issued Jan. 19, 2011.
Dieffenbach et al. "General Concepts for PCR Primer Design." Genome Res. 3: S30-S37 (1993).
GenBank accession No. X53818.1, "*Staphylococcus aureus* IS431mec gene associated with methicillin resistance", Oct. 23, 2008.
Huletsky, A.—Declaration in Reexamination of US Patent 7,449,289 dated Jul. 30, 2011; pp. 3.
NCBI BLAST 2 Sequence—AF411934.1—*Staphylococcus aureus* strain HDG2 genomic sequence downstream of mecA, printed on Mar. 16, 2012, pp. 2.
Alignment of Seq ID Nos. 42-46 and 51 with HDG2 sequence; GenBank Accession Version No. AF411934; Exhibit D9a in European Opposition of Patent No. 1397510, issued Mar. 17, 2004; pp. 10.
Oliveira, D.—Email re Sequence Question with Hema Pande, Beckman Coulter, Inc. (Jul. 2010).
Oliveira, D—Declaration in Opposition to EP Patent 1397510 dated Nov. 29, 2012; pp. 2.
Random House Unabridged Dictionary, (1993) Definition of "extremity", p. 686.
Sanches et al., "Tracing the Origin of an Outbreak of Methicillin-Resistant *Staphylococcus aureus* Infections in a Portuguese Hospital by Molecular Fingerprinting Methods." Microbial Drug Resist. 2(3): 319-329 (1996).
Singh et al. "PCR Primer Design." Mol Biol Today 2(2): 27-32 (2001).
D3—Exhibit in European Opposition Proceeding: Applicant Response dated Dec. 2, 2009 in EP Application No. 06825875.5, filed Oct. 10, 2006; 5 pages.
D32—Exhibit in European Opposition Proceeding: Lawrence et al. "Poisonous EPC Divisionals—Implications for Risk Management and Opportunistic Advantage." epi Information Feb. 2011; 54-61.
D36—Exhibit in European Opposition Proceeding: Alignment of Seq ID No. 18 from U.S. Appl. No. 11/248,438 and WO 2007/044873 with orfX sequence from Ito et al., AB014440; 3 pages.
D37—Exhibit in European Opposition Proceeding: Alignment of Seq ID No. 19 from U.S. Appl. No. 11/248,438 and WO 2007/044873 with orfX sequence from Ito et al., AB014440; 1 page.
D38—Exhibit in European Opposition Proceeding: Alignment of MREJ type xi (Seq ID No. 17) and mrej Type iii (Seq ID No. 184 from WO 2002/099034 showing asserted binding sites of primers pair (Seq ID Nos. 64/98) from WO 2002/099034; 3 pages.
D39—Exhibit in European Opposition Proceeding: Alignment of MREJ type xi (Seq ID No. 17) and MREJ type iii (Seq ID No. 184 From WO 2002/099034 showing asserted binding sites of primers (Seq ID Nos. 1-5) from EP 1 529 847; 1 page.
Electronic File History of Inter Partes Reexamination Control No. 95/002,216, filed Sep. 13, 2012 for U.S. Appl. No. 11/248,438, filed Oct. 11, 2005 (USP 7,838,221) as of Feb. 26, 2013.
Office Action dated Sep. 11, 2012 for European Patent Application No. 10016072.0, filed Oct. 10, 2006.
Office Action dated Sep. 11, 2012 for European Patent Application No. 10016073.8, filed Oct. 10, 2006.
Office Action dated Sep. 11, 2012 for European Patent Application No. 10016074.6, filed Oct. 10, 2006.
Office Action dated Sep. 11, 2012 for European Patent Application No. 10016031.6, filed Oct. 10, 2006.
Office Action dated Sep. 11, 2012 for European Patent Application No. 10016019.1, filed Oct. 10, 2006.
Office Action dated Sep. 12, 2012 for European Patent Application No. 10016020.9, filed Oct. 10, 2006.
Australian Office Action dated Sep. 5, 2012 for Australian Application No. 2007353522, filed Dec. 19, 2006.
Japanese Office Action dated Nov. 27, 2012 in Japanese Patent Application No. 2009-543155, filed Dec. 18, 2007.
Patentee Response dated Nov. 19, 2012 to EP Summons to Oral Proceeding in European Opposition to Patent No. 1397510.
Opposer Hain Lifescience GmbH Response dated Nov. 26, 2012 to EP Summons to Oral Proceeding in European Opposition to Patent No. 1397510. (English Translation Only).
Opposer Beckman Coulter, Inc. further Response dated Nov. 30, 2012 to EP Summons to Oral Proceeding in European Opposition to Patent No. 1397510.
Patentee Reply filed May 30, 2012 in European Opposition to Patent No. 1934613.
EPO Summons to Oral Proceedings dated Nov. 23, 2012 in European Opposition to Patent No. 1934613.
Australian Office Action dated Jun. 6, 2011 for Australian Application No. 2006302044, filed Oct. 10, 2006.
European Office Action dated Apr. 16, 2012 for European Application No. 07874372.1, filed Dec. 18, 2007.
EPO Communication dated May 10, 2012 re Oral Proceeding Schedule in European Opposition No. 02740158.7, filed Jun. 4, 2002.
Japanese Office Action dated Mar. 13, 2012 for JP Patent Application No. 2008-535692, filed Oct. 10, 2006.
Japanese Office Action dated Aug. 8, 2012 for JP Patent Application No. 2008-535692, filed Oct. 10, 2006.
Arakere, et al. "A novel type-III Staphylococcal cassette chromosome mec (SCCmec) variant among Indian isolates of methicillin-resistant *Staphylococcus aureus*." FEMS Microbiol. Lett. 292(1): 141-148 (Mar. 2009).
Mongkolrattanothai et al. "Novel Non-mecA-Containing Staphylococcal Chromosomal Cassette Composite Island Containing pbp4 and tagF Genes in a Commensal Staphylococcal Species: a Possible Reservoir for Antibiotic Resistance Islands in *Staphylococcus aureus*." Antimicrob. Agents Chemother. (May 2004) 48(5): 1823-1836.
Podzorski et al., Evaluation of the MVPlex Assay for Direct and Rapid Detection of Methicillin-Resistant *Staphylcoccus aureus* from Nares and Other Swab Speciments, (Abstract C-237), American Society for Microbiology 107th Meeting, Toronto, Canada May 21-25, 2007, p. 186.
Podzorski et al., MVPIex Assay for Direct Detection of Methicillin-Resistant *Staphylococcus aureus* in Naris and Other Swab Specimens, J Clin Microbiol. (Sep. 2008/09) 46(9): 3107-3109.
Shore et al. "Characterization of a Novel Arginine Catabolic Mobile Element (ACME) and Staphylococcal Chromosomal Cassette mec Composite Island with Significant Homology to Staphylococcus epidermidis ACME Type II in Methicillin-Resistant Staphylococcus aureus Genotype ST22-MRSA-IV." Antimicrob Agents Chemother. (May 2011) 55(5): 1896-1905.
Simor, et al. "Characterization and proposed nomenclature of epidemic strains of methicillin-resistant *Staphylococcus aureus* in Canada." Can J Infect Dis. Sep.-Oct. 1999; 10(5): 333-336.
Tang et al., StaphPlex System for Rapid and Simultaneous Identification of Antibiotic Resistance Determinants and Panton-Valentine Leukocidin Detection of Staphylococci from Positive Blood Cultures, J Clin Microbiol. (Jun. 2007) 45(6): 1867-1873.
Comparison of the nucleotide sequence of MRSA strain V14 (deposited under Accession No. AB425427) with the nucleotide sequence of SEQ ID No.: 165 from the Patent. Primer binding sites for some of the primers claimed in claim 4 of the EP2236621 [D12] cited on May 8, 2013; pp. 1-7.
Nucleotide Sequence of MRSA strain M08/1026 ACME/SCCmecCl of ST22-MRSA-Ivh deposited in Genbank Accession No. FR753166 with orfX and SCCmec portions of SEQ ID No.: 165 highlighted thereon. Also shown are primers binding sites for the primers of SEQ ID Nos. 64 and 112 from claim 5 of the EP2236621 [D14] cited on May 8, 2013; pp. 116.
CLUSTALW2 Multiple nucleotide sequence alignment (generated using ClustalW2). The sequence of each of MREJ types I to xx (excluding type x) is aligned around the integratioin site. The sequence of the rjmec primer from D7 is also included; [D9] cited on May 8, 2013; p. 1.

Nucleotide Sequence alignment of SEQ ID No.: 165 of EP2236621 [D17] with *Staphylococcus epidermidis* strain ATCC 12228 (Accession No. AE015929.1) cited on May 8, 2013; p. 1.

Blast Sequence-Alignment between the orfX sequence from *Staphyloccocus aureus* and the equivalent *Staphylococcus epidermidis* sequence taken from a number of strains; [D19] cited on May 8, 2013; pp. 1-6.

SEQ ID No.: 6—Figure 19 of D1 and D2. Primer biding sites for Seq ID Nos. 64 and 98 from EP2236621 as underlined; [D22] cited on May 8, 2013; p. 1.

European Decision T 1496/11 of the Technical Boards of Appeal in re EP Patent No. 930979 [D28] of Sep. 12, 2012; pp. 1-28.

Annotated version of figure 4A of EP 2236621 cited on May 8, 2013; p. 1.

Sequence Alignment of SEQ ID No.: 64 and SEQ ID No.: 98 on SEQ ID No.: 165 and SEQ ID No.: 166 of EP2236621 [D31] cited on May 8, 2013; pp. 1-3.

European Extended Search Report dated Aug. 10, 2010 in European Patent Application No. 09174581.0, filed Jun. 4, 2002. [D33].

Response to Extended Search Report filed Mar. 3, 2011 in European Patent Application No. 09174581.0, filed Jun. 4, 2002. [D34].

Supplementary Response to Extended Search Report filed Nov. 16, 2011 in European Patent Application No. 09174581.0, filed Jun. 4, 2002. [D35].

Minutes of the Oral Proceedings on Jan. 1, 2013 in European Opposition to Patent No. 1397510 [D37] mailed Apr. 5, 2013.

EPO Decision of the Opposition Division of Apr. 5, 2013 in European Opposition to Patent No. 1397510 [D36].

Notice of Opposition filed May 8, 2013 against European Patent No. 2236621, granted Aug. 8, 2012.

Becker et al., "Does Nasal Cocolonization by Methicillin-Resistant Coagulase-Negative Staphylococci and Methicillin-Susceptible *Staphylococcus aureus* Strains Occur Frequently Enough to Represent a Risk of False Positive Methicillin-Resistant *S. aureus* Determinations by Molecular Methods?", J Clin Microbiol. (Jan. 2006) 44(1): 229-231.

Bishop et al., "Concurrent Analysis of Nose and Groin Swab Specimens by the IDI-MRSA PCR Assay is Comparable to Analysis by Individual-Specimen PCR and Routine Culture Assays for Detection of Colonization by Methicillin-Resistant *Staphylococcus aureus*", J Clin Microbiol. (Aug. 2006) 44(8): 2904-2908.

Desjardins et al., "Evaluation of the IDI-MRSA Assay for Detection of Methicillin-Resistant *Staphylococcus aureus* from Nasal and Rectal Specimens Pooled in a Selective Broth", J Clin Microbiol. (Apr. 2006) 44(4): 1219-1223.

Donnio et al., "Partial Excision of the Chromosomal Cassette Containing the Methicillin Resistance Determinant Results in Methicillin-Susceptible *Staphylococcus aureus*", J Clin Microbiol. (Aug. 2005) 43(8):4191-4193.

Elsayed et al., "Development and Validation of a Molecular Beacon Probe-Based Real-Time Polymerase Chain Reaction Assay for Rapid Detection of Methicillin Resistance in *Staphylococcus aureus*", Arch Pathol Lab Med. (Jul. 2003) 127(7): 845-849.

Levenson, Deborah, "The Path to Better MRSA Control", Clin Lab News. (Aug. 2007) 33(8): 6 pages.

Rupp et al., "Be Aware of the Possibility of False-Positive Results in Single-Locus PCR Assays for Methicillin-Resistant *Staphylococcus aureus*", (Jun. 2006) 44(6): 2317-8.

Warren et al., "Detection of Methicillin-Resistant *Staphylococcus aureus* Directly from Nasal Swab Specimens by a Real-Time PCR Assay", J Clin Microbiol. (Dec. 2004) 42(12): 5578-5581.

* cited by examiner

```
                         SEQUENCE LISTING

<160> NUMBER OF SEQ ID NOS: 205

<210> SEQ ID NO 1
<211> LENGTH: 24
<212> TYPE: DNA
<213> ORGANISM: Artificial Sequence
<220> FEATURE:
<223> OTHER INFORMATION: Staphylococcus aureus

<400> SEQUENCE: 1
acagaatact tattaagtgc tggc                                           24

<210> SEQ ID NO 2
<211> LENGTH: 27
<212> TYPE: DNA
<213> ORGANISM: Artificial Sequence
<220> FEATURE:
<223> OTHER INFORMATION: Staphylococcus aureus

<400> SEQUENCE: 2
gtttcaatat tacttatagg gatggct                                        27

<210> SEQ ID NO 3
<211> LENGTH: 24
<212> TYPE: DNA
<213> ORGANISM: Artificial Sequence
<220> FEATURE:
<223> OTHER INFORMATION: Staphylococcus aureus

<400> SEQUENCE: 3
ctgatggaaa aatggtaaac gaag                                           24

<210> SEQ ID NO 4
<211> LENGTH: 22
<212> TYPE: DNA
<213> ORGANISM: Artificial Sequence
<220> FEATURE:
<223> OTHER INFORMATION: Staphylococcus aureus

<400> SEQUENCE: 4
atggaaaaat ggtaaacgaa gc                                             22

<210> SEQ ID NO 5
<211> LENGTH: 22
<212> TYPE: DNA
<213> ORGANISM: Artificial Sequence
<220> FEATURE:
<223> OTHER INFORMATION: Staphylococcus aureus

<400> SEQUENCE: 5
tgctgagcta cttagacttg aa                                             22

<210> SEQ ID NO 6
<211> LENGTH: 22
<212> TYPE: DNA
<213> ORGANISM: Artificial Sequence
<220> FEATURE:
<223> OTHER INFORMATION: Staphylococcus aureus
```

-continued

```
<400> SEQUENCE: 6
gcatttgctg agctacttag ac                                              22

<210> SEQ ID NO 7
<211> LENGTH: 25
<212> TYPE: DNA
<213> ORGANISM: Artificial Sequence
<220> FEATURE:
<223> OTHER INFORMATION: Staphylococcus aureus

<400> SEQUENCE: 7
gttgttcatg tgtattgtta ggttt                                           25

<210> SEQ ID NO 8
<211> LENGTH: 22
<212> TYPE: DNA
<213> ORGANISM: Artificial Sequence
<220> FEATURE:
<223> OTHER INFORMATION: Staphylococcus aureus

<400> SEQUENCE: 8
ttattgacct gaatcagcgt tg                                              22

<210> SEQ ID NO 9
<211> LENGTH: 30
<212> TYPE: DNA
<213> ORGANISM: Artificial Sequence
<220> FEATURE:
<223> OTHER INFORMATION: Staphylococcus aureus

<400> SEQUENCE: 9
cgaaacatta ctgatagcca tccctataag                                      30

<210> SEQ ID NO 10
<211> LENGTH: 40
<212> TYPE: DNA
<213> ORGANISM: Artificial Sequence
<220> FEATURE:
<223> OTHER INFORMATION: Staphylococcus aureus

<400> SEQUENCE: 10
cgcaccgaaa cattactgat agccatccct ataaggtgcg                           40

<210> SEQ ID NO 11
<211> LENGTH: 29
<212> TYPE: DNA
<213> ORGANISM: Artificial Sequence
<220> FEATURE:
<223> OTHER INFORMATION: Staphylococcus aureus

<400> SEQUENCE: 11
acataagcaa ctttagccaa gccttgacg                                       29

<210> SEQ ID NO 12
<211> LENGTH: 41
<212> TYPE: DNA
<213> ORGANISM: Artificial Sequence
<220> FEATURE:
<223> OTHER INFORMATION: Staphylococcus aureus

<400> SEQUENCE: 12
cgcgcaacat aagcaacttt agccaagcct tgacgtgcgc g                         41

<210> SEQ ID NO 13
<211> LENGTH: 26
```

```
<212> TYPE: DNA
<213> ORGANISM: Artificial Sequence
<220> FEATURE:
<223> OTHER INFORMATION: Staphylococcus aureus

<400> SEQUENCE: 13
atgtcaaaaa tcatgaacct cattac                                          26

<210> SEQ ID NO 14
<211> LENGTH: 3050
<212> TYPE: DNA
<213> ORGANISM: Artificial Sequence
<220> FEATURE:
<223> OTHER INFORMATION: Staphylococcus aureus

<400> SEQUENCE: 14
tcgtgccatt gatgcagagg gacatacatt agatatttgg ttgcgtaagc aacgagataa      60
tcattcagca tatgcgttta tcaaacgtct cattaaacaa tttggtaaac ctcaaaaggt     120
aattacagat caggcacctt caacgaaggt agcaatggct aaagtaatta aagcttttaa     180
acttaaacct gactgtcatt gtacatcgaa atatctgaat aacctcattg agcaagatca     240
ccgtcatatt aaagtaagaa agacaaggta tcaaagtatc aatacagcaa agaatacttt     300
aaaaggtatt gaatgtattt acgctctata taaaaagaac cgcaggtctc ttcagatcta     360
cggattttcg ccatgccacg aaattagcat catgctagca agttaagcga acactgacat     420
gataaattag tggttagcta tattttttta ctttgcaaca gaaccgaaaa taatctcttc     480
aatttatttt tatatgaatc ctgtgactca atgattgtaa tatctaaaga tttcagttca     540
tcatagacaa tgttcttttc aacattttt atagcaaatt gattaaataa attctctaat     600
ttctcccgtt tgatttcact accatagatt atattatcat tgatatagtc aatgaataat     660
gacaaattat cactcataac agtcccaacc cctttatttt gatagactaa ttatcttcat     720
cattgtaaaa caaattacac cctttaaatt taactcaact taaatatcga caaattaaaa     780
aacaataaaa ttacttgaat attattcata atatattaac aactttatta tactgctctt     840
tatatataaa atcattaata attaaacaag cctttaaaata tttaactttt ttgtgattat     900
tacacattat cttatctgct ctttatcacc ataaaaatag aaaaaacaag attcctaaag     960
aatataggaa tcttgtttca gactgtggac aaactgattt tttatcagtt agcttattta    1020
gaaagtttta tttaaattac agtttctatt tttattagat cacaattta ttttagctct    1080 tgttcaagta atcattttc gccaaaaact ttatactgaa tagcttctac attaaatact    1140
ttgtcaatga gatcatctac atctttaaat tcagaataat ttgcatatgg atctataaaa    1200
taaaattgtg gttctttacc ggaaacatta aatattctta atattaaata tttctgctta    1260
tattctttca tagcaaacat ttcatttagc gacataaaaa atggttcctc aatactagaa    1320
gatgtagatg tttttaattc aataaatttt tctacagctt tatctgtatt tgttggatca    1380
aaagctacta atcatagcc atgaccgtgt tgagagcctg gattatcatt taaaatattc    1440
ctaaactgtt cttctttatc ttcgtctatt ttattatcaa ttagctcatt aaagtaattt    1500
agcgctaatt tttctccaac tttaccggtt aatttattct ctttatttga tttttcaatt    1560
tctgaatcat ttttagtagt ctttgataca cctttttttat attttggaat tattcctttta    1620 ggtgcttcca cttccttgag tgtcttatct ttttgtgctg ttctaatttc ttcaatttcg    1680
ctgtcttcct gtatttcgtc tatgctattg accaagctat cataggatgt ttttgtaact    1740
tttgaagcta attcattaaa tagttctaaa aatttcttta aatcctctag catatcttct    1800
tctgtgaatc cttcattcaa atcataatat ttgaatctta ttgatccatg agaatatcct    1860
```

| | |
|---|---|
| gatggataat catttttaa atcataagat gaatctttat tttctgcgta ataaaatctt | 1920 |
| ccagtattaa attcatttga tgtaatatat ttattgagtt cggaagataa agttaatgct | 1980 |
| ctttgttttg cagcatttt atcccgcgga acatatcac ttatctttga ccatccttga | 2040 |
| ttcaaagata agtatatgcc ttctccttcc ggatgaaaaa gatataccaa ataatatcca | 2100 |
| tcctttgttt cttttgttat attctcatca tatattgaaa tccaaggaac tttactatag | 2160 |
| ttcccagtag caaccttccc tacaactgaa tatttatctt cttttatatg cacttttaac | 2220 |
| tgcttgggta acttatcatg gactaaagtt ttatatagat caccttatc ccaatcagat | 2280 |
| ttttaacta cattattggt acgtttctct ttaattaatt taaggacctg cataaagttg | 2340 |
| tctatcattt gaaattccct cctattataa aatatattat gtctcatttt cttcaatatg | 2400 |
| tacttattta tattttaccg taatttacta tatttagttg cagaaagaat tttctcaaag | 2460 |
| ctagaacttt gcttcactat aagtattcag tataaagaat atttcgctat tatttacttg | 2520 |
| aaatgaaaga ctgcggaggc taactatgtc aaaaatcatg aacctcatta ttatgataa | 2580 |
| gcttctcctc gcataatctt aaatgctctg tacacttgtt caattaacac aacccgcatc | 2640 |
| atttgatgtg ggaatgtcat tttgctgaat gatagtgcgt agttactgcg ttgtaagacg | 2700 |
| tccttgtgca ggccgtttga tccgccaatg acgaaaacaa agtcgctttg cccttgggtc | 2760 |
| atgcgttggt tcaattcttg ggccaatcct tcggaagata gcatctttcc ttgtatttct | 2820 |
| aatgtaatga ctgtggattg tggtttgatt ttggctagta ttcgttggcc ttctttttct | 2880 |
| tttacttgct caatttcttt gtcactcata ttttctggtg ctttttcgtc tggaacttct | 2940 |
| atgatgtcta tcttggtgta tgggcctaaa cgttttttcat attctgctat ggcttgcttc | 3000 |
| caatatttct cttttagttt ccctacagct aaaatggtga ttttcatgtc | 3050 |

<210> SEQ ID NO 15
<211> LENGTH: 385
<212> TYPE: DNA
<213> ORGANISM: Artificial Sequence
<220> FEATURE:
<223> OTHER INFORMATION: Staphylococcus aureus

<400> SEQUENCE: 15

| | |
|---|---|
| ttcgtcattg gcggatcaaa cggcctgcac aaggacgtct tacaacgcag taactacgca | 60 |
| ctatcattca gcaaaatgac attcccacat caaatgatgc gggttgtgtt aattgagcaa | 120 |
| gtgtatagag catttaagat tatgcgtgga gaagcttatc ataagtaatg aggttcatga | 180 |
| tttttgacat agttagcctc cgcagtcttt catttcaagt aaataatagc gaaatattct | 240 |
| ttatactgaa tacttatagt gaagcaaagt tctagctttg agaaaattct ttctgcaact | 300 |
| aaatatagta aattacggta aaatataaat aagtacatat tgaagaaaat gagacataat | 360 |
| atattttata ataggaggga atttc | 385 |

<210> SEQ ID NO 16
<211> LENGTH: 385
<212> TYPE: DNA
<213> ORGANISM: Artificial Sequence
<220> FEATURE:
<223> OTHER INFORMATION: Staphylococcus aureus

<400> SEQUENCE: 16

| | |
|---|---|
| ttcgtcattg gcggatcaaa cggcctgcac aaggacgtct tacaacgcag taactacgca | 60 |
| ctatcattca gcaaaatgac attcccacat caaatgatgc gggttgtgtt aattgagcaa | 120 |
| gtgtatagag catttaagat tatgcgtgga gaagcttatc ataagtaatg aggttcatga | 180 |

```
tttttgacat agttagcctc cgcagtcttt catttcaagt aaataatagc gaaatattct      240
ttatactgaa tacttatagt gaagcaaagt tctagctttg agaaaattct ttctgcaact      300
aaatatagta aattacggta aaatataaat aagtacatat tgaagaaaat gagacataat      360
atattttata ataggaggga atttc                                            385
```

<210> SEQ ID NO 17
<211> LENGTH: 385
<212> TYPE: DNA
<213> ORGANISM: Artificial Sequence
<220> FEATURE:
<223> OTHER INFORMATION: Staphylococcus aureus

<400> SEQUENCE: 17

```
ttcgtcattg gcggatcaaa cggcctgcac aaggacgtct tacaacgcag taactacgca      60
ctatcattca gcaaaatgac attcccacat caaatgatgc gggttgtgtt aattgagcaa      120
gtgtatagag catttaagat tatgcgtgga gaagcttatc ataagtaatg aggttcatga      180
tttttgacat agttagcctc cgcagtcttt catttcaagt aaataatagc gaaatattct      240
ttatactgaa tacttatagt gaagcaaagt tctagctttg agaaaattct ttctgcaact      300
aaatatagta aattacggta aaatataaat aagtacatat tgaagaaaat gagacataat      360
atattttata ataggaggga atttc                                            385
```

<210> SEQ ID NO 18
<211> LENGTH: 385
<212> TYPE: DNA
<213> ORGANISM: Artificial Sequence
<220> FEATURE:
<223> OTHER INFORMATION: Staphylococcus aureus

<400> SEQUENCE: 18

```
ttcgtcattg gcggatcaaa cggcctgcac aaggacgtct tacaacgcag taactacgcg      60
ctatcattca gcaaaatgac attcccacat caaatgatgc gggttgtgtt aattgaacaa      120
gtgtacaaag catttaagat tatgcgagga gaagcttatc ataagtaatg aggttcatga      180
tttttgacat agttagcctc cgcagtcttt catttcaagt aaataatagc gaaatattct      240
ttatactgaa tacttatagt gaagcaaagt tctagctttg agaaaattct ttctgcaact      300
aaatatagta aattacggta aaatataaat aagtacatat tgaagaaaat gagacataat      360
atattttata ataggaggga atttc                                            385
```

<210> SEQ ID NO 19
<211> LENGTH: 340
<212> TYPE: DNA
<213> ORGANISM: Artificial Sequence
<220> FEATURE:
<223> OTHER INFORMATION: Staphylococcus aureus

<400> SEQUENCE: 19

```
cgcagtaact acgcgctatc attcagcaaa atgacattcc cacatcaaat gatgcgggtt      60
gtgttagttg agcaagtgta catagcattt aagattatgc gaggagaagc ttatcataag      120
taatgaggtt catgattttt gacatagtta gcctccgcag tctttcattt caagtaaata      180
atagcgaaat attctttata ctgaatactt atagtgaagc aaagttctag ctttgagaaa      240 attcttctg caactaaata tagtaaatta cggtaaaata taataagta catattgaag      300 aaaatgagac ataatatatt ttataatagg agggaatttc                            340
```

<210> SEQ ID NO 20
<211> LENGTH: 369
<212> TYPE: DNA
<213> ORGANISM: Artificial Sequence
<220> FEATURE:
<223> OTHER INFORMATION: Staphylococcus aureus

<400> SEQUENCE: 20

```
caaacggcct gcacaaggac gtcttacaac gcagtaacta cgcactatca ttcagcaaaa      60
tgacattccc acatcaaatg atgcgggttg tgttaattga acaagtgtac agagcattta     120
agattatgcg aggagaagct tatcataagt aatgaggttc atgattttg acatagttag      180 cctccgcagt ctttcatttc aagtaaataa tagcgaaata ttctttatac tgaatactta     240
tagtgaagca agttctagc tttgagaaaa ttctttctgc aactaaatat agtaaattac      300
ggtaaaatat aaataagtac atattgaaga aaatgagaca taatatattt tataatagga    360
gggaatttc                                                            369
```

<210> SEQ ID NO 21
<211> LENGTH: 2480
<212> TYPE: DNA
<213> ORGANISM: Artificial Sequence
<220> FEATURE:
<223> OTHER INFORMATION: Staphylococcus aureus

<400> SEQUENCE: 21

```
aaaccgtctg gcaaacgaat taatgctatt caaattttaa ataaagagac aggtaagttt      60
gaaaatattg atttaaaacg tgtatatcac gtaacgatga atgacttcac agcatcaggt     120
ggcgacggat atagtatgtt cggtggtcct agagaagaag gtatttcatt agatcaagta     180
ctagcaagtt atttaaaaac agctaactta gctaagtatg atacgacaga accacaacgt     240
atgttattag gtaaaccagc agtaagtgaa caaccagcta aggacaaca aggtagcaaa      300 ggtagtaagt ctggtaaaga tacacaacca attggtgacg acaaagtgat ggatccagcg     360
aaaaaaccag ctccaggtaa agttgtattg ttgctagcgc atagaggaac tgttagtagc     420
ggtacagaag gttctggtcg cacaatagaa ggagctactg tatcaagcaa gagtgggaaa     480
caattggcta gaatgtcagt gcctaaaggt agcgcgcatg agaaacagtt accaaaaact     540
ggaactaatc aaagttcaag cccagaagcg atgtttgtat tattagcagg ataggtttta    600
atcgcgactg tacgacgtag aaaagctagc taaaatatat tgaaaataat actactgtat     660
ttcttaaata gaggtacgg tagtgttttt ttatgaaaaa aagcgataac cgttgataaa      720
tatgggatat aaaaacgagg ataagtaata agacatcaag gtgtttatcc acagaaatgg     780
ggatagttat ccagaattgt gtacaattta aagagaaata cccacaatgc ccacagagtt     840
acccacaaat acacaggtta tacactaaaa atcgggcata aatgtcagga aaatatcaaa     900
aactgcaaaa atattggta taataagagg gaacagtgtg aacaagttaa taacttgtgg      960
ataactggaa agttgataac aatttggagg accaaacgac atgaaaatca ccattttagc    1020
tgtagggaaa ctaaaagaga atatattgaa gcaagccata gcagaatatg aaaaacgttt    1080
aggcccatac accaagatag acatcataga agttccagac gaaaaagcac cagaaaatat     1140
gagtgacaaa gaaattgagc aagtaaaaga aaagaaggc caacgaatac tagccaaaat      1200
caaaccacaa tccacagtca ttacattaga aatacaagga aagatgctat cttccgaagg     1260
attggcccaa gaattgaacc aacgcatgac ccaagggcaa agcgactttg ttttcgtcat     1320
tggcggatca aacggcctgc acaaggacgt cttacaacgc agtaactacg cactatcatt     1380
cagcaaaatg acattcccac atcaaatgat gcgggttgtg ttaattgaac aagtgtacag    1440
```

```
agcatttaag attatgcgag gagaagctta tcataagtaa tgaggttcat gatttttgac    1500
atagttagcc tccgcagtct ttcatttcaa gtaaataata gcgaaatatt ctttatactg    1560
aatacttata gtgaagcaaa gttctagctt tgagaaaatt ctttctgcaa ctaaatatag    1620
taaattacgg taaaatataa ataagtacat attgaagaaa atgagacata atatatttta    1680
taataggagg gaatttcaaa tgatagacaa ctttatgcag gtccttaaat taattaaaga    1740
gaaacgtacc aataatgtag ttaaaaaatc tgattgggat aaaggtgatc tatataaaac    1800
tttagtccat gataagttac ccaagcagtt aaaagtgcat ataaaagaag ataaatattc    1860
agttgtaggg aaggttgcta ctgggaacta tagtaaagtt ccttggattt caatatatga    1920
tgagaatata acaaaagaaa caaaggatgg atattatttg gtatatcttt ttcatccgga    1980
aggagaaggc atatacttat ctttgaatca aggatggtca agataagtg atatgtttcc    2040 gcgggataaa aatgctgcaa aacaaagagc attaacttta tcttccgaac tcaataaata    2100
tattacatca aatgaattta atactggaag attttattac gcagaaaata aagattcatc    2160
ttatgattta aaaaatgatt atccatcagg atattctcat ggatcaataa gattcaaata    2220
ttatgatttg aatgaaggat tcacagaaga agatatgcta gaggatttaa agaaattttt    2280
agaactattt aatgaattag cttcaaaagt tacaaaaaca tcctatgata gcttggtcaa    2340
tagcatagac gaaatacagg aagacagcga aattgaagaa attagaacag cacaaaaaga    2400
taagacactc aaggaagtgg aagcacctaa aggaataatt ccaaaatata aaaaaggtgt    2460
atcaaagact actaaaaatg                                              2480

<210> SEQ ID NO 22
<211> LENGTH: 709
<212> TYPE: DNA
<213> ORGANISM: Artificial Sequence
<220> FEATURE:
<223> OTHER INFORMATION: Staphylococcus aureus

<400> SEQUENCE: 22
tacattagaa atacaaggaa agatgctatc ttccgaagga ttggcccaag aattgaacca      60
acgcatgacc caagggcaaa gcgactttgt tttcgtcatt ggcggatcaa acggcctgca     120
caaggacgtc ttacaacgca gtaactacgc actatcattc agcaaaatga cattcccaca     180
tcaaatgatg cgggttgtgt taattgaaca agtgtacaga gcatttaaga ttatgcgagg     240
agaagcttat cataagtaat gaggttcatg attttttgaca tagttagcct ccgcagtctt     300
tcatttcaag taaataatag cgaaatattc tttatactga atacttatag tgaagcaaag     360
ttctagcttt gagaaaattc tttctgcaac taaatatagt aaattacggt aaaatataaa     420
taagtacata ttgaagaaaa tgagacataa tatattttat aataggaggg aatttcaaat     480
gatagacaac tttatgcagg tccttaaatt aattaaagag aaacgtacca ataatgtagt     540
taaaaaatct gattgggata aaggtgatct atataaaact ttagtccatg ataagttacc     600
caagcagtta aaagtgcata taaaagaaga taaatattca gttgtaggga aggttgctac     660
tgggaactat agtaaagttc cttggatttc aatatatgat gagaatata                  709

<210> SEQ ID NO 23
<211> LENGTH: 3050
<212> TYPE: DNA
<213> ORGANISM: Artificial Sequence
<220> FEATURE:
<223> OTHER INFORMATION: Staphylococcus aureus

<400> SEQUENCE: 23
```

```
acctcattga gcaagatcac cgtcatatta aagtaagaaa gacaaggtat caaagtatca      60
atacagcaaa gaatacttta aaaggtattg aatgtattta cgctctatat aaaaagaacc     120
gcaggtctct tcagatctac ggattttcgc catgccacga aattagcatc atgctagcaa     180
gttaagcgaa cactgacatg ataaattagt ggttagctat atttttttac tttgcaacag     240
aaccgaaaat aatctcttca atttatttt atatgaatcc tgtgactcaa tgattgtaat      300
atctaaagat ttcagttcat catagacaat gttcttttca acattttta tagcaaattg      360 attaaataaa ttctctaatt tctcccgttt gatttcacta ccatagatta tattatcatt     420
gatatagtca atgaataatg acaaattatc actcataaca gtcccaaccc ctttcttttg     480
atagactaat tatcttcatc attgtaaaac aaattacacc ctttaaattt aactcaactt     540
aaatatcgac aaattaaaaa acaataaaat tacttgaata ttattcataa tatattaaca     600
actttattat actgctcttt atatataaaa tcattaataa ttaaacaagc cttaaaatat     660 ttaactttt tgtgattatt acacattatc ttatctgctc tttatcacca taaaaataga     720
aaaaacaaga ttcctaaaga ataggaat cttgtttcag actgtggaca aactgatttt      780
ttatcagtta gcttatttag aaagttttat ttaaattaca gtttctattt ttattagatc     840
acaattttat tttagctctt gttcaagtaa tcattttcg ccaaaaactt tatactgaat      900
agcttctaca ttaaatactt tgtcaatgag atcatctaca tctttaaatt cagaataatt     960
tgcatatgga tctataaaat aaaattgtgg ttctttaccg gaaacattaa atattcttaa    1020
tattaaatat ttctgcttat attctttcat agcaaacatt tcatttagcg acataaaaaa    1080
tggttcctca atactagaag atgtagatgt tttaatttca ataaattttt ctacagcttt    1140
atctgtattt gttggatcaa aagctactaa atcatagcca tgaccgtgtt gagagcctgg    1200
attatcattt aaaatattcc taaactgttc tttcttatct tcgtctattt tattatcaat    1260
tagctcatta aagtaatttta gcgctaattt ttctccaact ttaccggtta atttattctc    1320
tttatttgat ttttcaattt ctgaatcatt tttagtagtc tttgatacac cttttttata    1380
ttttggaatt attcctttag gtgcttccac ttccttgagt gtcttatctt tttgtgctgt    1440
tctaatttct tcaatttcgc tgtcttcctg tatttcgtct atgctattga ccaagctatc    1500
ataggatgtt tttgtaactt ttgaagctaa ttcattaaat agttctaaaa atttctttaa    1560
atcctctagc atatcttctt ctgtgaatcc ttcattcaaa tcataatatt tgaatcttat    1620
tgatccatga gaatatcctg atggataatc attttttaaa tcataagatg aatctttatt    1680
ttctgcgtaa taaaatcttc cagtattaaa ttcatttgat gtaatatatt tattgagttc    1740
ggaagataaa gttaatgctc tttgttttgc agcattttta tcccgcggaa acatatcact    1800
tatctttgac catccttgat tcaaagataa gtatatgcct tctccttccg gatgaaaaag    1860
atataccaaa taatatccat cctttgtttc ttttgttata ttctcatcat atattgaaat    1920
ccaaggaact ttactatagt tcccagtagc aaccttccct acaactgaat atttatcttc    1980
ttttatatgc acttttaact gcttgggtaa cttatcatgg actaaagttt tatatagatc    2040
acctttatcc caatcagatt ttttaactac attattggta cgtttctctt taattaattt    2100
aaggacctgc ataagttgt ctatcatttg aaattccctc ctattataaa atatattatg     2160
tctcattttc ttcaatatgt acttatttat attttaccgt aatttactat atttagttgc    2220
agaaagaatt ttctcaaagc tagaactttg cttcactata agtattcagt ataaagaata    2280
tttcgctatt atttacttga aatgaaagac tgcggaggct aactatgtca aaaatcatga    2340
acctcattac ttatgataag cttcttaaaa acataacagc aattcacata aacctcatat    2400
```

```
gttctgatac attcaaaatc cctttatgaa gcggctgaaa aaaccgcatc atttatgata    2460
tgcttctcca cgcataatct taaatgctct atacacttgc tcaattaaca caacccgcat    2520
catttgatgt gggaatgtca ttttgctgaa tgatagtgcg tagttactgc gttgtaagac    2580
gtccttgtgc aggccgtttg atccgccaat gacgaataca aagtcgcttt gcccttgggt    2640
catgcgttgg ttcaattctt gggccaatcc ttcggaagat agcatctttc cttgtatttc    2700
taatgtaatg actgtggatt gtggtttaat tttggctagt attcgttggc cttcttttc    2760 ttttacttgc tcaatttctt tgtcgctcat attttctggt gctttttcgt ctggaacttc    2820
tatgatgtct atcttggtgt atgggcctaa acgttttca tattctgcta tggcttgctt    2880
ccaatatttc tcttttagtt tccctacagc taaaatggtg attttcatgt cgtttggtcc    2940
tccaaattgt tatcaacttt ccagttatcc acaagttatt aacttgttca cactgttccc    3000
tcttattata ccaatatttt ttgcagtttt tgatatttc ctgacattta               3050
```

```
<210> SEQ ID NO 24
<211> LENGTH: 960
<212> TYPE: DNA
<213> ORGANISM: Artificial Sequence
<220> FEATURE:
<223> OTHER INFORMATION: Staphylococcus aureus

<400> SEQUENCE: 24
ttcgtcattg gcggatcaaa cggcctgcac aaggacgtct tacaacgcag taactacgca     60
ctatcattca gcaaaatgac attcccacat caaatgatgc gggttgtgtt aattgaacaa    120
gtgtacagag catttaagat tatgcgtgga gaagcatatc ataaatgatg cggttttttc    180
agccgcttca taagggatt ttgaatgtat cagaacatat gaggtttatg tgaattgctg    240
ttatgttttt aagaagctta tcataagtaa tgaggttcat gatttttgac atagttagcc    300
tccgcagtct ttcatttcaa gtaaataata gcgaaatatt ctttatactg aatacttata    360
gtgaagcaaa gttctagctt tgagaaaatt ctttctgcaa ctaaatatag taaattacgg    420
taaaatataa ataagtacat attgaagaaa atgagacata atatattta taataggagg    480 ttcgtcattg gcggatcaaa cggcctgcac aaggacgtct tacaacgcag taactacgca    540
ctatcattca gcaaaatgac attcccacat caaatgatgc gggttgtgtt aattgagcaa    600
gtgtatagag catttaagat tatgcgtgga gaagcatatc ataaatgatg cggttttttc    660
agccgcttca taagggatt ttgaatgtat cagaacatat gaggtttatg tgaattgctg    720
ttatgttttt aagaagctta tcataagtaa tgaggttcat gatttttgac atagttagcc    780
tccgcagtct ttcatttcaa gtaaataata gcgaaatatt ctttatactg aatacttata    840
gtgaagcaaa gttctagctt tgagaaaatt ctttctgcaa ctaaatatag taaattacgg    900
taaaatataa ataagtacat attgaagaaa atgagacata atatattta taataggagg    960
```

```
<210> SEQ ID NO 25
<211> LENGTH: 480
<212> TYPE: DNA
<213> ORGANISM: Artificial Sequence
<220> FEATURE:
<223> OTHER INFORMATION: Staphylococcus aureus

<400> SEQUENCE: 25
ttcgtcattg gcggatcaaa cggcctgcac aaggacgtct tacaacgcag taactacgca     60
ctatcattca gcaaaatgac attcccacat caaatgatgc gggttgtgtt aattgagcaa    120
gtgtatagag catttaagat tatgcgtgga gaagcatatc ataaatgatg cggttttttc    180
```

```
agccgcttca taaagggatt ttgaatgtat cagaacatat gaggtttatg tgaattgctg      240
ttatgttttt aagaagctta tcataagtaa tgaggttcat gattttgac atagttagcc       300 tccgcagtct ttcatttcaa gtaaataata gcgaaatatt ctttatactg aatacttata     360
gtgaagcaaa gttctagctt tgagaaaatt ctttctgcaa ctaaatatag taaattacgg     420
taaaatataa ataagtacat attgaagaaa atgagacata atatatttta taataggagg     480

<210> SEQ ID NO 26
<211> LENGTH: 458
<212> TYPE: DNA
<213> ORGANISM: Artificial Sequence
<220> FEATURE:
<223> OTHER INFORMATION: Staphylococcus aureus

<400> SEQUENCE: 26
ttcgtcattg gcggatcaaa cggcctgcac aaggacgtct tacaacgcag taactacgca      60
ctatcattca gcaaaatgac attcccacat caaatgatgc gggttgtgtt aattgaacaa     120
gtgtacagag catttaagat tatgcgtgga gaagcatatc ataaatgatg cggttttttc     180
agccgcttca taaagggatt ttgaatgtat cagaacatat gaggtttatg tgaattgctg     240
ttatgttttt aagaagctta tcataagtaa tgaggttcat gattttgac atagttagcc      300 tccgcagtct ttcatttcaa gtaaataata gcgaaatatt ctttatactg aatacttata     360
gtgaagcaaa gttctagctt tgagaaaatt ctttctgcaa ctaaatatag taaattacgg     420
taaaatataa ataagtacat attgaagaaa atgagaca                              458

<210> SEQ ID NO 27
<211> LENGTH: 3050
<212> TYPE: DNA
<213> ORGANISM: Artificial Sequence
<220> FEATURE:
<223> OTHER INFORMATION: Staphylococcus aureus

<400> SEQUENCE: 27
aatttggtaa acctcaaaag gtaattacag atcaggcacc ttcaacgaag gtagcaatgg      60
ctaaagtaat taaagctttt aaacttaaac ctgactgtca ttgtacatcg aaatatctga     120
ataacctcat tgagcaagat caccgtcata ttaaagtaag aaagacaagg tatcaaagta     180
tcaatacagc aaagaatact ttaaaaggta ttgaatgtat tcacgctcta tataaaaaga     240
accgcaggtc tcttcagatc tacggatttt cgccatgcca cgaaattagc atcatgctag     300
caagttaagc gaacactgac atgataaatt agtggttagc tatattttt tactttgcaa      360 cagaaccgaa aataatctct tcaatttatt tttatatgaa tcctgtgact caatgattgt     420
aatatctaaa gatttcagtt catccataga caatgttcttt tcaacatttt ttatagcaaa    480
ttgattaaat aaattctcta atttctcccg tttgatttca ctaccataga ttatattatc    540
attgatatag tcaatgaata atgacaaatt atcactcata acagtcccaa cccctttatt    600
ttgatagact aattatcttc atcattgtaa aacaaattac acccttttaaa tttaactcaa   660 cttaaatatc gacaaattaa aaaacaataa aattacttga atattattca taatatatta   720
acaactttat tatactgctc tttatatata aaatcattaa taattaaaca agccttaaaa   780
tatttaactt ttttgtgatt attacacatt atcttatctg ctctttatca ccataaaaat    840
agaaaaaaca agattcctaa agaatatagg aatcttgttt cagactgtgg acaaactgat    900 ttttatcag ttagcttatt tagaaagttt tatttaaatt acagtttcta tttttattag     960
atcacaattt tattttagct cttgttcaag taatcatttt tcgccaaaaa ctttatactg   1020
```

```
aatagcttct acattaaata cttgtcaatg agatcatcta catctttaaa ttcagaataa    1080
ttcgcatatg gatctataaa ataaaattgt ggttctttac cggaaacatt aaatattctt    1140
aatattaaat atttctgctt atattctttc atagcaaaca tttcatttag cgacataaaa    1200
aatggttcct caatactaga agatgtagat gtttttaattt caataaattt ttctacagct   1260
ttatctgtat ttgttggatc aaaagctact aaatcatagc catgaccgtg ttgagagcct    1320
ggattatcat ttaaaatatt cctaaactgt tctttcttat cttcgtctat tttattatca    1380
attagctcat taaagtaatt tagcgctaat ttttctccaa ctttaccggt taatttattc    1440
tctttatttg attttttcaat ttctgaatca tttttagtag tctttgatac acctttttta   1500
tattttggaa ttattccttt aggtgcttcc acttccttga gtgtcttatc tttttgtgct    1560
gttctaattt cttcaatttc gctgtcttcc tgtatttcgt ctatgctatt gaccaagcta    1620
tcataggatg ttttttgtaac ttttgaagct aattcattaa atagttctaa aaatttcttt   1680
aaatcctcta gcatatcttc ttctgtgaat ccttcattca aatcataata tttgaatctt    1740
attgatccat gagaatatcc tgatggataa tcattttttta aatcataaga tgaatcttta   1800
ttttctgcgt aataaaatct tccagtatta aattcatttg atgtaatata tttattgagt    1860
tcggaagata aagttaatgc tctttgtttt gcagcatttt tatcccgcgg aaacatatca    1920
cttatctttg accatccttg attcaaagat aagtatatgc cttctccttc cggatgaaaa    1980
agatatacca ataatgtcc atcctttgtt tcttttgtta tattctcatc atatattgaa     2040
atccaaggaa ctttactata gttcccagta gcaaccttcc ctacaactga atatttatct    2100
tcttttatat gcacttttaa ctgcttgggt aacttatcat ggactaaagt tttatataga    2160
tcacctttat cccaatcaga ttttttaact acattattgg tacgtttctc tttaattaat    2220
ttaaggacct gcataaagtt gtctatcatt tgaaattccc tcctattata aaatatatta    2280
tgtctcattt tcttcaatat gtacttattt atatttacc gtaatttact atatttagtt     2340
gcagaaagaa ttttctcaaa gctagaactt tgcttcacta taagtattca gtataaagaa    2400
tatttcgcta ttatttactt gaaatgaaag actgcggagg ctaactatgt caaaaatcat    2460
gaacctcatt acttatgata agcttcttaa aaacataaca gcaattcaca taaacctcat    2520
atgttctgat acattcaaaa tcccctttatg aagcggctga aaaaaccgca tcatttatga   2580
tatgcttctc ctcgcataat cttaaatgct ctgtacactt gttcaattaa cacaacccgc    2640
atcatttgat gtgggaatgt catttttgctg aatgatagtg cgtagttact gcgttgtaag   2700
acgtccttgt gcaggccgtt tgatccgcca atgacgaaaa caaagtcgct ttgcccttgg    2760
gtcatgcgtt ggttcaattc ttgggccaat ccttcggaag atagcatctt tccttgtatt    2820
tctaatgtaa tgactgtgga ttgtggtttg attttggcta gtattcgttg gccttctttt    2880
tcttttactt gctcaatttc tttgtcactc atattttctg gtgcttttttc gtctggaact   2940 tctatgatgt ctatcttggt gtatgggcct aaacgttttt catattctgc tatggcttgc    3000
ttccaatatt tctcttttag tttccctaca gctaaaatgg tgattttcat                3050
```

<210> SEQ ID NO 28  
<211> LENGTH: 1501  
<212> TYPE: DNA  
<213> ORGANISM: Artificial Sequence  
<220> FEATURE:  
<223> OTHER INFORMATION: Staphylococcus aureus

<400> SEQUENCE: 28

```
ttgcacaacc aattggtaaa gacaaagtga tggatccagc gaaacaacca gcgccaagta    60
```

```
aagttgtatt gttgccagcg catagaggaa ctgttagtag tggtagagaa ggttctgatc      120
gcgcattgga aggaactgct gtatcaagta agagcgggaa acaattggct agcatgtcag      180
cgcctaaagg tagcacacat gagaagcagt taccaaaaac tggaactgat caaagttcaa      240
gcccagcagc gatgtttgta ttagtagcag gtataggttt aattgcgact gtacgacgta      300
gaaaagctag ctaaaatata ttgaaaacaa tactactgta tttcttaaac aagaggtacg      360
gtagtgtttt tttatgaaaa aaagctataa ccgttgataa atatgggata taaaaacggg      420
gataagtaat aagacatcaa ggtatttatc cacagaaatg gggatagtta tccagaattg      480
tgtacaattt aaagagaaat acccacaatg cccacagagt tatccacaaa tacacaggtt      540
atacactaaa aattgggcat gaatgtcaga aaaatatcaa aaactgcaaa gaatattggt      600
ataataagag ggaacagtgt gaacaagtta ataacttgtg gataactgga aagttgataa      660
caatttggag gaccaaacga catgaaaatc accattttag ctgtagggaa actaaaagag      720
aaatattgga agcaagccat agcagaatat gaaaacgtt taggcccata caccaagata      780
gacatcatag aagttccaga cgaaaaagca ccagaaaata tgagcgacaa agaaattgag      840
caagtaaaag aaaaagaagg ccaacgaata ctagccaaaa tcaaaccaca atcaacagtc      900
attacattag aaatacaagg aaagatgcta tcttccgaag gattggccca agaattgaac      960
caacgcatga cccaagggca aagcgacttt gtattcgtca ttggcggatc aaacggcctg     1020
cacaaggacg tcttacaacg cagtaactac gcactatcat tcagcaaaat gacattccca     1080
catcaaatga tgcgggttgt gttaattgaa caagtgtaca gagcatttaa gattatgcgt     1140
ggagaagcat atcataaatg atgcggtttt ttcagccgct tcataaaggg attttgaatg     1200
tatcagaaca tatgaggttt atgtgaattg ctgttatgtt tttaagaagc ttatcataag     1260
taatgaggtt catgattttt gacatagtta gcctccgcag tctttcattt caagtaaata     1320
atagcgaaat attctttata ctgaatactt atagtgaagc aaagttctag ctttgagaaa     1380
attctttctg caactaaata tagtaaatta cggtaaaata taaataagta catattgaag     1440
aaaatgagac ataatatatt ttataatagg agggaatttc aaatgataga caactttatg     1500
c                                                                    1501
```

<210> SEQ ID NO 29
<211> LENGTH: 917
<212> TYPE: DNA
<213> ORGANISM: Artificial Sequence
<220> FEATURE:
<223> OTHER INFORMATION: Staphylococcus aureus

<400> SEQUENCE: 29

```
aaatacaagg aaagatgcta tcttccgaag gattggccca agaattgaac caacgcatga       60
cccaagggca aagcgacttt gtattcgtca ttggcggatc aaacggcctg cacaaggacg      120
tcttacaacg tagtaactac gcactatcat tcagcaaaat gacattccca catcaaatga      180
tgcgggttgt gttaattgag caagtgtata gagcatttaa gattatgcgt ggagaagcat      240
atcataaatg atgcggtttt ttcagccgct tcataaaggg attttgaatg tatcagaaca      300
tatgaggttt atgtgaattg ctgttatgtt tttaagaagc ttatcataag taatgaggtt      360
catgattttt gacatagtta gcctccgcag tctttcattt caagtaaata atagcgaaat      420
attctttata ctgaatactt atagtgaagc aaagttctag ctttgagaaa attctttctg      480
caactaaata tagtaaatta cggtaaaata taaataagta catattgaag aaaatgagac      540
ataatatatt ttataatagg agggaatttc aaatgataga caactttatg caggtcctta      600
```

```
aattaattaa agagaaacgt accaataatg tagttaaaaa atctgattgg gataaaggtg      660
atctatataa aactttagtc catgataagt tacccaagca gttaaaagtg catataaaag      720
aagataaata ttcagttgta gggaaggttg ctactgggaa ctatagtaaa gttccttgga      780
tttcaatata tgatgagaat ataacaaaag aaacaaagga tggatattat ttggtatatc      840
tttttcatcc ggaaggagaa ggcatatact tatctttgaa tcaaggatgg tcaaagataa      900
gtgatatgtt tccgcgg                                                    917
```

<210> SEQ ID NO 30
<211> LENGTH: 1132
<212> TYPE: DNA
<213> ORGANISM: Artificial Sequence
<220> FEATURE:
<223> OTHER INFORMATION: Staphylococcus aureus

<400> SEQUENCE: 30

```
gctgtaggga aactaaaaga gaaatattgg aagcaagcca tagcagaata tgaaaaacgt       60
ttaggcccat acaccaagat agacatcata gaagttccag acgaaaaagc accagaaaat      120
atgagcgaca aagaaattga gcaagtaaaa gaaaaagaag ccaacgaat actagccaaa       180 atcaaaccac aatcaacagt cattacatta gaaatacaag gaaagatgct atcttccgaa      240
ggattggccc aagaattgaa ccaacgcatg acccaagggc aaagcgactt tgtattcgtc      300
attggcggat caaacggcct gcacaaggac gtcttacaac gtagtaacta cgcactatca      360
ttcagcaaaa tgcattccc acatcaaatg atgcgggttg tgttaattga gcaagtgtat       420
agagcattta agattatgcg tggagaagca tatcataaat gatgcggttt tttcagccgc      480
ttcataaagg gattttgaat gtatcagaac atatgaggtt tatgtgaatt gctgttatgt      540
ttttaagaag cttatcataa gtaatgaggt tcatgatttt tgacatagtt agcctccgca      600
gtctttcatt tcaagtaaat aatagcgaaa tattctttat actgaatact tatagtgaag      660
caaagttcta gctttgagaa aattcttttct gcaactaaat atagtaaatt acggtaaaat    720
ataaataagt acatattgaa gaaaatgaga cataatatat tttataatag gagggaattt      780
caaatgatag acaactttat gcaggtcctt aaattaatta agagaaacg taccaataat       840 gtagttaaaa atctgattg gataaaggt gatctatata aactttagt ccatgataag         900 ttacccaagc agttaaaagt gcatataaaa gaagataaat attcagttgt agggaaggtt      960
gctactggga actatagtaa agttccttgg atttcaatat atgatgagaa tataacaaaa     1020
gaaacaaagg atggatatta tttggtatat ctttttcatc cggaaggaga aggcatatac     1080
ttatctttga atcaaggatg gtcaaagata agtgatatgt tccgcgggga ta             1132
```

<210> SEQ ID NO 31
<211> LENGTH: 1133
<212> TYPE: DNA
<213> ORGANISM: Artificial Sequence
<220> FEATURE:
<223> OTHER INFORMATION: Staphylococcus aureus

<400> SEQUENCE: 31

```
agctgtaggg aaactaaaag agaaatattg gaagcaagcc atagcagaat atgaaaaacg       60
tttaggccca tacaccaaga tagacatcat agaagttcca gacgaaaaag caccagaaaa      120
tatgagcgac aaagaaattg agcaagtaaa agaaaaagaa ggccaacgaa tactagccaa      180
aatcaaacca caatcaacag tcattacatt agaaatacaa ggaaagatgc tatcttccga      240
aggattggcc caagaattga accaacgcat gacccaaggg caaagcgact tgtattcgt      300
```

```
cattggcgga tcaaacggcc tgcacaagga cgtcttacaa cgtagtaact acgcactatc    360
attcagcaaa atgacattcc cacatcaaat gatgcgggtt gtgttaattg agcaagtgta    420
tagagcattt aagattatgc gtggagaagc atatcataaa tgatgcggtt ttttcagccg    480
cttcataaag ggattttgaa tgtatcagaa catatgaggt ttatgtgaat tgctgttatg    540
tttttaagaa gcttatcata agtaatgagg ttcatgattt tgacatagt  tagcctccgc    600 agtctttcat ttcaagtaaa taatagcgaa atattcttta tactgaatac ttatagtgaa    660
gcaaagttct agctttgaga aaattctttc tgcaactaaa tatagtaaat tacggtaaaa    720
tataaataag tacatattga agaaaatgag acataatata ttttataata ggagggaatt    780
tcaaatgata gacaacttta tgcaggtcct taaattaatt aaagagaaac gtaccaataa    840
tgtagttaaa aaatctgatt gggataaagg tgatctatat aaaactttag tccatgataa    900
gttacccaag cagttaaaag tgcatataaa agaagataaa tattcagttg tagggaaggt    960
tgctactggg aactatagta agttccttg  gatttcaata tatgatgaga atataacaaa   1020
agaaacaaag gatggatatt atttggtata tcttttttcat ccggaaggag aaggcatata   1080
cttatctttg aatcaaggat ggtcaaagat aagtgatatg tttccgcggg ata           1133

<210> SEQ ID NO 32
<211> LENGTH: 1087
<212> TYPE: DNA
<213> ORGANISM: Artificial Sequence
<220> FEATURE:
<223> OTHER INFORMATION: Staphylococcus aureus

<400> SEQUENCE: 32
actaaaagag aaatattgga agcaagccat agcagaatat gaaaaacgtt taggcccata     60
caccaagata gacatcatag aagttccaga cgaaaaagca ccagaaaata tgagcgacaa    120
agaaattgag caagtaaaag aaaaagaagg ccaacgaata ctagccaaaa tcaaaccaca    180
atcaacagtc attacattag aaatacaagg aaagatgcta tcttccgaag gattggcaca    240
agaattgaac caacgcatga cccagggggca aagcgacttt gtattcgtca ttggcggatc    300
aaacggcctg cacaaggacg tcttacaacg tagtaactac gcactatcat tcagcaaaat    360
gacattccca catcaaatga tgcgggttgt gttaattgag caagtgtata gagcgtttaa    420
gattatgcgt ggagaagcat atcataaatg atgcggtttt ttcagccgct tcataaaggg    480
attttgaatg tatcagaaca tatgaggttt atgtgaattg ctgttatgtt tttaagaagc    540
ttatcataag taatgaggtt catgattttt gacatagtta gcctccgcag tctttcattt    600
caagtaaata atagcgaaat attctttata ctgaatactt atagtgaagc aaagttctag    660
ctttgagaaa attctttctg caactaaata tagtaaatta cggtaaaata taaataagta    720
catattgaag aaaatgagac ataatatatt ttataatagg agggaatttc aaatgataga    780
caactttatg caggtcctta aattaattaa agagaaacgt accaataatg tagttaaaaa    840
atctgattgg gataaaggtg atctatataa aactttagtc catgataagt acccaagca    900 gttaaaagtg catataaaag aagataaata ttcagttgta gggaaggttg ctactgggaa    960
ctatagtaaa gttccttgga tttcaatata tgatgagaat ataacaaaag aaacaaagga   1020
tggatattat ttggtatatc ttttttcatcc ggaaggagaa ggcatatact tatctttgaa   1080
tcaagga                                                             1087

<210> SEQ ID NO 33
<211> LENGTH: 903
```

```
<212> TYPE: DNA
<213> ORGANISM: Artificial Sequence
<220> FEATURE:
<223> OTHER INFORMATION: Staphylococcus aureus

<400> SEQUENCE: 33
caaggaaaga tgctatcttc cgaaggattg cccaagaat tgaaccaacg catgacccaa      60
gggcaaagcg actttgtatt cgtcattggc ggatcaaacg gcctgcacaa ggacgtctta    120
caacgtagta actacgcact atcattcagc aaaatgacat tcccacatca aatgatgcgg    180
gttgtgttaa ttgagcaagt gtatagagca tttaagatta tgcgtggaga agcatatcat    240
aaatgatgcg gttttttcag ccgcttcata aagggatttt gaatgtatca gaacatatga    300
ggtttatgtg aattgctgtt atgttttttaa gaagcttatc ataagtaatg aggttcatga    360 ttttttgacat agttagcctc cgcagtcttt catttcaagt aaataatagc gaaatattct    420
ttatactgaa tacttatagt gaagcaaagt tctagctttg agaaaattct ttctgcaact    480
aaatatagta aattacggta aaatataaat aagtacatat tgaagaaaat gagacataat    540
atattttata ataggaggga atttcaaatg atagacaact ttatgcaggt ccttaaatta    600
attaaagaga acgtaccaa taatgtagtt aaaaaatctg attgggataa aggtgatcta    660
tataaaactt tagtccatga taagttaccc aagcagttaa aagtgcatat aaaagaagat    720
aaatattcag ttgtagggaa ggttgctact gggaactata gtaaagttcc ttggatttca    780
atatatgatg agaatataac aaaagaaaca aaggatggat attatttggt atatcttttt    840
catccggaag gagaaggcat atacttatct ttgaatcaag atggtcaaa gataagtgat    900 atg                                                                  903

<210> SEQ ID NO 34
<211> LENGTH: 1114
<212> TYPE: DNA
<213> ORGANISM: Artificial Sequence
<220> FEATURE:
<223> OTHER INFORMATION: Staphylococcus aureus

<400> SEQUENCE: 34
ggaaactaaa agagaaatat tggaagcaag ccatagcaga atatgaaaaa cgtttaggcc      60
catacaccaa gatagacatc atagaagttc cagacgaaaa agcaccagaa atatgagcg    120 acaaagaaat tgagcaagta aaagaaaaag aaggccaacg aatactagcc aaaatcaaac    180
cacaatcaac agtcattaca ttagaaatac aaggaaagat gctatcttcc gaaggattgg    240
cccaagaatt gaaccaacgc atgacccaag gcaaagcga cttttgtattc gtcattggcg    300 gatcaaacgg cctgcacaag gacgtcttac aacgtagtaa ctacgcacta tcattcagca    360
aaatgacatt cccacatcaa atgatgcggg ttgtgttaat tgagcaagtg tatagagcat    420
ttaagattat gcgtggagaa gcatatcata aatgatgcgg ttttttcagc cgcttcataa    480
agggattttg aatgtatcag aacatatgag gtttatgtga attgctgtta tgttttttaag    540 aagcttatca taagtaatga ggttcatgat ttttgacata gttagcctcc gcagtctttc    600
atttcaagta aataatagcg aaatattctt tatactgaat acttatagtg aagcaaagtt    660
ctagctttga gaaaattctt tctgcaacta aatatagtaa attacggtaa aatataaata    720
agtacatatt gaagaaaatg agacataata tattttataa taggagggaa tttcaaatga    780
tagacaactt tatgcaggtc cttaaattaa ttaaagagaa acgtaccaat aatgtagtta    840
aaaaatctga ttgggataaa ggtgatctat ataaaacttt agtccatgat aagttaccca    900
agcagttaaa agtgcatata aaagaagata aatattcagt tgtagggaag gttgctactg    960
```

| | |
|---|---:|
| ggaactatag taaagttcct tggatttcaa tatatgatga aatataaca aaagaaacaa | 1020 |
| aggatggata ttatttggta tatcttttc atccggaagg agaaggcata tacttatctt | 1080 |
| tgaatcaagg atggtcaaag ataagtgata tgtt | 1114 |

<210> SEQ ID NO 35
<211> LENGTH: 1121
<212> TYPE: DNA
<213> ORGANISM: Artificial Sequence
<220> FEATURE:
<223> OTHER INFORMATION: Staphylococcus aureus

<400> SEQUENCE: 35

| | |
|---|---:|
| ggaaactaaa agagaaatat tggaagcaag ccatagcaga atatgaaaaa cgtttaggcc | 60 |
| catacaccaa gatagacatc atagaagttc cagacgaaaa agcaccagaa aatatgagcg | 120 |
| acaaagaaat tgagcaagta aaagaaaaag aaggccaacg aatactagcc aaaatcaaac | 180 |
| cacaatccac agtcattaca ttagaaatac aggaaagat gctatcttcc gaaggattgg | 240 |
| cccaagaatt gaaccaacgc atgacccaag gcaaagcga ctttgtattc gtcattggcg | 300 |
| gatcaaacgg cctgcacaag gacgtcttac aacgcagtaa ctatgcacta tcatttagca | 360 |
| aaatgacatt cccacatcaa atgatgcggg ttgtgttaat tgaacaagtg tatagagcat | 420 |
| ttaagattat gcgtggagaa gcatatcata atgatgcgg tttttcagc cgcttcataa | 480 |
| agggattttg aatgtatcag aacatatgag gtttatgtga attgctgtta tgtttttaag | 540 |
| aagcttatca taagtaatga ggttcatgat ttttgacata gttagcctcc gcagtctttc | 600 |
| atttcaagta ataatagcg aaatattctt tatactgaat acttatagtg aagcaaagtt | 660 |
| ctagctttga gaaaattctt tctgcaacta aatatagtaa attacggtaa aatataaata | 720 |
| agtacatatt gaagaaaatg agacataata tattttataa taggagggaa tttcaaatga | 780 |
| tagacaactt tatgcaggtc cttaaattaa ttaaagagaa acgtaccaat aatgtagtta | 840 |
| aaaaatctga ttgggataaa ggtgatctat ataaaacttt agtccatgat aagttaccca | 900 |
| agcagttaaa agtgcatata aaagaagata atattcagt tgtagggaag gttgctactg | 960 |
| ggaactatag taaagttcct tggatttcaa tatatgatga aatataaca aaagaaacaa | 1020 |
| aggatggata ttatttggta tatcttttc atccggaagg agaaggcata tacttatctt | 1080 |
| tgaatcaagg atggtcaaag ataagtgata tgtttccgcg g | 1121 |

<210> SEQ ID NO 36
<211> LENGTH: 1121
<212> TYPE: DNA
<213> ORGANISM: Artificial Sequence
<220> FEATURE:
<223> OTHER INFORMATION: Staphylococcus aureus

<400> SEQUENCE: 36

| | |
|---|---:|
| tagctgtagg gaaactaaaa gagaaatatt ggaagcaagc catagcagaa tatgaaaaac | 60 |
| gtttaggccc atacaccaag atagacatca tagaagttcc agacgaaaaa gcaccagaaa | 120 |
| atatgagcga caaagaaatt gagcaagtaa aagaaaaaga aggccaacga atactagcca | 180 |
| aaatcaaacc acaatccaca gtcattacat tagaaataca ggaaagatg ctatcttccg | 240 |
| aaggattggc ccaagaattg aaccaacgca tgacccaagg gcaaagcgac tttgtattcg | 300 |
| tcattggcgg atcaaacggc ctgcacaagg acgtcttaca acgcagtaac tatgcactat | 360 |
| catttagcaa aatgacattc ccacatcaaa tgatgcgggt tgtgttaatt gaacaagtgt | 420 |
| atagagcatt taagattatg cgtggagaag catatcataa atgatgcggt tttttcagcc | 480 |

```
gcttcataaa gggattttga atgtatcaga acatatgagg tttatgtgaa ttgctgttat    540
gtttttaaga agcttatcat aagtaatgag gttcatgatt tttgacatag ttagcctccg    600
cagtctttca tttcaagtaa ataatagcga aatattcttt atactgaata cttatagtga    660
agcaaagttc tagctttgag aaaattcttt ctgcaactaa atatagtaaa ttacggtaaa    720
atataaataa gtacatattg aagaaaatga gacataatat attttataat aggagggaat    780
ttcaaatgat agacaacttt atgcaggtcc ttaaattaat taaagagaaa cgtaccaata    840
atgtagttaa aaaatctgat tgggataaag gtgatctata taaaacttta gtccatgata    900
agttacccaa gcagttaaaa gtgcatataa aagaagataa atattcagtt gtagggaagg    960
ttgctactgg gaactatagt aaagttcctt ggatttcaat atatgatgag aatataacaa   1020
aagaaacaaa ggatggatat tatttggtat atcttttttca tccggaagga gaaggcatat   1080
acttatcttt gaatcaagga tggtcaaaga taagtgatat g                       1121
```

<210> SEQ ID NO 37
<211> LENGTH: 1131
<212> TYPE: DNA
<213> ORGANISM: Artificial Sequence
<220> FEATURE:
<223> OTHER INFORMATION: Staphylococcus aureus

<400> SEQUENCE: 37

```
ctgtagggaa actaaaagag aaatattgga agcaagccat agcagaatat gaaaaacgtt     60
taggcccata caccaagata gacatcatag aagttccaga cgaaaaagca ccagaaaata    120
tgagcgacaa agaaattgag caagtaaaag aaaagaagg ccaacgaata ctagccaaaa    180
tcaaaccaca atccacagtc attacattag aaatacaagg aaagatgcta tcttccgaag    240
gattggccca agaattgaac caacgcatga cccaagggca aagcgacttt gtattcgtca    300
ttggcggatc aaacggcctg cacaaggacg tcttacaacg cagtaactat gcactatcat    360
ttagcaaaat gacattccca catcaaatga tgcgggttgt gttaattgaa caagtgtata    420
gagcatttaa gattatgcgt ggagaagcat atcataaatg atgcggtttt ttcagccgct    480
tcataaaggg attttgaatg tatcagaaca tatgaggttt atgtgaattg ctgttatgtt    540
tttaagaagc ttatcataag taatgaggtt catgattttt gacatagtta gcctccgcag    600
tctttcattt caagtaaata tagcgaaat attctttata ctgaatactt atagtgaagc    660
aaagttctag ctttgagaaa attctttctg caactaaata tagtaaatta cggtaaaata    720
taaataagta catattgaag aaaatgagac ataatatatt ttataatagg agggaatttc    780
aaatgataga caactttatg caggtcctta aattaattaa agagaaacgt accaataatg    840
tagttaaaaa atctgattgg gataaaggtg atctatataa aactttagtc catgataagt    900
tacccaagca gttaaaagtg catataaaag aagataaata ttcagttgta gggaaggttg    960
ctactgggaa ctatagtaaa gttccttgga tttcaatata tgatgagaat ataacaaaag   1020
aaacaaagga tggatattat ttggtatatc ttttttcatcc ggaaggagaa ggcatatact   1080
tatctttgaa tcaaggatgg tcaaagataa gtgatatgtt ccgcgggat a             1131
```

<210> SEQ ID NO 38
<211> LENGTH: 896
<212> TYPE: DNA
<213> ORGANISM: Artificial Sequence
<220> FEATURE:
<223> OTHER INFORMATION: Staphylococcus aureus

<400> SEQUENCE: 38

```
cattagaaat acaaggaaag atgctatctt ccgaaggatt ggcccaagaa ttgaaccaac      60
gcatgaccca agggcaaagc gactttgtat tcgtcattgg cggatcaaac ggcctgcaca     120
aggacgtctt acaacgcagt aactatgcac tatcatttag caaaatgaca ttccccacatc    180
aaatgatgcg ggttgtgtta attgaacaag tgtatagagc atttaagatt atgcgtggag     240
aagcatatca taaatgatgc ggttttttca gccgcttcat aaagggatt ttgaatgtatc     300
agaacatatg aggtttatgt gaattgctgt tatgttttta agaagcttat cataagtaat     360
gaggttcatg attttgaca tagttagcct ccgcagtctt tcatttcaag taaataatag      420
cgaaatattc tttatactga atacttatag tgaagcaaag ttctagcttt gagaaaattc     480
tttctgcaac taaatatagt aaattacggt aaaatataaa taagtacata ttgaagaaaa    540
tgagacataa tatattttat aataggaggg aatttcaaat gatagacaac tttatgcagg    600
tccttaaatt aattaaagag aaacgtacca ataatgtagt taaaaatct gattgggata     660
aaggtgatct atataaaact ttagtccatg ataagttacc caagcagtta aaagtgcata    720
taaaagaaga taaatattca gttgtaggga aggttgctac tgggaactat agtaaagttc    780
cttggattc aatatatgat gagaatataa caaaagaaac aaaggatgga tattatttgg     840
tatatctttt tcatccggaa ggagaaggca tatacttatc tttgaatcaa ggatgg         896
```

<210> SEQ ID NO 39
<211> LENGTH: 1125
<212> TYPE: DNA
<213> ORGANISM: Artificial Sequence
<220> FEATURE:
<223> OTHER INFORMATION: Staphylococcus aureus

<400> SEQUENCE: 39

```
ggaaactaaa agagaaatat tggaagcaag ccatatcaga atatgaaaaa cgtttaggcc      60
catacaccaa gatagacatc atagaagttc cagacgaaaa agcaccagaa atatgagcg     120
acaaagaaat cgagcaagta aagaaaaag aaggccaacg aatactagcc aaaatcaaac     180
cacaatcaac agtcattaca ttagaaatac aaggaaagat gctatcttcc gaaggattgg    240
ctcaagaatt gaaccaacgc atgacccaag gcaaagcga ctttgtattc gttattggcg     300
gatcaaacgg cctgcacaag gacgtcttac aacgcagtaa ctatgcacta tcattcagca    360
aaatgacatt ccacatcag atgatgcggg ttgtgttaat tgagcaagtg tatagagcat     420
ttaagattat gcgtggggaa gcatatcata aatgatgcgg ttttttcagc cgcttcataa    480
agggattttg aatgtatcag aacatatgag gtttatgtga attgctgtta tgttttaag     540
aagcttatca taagtaatga ggttcatgat ttttgacata gttagcctcc gcagtctttc    600
atttcaagta ataatagcg aaatattctt tatactgaat acttatagtg aagcaaagtt    660
ctagctttga gaaaattctt tctgcaacta aatatagtaa attacggtaa aatataaata    720
agtacatatt gaagaaaatg agacataata tattttataa taggagggaa tttcaaatga    780
tagacaactt tatgcaggtc cttaaattaa ttaaagagaa acgtaccaat aatgtagtta    840
aaaatctga ttgggataaa ggtgatctat ataaaacttt agtccatgat aagttaccca     900
agcagttaaa agtgcatata aagaagata aatattcagt tgtagggaag gttgctactg    960
ggaactatag taaagttcct tggatttcaa tatatgatga gaatataaca aaagaaacaa   1020
aggatggata ttatttggta tatcttttc atccggaagg agaaggcata tacttatctt   1080
tgaatcaagg atggtcaaag ataagtgata tgtttccgcg ggata                   1125
```

```
<210> SEQ ID NO 40
<211> LENGTH: 1125
<212> TYPE: DNA
<213> ORGANISM: Artificial Sequence
<220> FEATURE:
<223> OTHER INFORMATION: Staphylococcus aureus

<400> SEQUENCE: 40
ggaaactaaa agagaaatat tggaagcaag ccatagcaga atatgaaaaa cgtttaggcc      60
catacaccaa gatagacatc atagaagttc cagacgaaaa agcaccagaa aatatgagcg     120
acaaagaaat tgagcaagta aaagaaaaag aaggccaacg aatactagcc aaaatcaaac     180
cacaatcaac agtcattaca ttagaaatac aaggaaagat gctatcttcc gaaggattgg     240
cacaagaatt gaaccaacgc atgacccaag ggcaaagcga ctttgtattc gtcattggcg     300
gatcaaacgg cctgcacaag gacgtcttac aacgtagtaa ctacgcacta tcattcagca     360
aaatgacatt cccacatcaa atgatgcggg ttgtgttaat tgagcaagtg tatagagcgt     420
ttaagattat gcgtggagaa gcatatcata atgatgcggg tttttcagc cgcttcataa     480 agggattttg aatgtatcag aacatatgag gtttatgtga attgctgtta tgttttaag     540 aagcttatca taagtaatga ggttcatgat ttttgacata gttagcctcc gcagtctttc     600
atttcaagta ataatagcg aaatattctt tatactgaat acttatagtg aagcaaagtt     660
ctagctttga gaaaattctt tctgcaacta aatatagtaa attacggtaa aatataaata     720
agtacatatt gaagaaatg agacataata tattttataa taggagggaa tttcaaatga     780
tagacaactt tatgcaggtc cttaaattaa ttaaagagaa acgtaccaat aatgtagtta     840
aaaaatctga ttgggataaa ggtgatctat ataaaacttt agtccatgat aagttaccca     900
agcagtaaaa agtgcatata aagaagata atattcagt tgtagggaag ttgctactg     960 ggaactatag taaagttcct tggatttcaa tatatgatga aatataaca aaagaaacaa    1020 aggatggata ttatttggta tatctttttc atccggaagg agaaggcata tacttatctt    1080
tgaatcaagg atggtcaaag ataagtgata tgtttccgcg ggata                    1125

<210> SEQ ID NO 41
<211> LENGTH: 926
<212> TYPE: DNA
<213> ORGANISM: Artificial Sequence
<220> FEATURE:
<223> OTHER INFORMATION: Staphylococcus aureus

<400> SEQUENCE: 41
tacattagaa atacaaggaa agatgctatc ttccgaagga ttggcccaag aattgaacca      60
acgcatgacc caagggcaaa gcgactttgt attcgtcatt ggcggatcaa acggcctgca     120
caaggacgtc ttacaacgca gtaactatgc actatcattt agcaaaatga cattcccaca     180
tcaaatgatg cgggttgtgt taattgaaca agtgtataga gcatttaaga ttatgcgtgg     240
agaagcatat cataaatgat gcggttttt cagccgcttc ataagggat tttgaatgta     300 tcagaacata tgaggtttat gtgaattgct gttatgtttt taagaagctt atcataagta     360
atgaggttca tgatttttga catagttagc ctccgcagtc tttcatttca gtaaataat     420 agcgaaatat tctttatact gaatacttat agtgaagcaa agttctagct ttgagaaaat     480
tctttctgca actaaatata gtaaattacg gtaaaatata ataagtaca tattgaagaa     540 aatgagacat aatatatttt ataataggag ggaatttcaa atgatagaca actttatgca     600
ggtccttaaa ttaattaaag agaaacgtac caataatgta gttaaaaaat ctgattggga     660
taaaggtgat ctatataaaa ctttagtcca tgataagtta cccaagcagt aaaagtgca     720
```

-continued

```
tataaaagaa gataaatatt cagttgtagg gaaggttgct actgggaact atagtaaagt      780
tccttggatt tcaatatatg atgagaatat aacaaaagaa acaaaggatg gatattattt      840
ggtatatctt tttcatccgg aaggagaagg catatactta tctttgaatc aaggatggtc      900
aaagataagt gatatgtttc cgcggg                                           926
```

<210> SEQ ID NO 42
<211> LENGTH: 928
<212> TYPE: DNA
<213> ORGANISM: Artificial Sequence
<220> FEATURE:
<223> OTHER INFORMATION: Staphylococcus aureus

<400> SEQUENCE: 42

```
tacattagaa atacaaggaa agatgctatc ttccgaagga ttggcccaag aattgaacca       60
acgcatgacc caagggcaaa gcgactttgt attcgtcatt ggcggatcaa acggcctgca      120
caaggacgtc ttacaacgca gtaactacgc actatcattc agcaaaatga cattcccaca      180
tcaaatgatg cgggttgtgt taattgaaca agtgtacaga gcatttaaga ttatgcgtgg      240
agaagcatat cataaatgat gcggttttt cagccgcttc ataagggat tttgaatgta       300 tcagaacata tgaggtttat gtgaattgct gttatgtttt taagaagctt atcataagta      360
atgaggttca tgattttga catagttagc ctccgcagtc tttcatttca agtaaataat       420
agcgaaatat tctttatact gaatacttat agtgaagcaa agttctagct ttgagaaaat      480
tctttctgca actaaatata gtaaattacg gtaaaatata aataagtaca tattgaagaa      540
aatgagacat aatatatttt ataataggag ggaatttcaa atgatagaca actttatgca      600
ggtccttaaa ttaattaaag agaaacgtac caataatgta gttaaaaaat ctgattggga      660
taaaggtgat ctatataaaa ctttagtcca tgataagtta cccaagcagt taaaagtgca      720
tataaaagaa gataaatatt cagttgtagg gaaggttgct actgggaact atagtaaagt      780
tccttggatt tcaatatatg atgagaatat aacaaaagaa acaaaggatg gatattattt      840
ggtatatctt tttcatccgg aaggagaagg catatactta tctttgaatc aaggatggtc      900
aaagataagt gatatgtttc cgcgggat                                         928
```

<210> SEQ ID NO 43
<211> LENGTH: 479
<212> TYPE: DNA
<213> ORGANISM: Artificial Sequence
<220> FEATURE:
<223> OTHER INFORMATION: Staphylococcus aureus

<400> SEQUENCE: 43

```
ttcgtcattg gcggatcaaa cggcctgcac aaggacgtct tacaacgcag taactacgca       60
ctatcattca gcaaaatgac attcccacat caaatgatgc gggttgtgtt aattgaacaa      120
gtgtacagag catttaagat tatgcgtgga gaagcgtatc ataaataaaa ctaaaaatta      180
ggttgtgtat aatttaaaaa tttaatgaga tgtggaggaa ttacatatat gaaatattgg      240 attataccctt gcaatatcat acgatgttta tagagtgttt aataaaccat ttttcaacta      300
ttgatgatct agaatatata ataactgtac aaattatatt gattatgaa ctacaattaa       360 attaagaaat tgatgatgaa atttttaaatt taaactaatg gaatcaagaa agaatgaaag      420
gaaatataca atgcctacga ttaataaaag gaagtttatt agattttgtg ttagaaaca       479
```

<210> SEQ ID NO 44
<211> LENGTH: 480

-continued

<212> TYPE: DNA
<213> ORGANISM: Artificial Sequence
<220> FEATURE:
<223> OTHER INFORMATION: Staphylococcus aureus

<400> SEQUENCE: 44

```
ttcgtcattg gcggatcaaa cggcctgcac aaggacgtct tacaacgcag taactacgca      60
ctatcattca gcaaaatgac attcccacat caaatgatgc gggttgtgtt aattgaacaa     120
gtgtacagag catttaagat tatgcgtgga gaagcgtatc ataaataaaa ctaaaaatta     180
ggttgtgtat aatttaaaaa tttaatgaga tgtggaggaa ttacatatat gaaatattgg     240
attataccct gcaatatcat acgatgttta tagagtgttt aataaaccat ttttcaacta     300
ttgatgatct agaatatata ataactgtac aaattatatt gattatggaa ctacaattaa     360
attaagaaat tgatgatgaa atttttaaatt taaactaatg gaatcaagaa agaatgaaag     420
gaaatataac atgcctacga ttaataaaag gaagtttatt agattttgtg ttagaaacag     480
```

<210> SEQ ID NO 45
<211> LENGTH: 480
<212> TYPE: DNA
<213> ORGANISM: Artificial Sequence
<220> FEATURE:
<223> OTHER INFORMATION: Staphylococcus aureus

<400> SEQUENCE: 45

```
ttcgtcattg gcggatcaaa cggcctgcac aaggacgtct tacaacgcag taactacgca      60
ctatcattca gcaaaatgac atccccacat caaatgatgc gggttgtgtt aattgaacaa     120
gtgtacagag catttaagat tatgcgtgga gaagcgtatc ataaataaaa ctaaaaatta     180
ggttgtgtat aatttaaaaa tttaatgaga tgtggaggaa ttacatatat gaaatattgg     240
attataccct gcaatatcat acgatgttta tagagtgttt aataaaccat ttttcaacta     300
ttgatgatct agaatatata ataactgtac aaattatatt gattatggaa ctacaattaa     360
attaagaaat tgatgatgaa atttttaaatt taaactaatg gaatcaagaa agaatgaaag     420
gaaatataca atgcctacga ttaataaaag gaagtttatt agatttgtgt tagaaacagt     480
```

<210> SEQ ID NO 46
<211> LENGTH: 480
<212> TYPE: DNA
<213> ORGANISM: Artificial Sequence
<220> FEATURE:
<223> OTHER INFORMATION: Staphylococcus aureus

<400> SEQUENCE: 46

```
ttcgtcattg gcggatcaaa cggcctgcac aaggacgtct tacaacgcag taactacgca      60
ctatcattca gcaaaatgac attcccacat caaatgatgc gggttgtgtt aattgaacaa     120
gtgtacagag catttaagat tatgcgtgga gaagcgtatc ataaataaaa ctaaaaatta     180
ggttgtgtat aatttaaaaa tttaatgaga tgtggaggaa ttacatatat gaaatattgg     240
attataccct gcaatatcat acgatgttta tagagtgttt aataaaccat ttttcaacta     300
ttgatgatct agaatatata ataactgtac aaattatatt gattatggaa ctacaattaa     360
attaagaaat tgatgatgaa atttttaaatt taaactaatg gaatcaagaa agaatgaaag     420
gaaatataca atgcctacga ttaataaaag gaagtttatt agattttgtg ttagaaacag     480
```

<210> SEQ ID NO 47
<211> LENGTH: 309
<212> TYPE: DNA
<213> ORGANISM: Unknown

```
<220> FEATURE:
<223> OTHER INFORMATION: Staphylococcus aureus
<220> FEATURE:
<221> NAME/KEY: misc_feature
<222> LOCATION: 237
<223> OTHER INFORMATION: n = a, t, c, or g

<400> SEQUENCE: 47
ggcggatcaa acggcctgca caaggacgtc ttacaacgca gtaactacgc actatcattc     60
agcaaaatga cattcccaca tcaaatgatg cgggttgtgt taattgaaca agtgtacaga    120
gcatttaaga ttatgcgtgg agaagcgtat cataaataaa actaaaaatt aggttgtgta    180
taatttaaaa atctaatgag atgtggagga attacatata tgaaatattg gattatncct    240
tgcaatatca tacgatgttt atagagtgtt aataaaacca ttttttcaact attgatgatc    300 tacaatata                                                            309

<210> SEQ ID NO 48
<211> LENGTH: 471
<212> TYPE: DNA
<213> ORGANISM: Artificial Sequence
<220> FEATURE:
<223> OTHER INFORMATION: Staphylococcus aureus

<400> SEQUENCE: 48
ttggcggatc aaacggcctg cacaaggacg tcttacaacg cagtaactac gcactatcat     60
tcagcaaaat gacattccca catcaaatga tgcgggttgt gttaattgaa caagtgtaca    120
gagcatttaa gattatgcgt ggagaagcgt atcataaata aaactaaaaa ttaggttgtg    180
tataatttaa aaatttaatg agatgtggag gaattacata tatgaaatat tggattatac    240
cttgcaatat catacgatgt ttatagagtg tttaataaac cattttttcaa ctattgatga    300 tctagaatat ataataactg tacaaattat attgattatg gaactacaat taaattaaga    360
aattgatgat gaaattttaa atttaaacta atggaatcaa gaaagaatga aggaaatat    420 acaatgccta cgattaataa aaggaagttt attagatttt gtgttagaaa c             471

<210> SEQ ID NO 49
<211> LENGTH: 480
<212> TYPE: DNA
<213> ORGANISM: Artificial Sequence
<220> FEATURE:
<223> OTHER INFORMATION: Staphylococcus aureus

<400> SEQUENCE: 49
ttcgtcattg gcggatcaaa cggcctgcac aaggacgtct tacaacgcag taactacgca     60
ctatcattca gcaaaatgac attcccacat caaatgatgc gggttgtgtt aattgaacaa    120
gtgtacagag catttaagat tatgcgtgga gaagcgtatc ataaataaaa ctaaaaatta    180
ggttgtgtat aatttaaaaa tttaatgaga tgtggaggaa ttacatatat gaaatattgg    240
attataccct gcaatatcat acgatgttta tagagtgttt aataaaccat ttttcaacta    300
ttgatgatct agaatatata ataactgtac aaattatatt gattatgaa ctacaattaa     360 attaagaaat tgatgatgaa attttaaatt taaactaatg gaatcaagaa agaatgaaag    420
gaaatataca atgcctacga ttaataaaag gaagtttatt agattttgtg ttagaaacag    480

<210> SEQ ID NO 50
<211> LENGTH: 480
<212> TYPE: DNA
<213> ORGANISM: Artificial Sequence
<220> FEATURE:
<223> OTHER INFORMATION: Staphylococcus aureus
```

```
<400> SEQUENCE: 50
ttcgtcattg gcggatcaaa cggcctgcac aaggacgtct tacaacgcag taactacgca      60
ctatcattca gcaaaatgac attcccacat caaatgatgc gggttgtgtt aattgaacaa     120
gtgtacagag catttaagat tatgcgtgga gaagcgtatc ataaataaaa ctaaaaatta     180
ggttgtgtat aatttaaaaa tttaatgaga tgtggaggaa ttacatatat gaaatattgg     240
attatacctt gcaatatcat acgatgttta tagagtgttt aataaaccat ttttcaacta     300
ttgatgatct agaatatata ataactgtac aaattatatt gattatggaa ctacaattaa     360
attaagaaat tgatgatgaa attttaaatt taaactaatg gaatcaagaa agaatgaaag     420
gaaatataca atgcctacga ttaataaaag gaagtttatt agattttgtg ttagaaacag     480

<210> SEQ ID NO 51
<211> LENGTH: 480
<212> TYPE: DNA
<213> ORGANISM: Artificial Sequence
<220> FEATURE:
<223> OTHER INFORMATION: Staphylococcus aureus

<400> SEQUENCE: 51
ttcgtcattg gcggatcaaa cggcctgcac aaggacgtct tacaacgcag taactacgca      60
ctatcattca gcaaaatgac attcccacat caaatgatgc gggttgtgtt aattgaacaa     120
gtgtacagag catttaagat tatgcgtgga gaagcgtatc ataaataaaa ctaaaaatta     180
ggttgtgtat aatttaaaaa tttaatgaga tgtggaggaa ttacatatat gaaatattgg     240
attatacctt gcaatatcat acgatgttta tagagtgttt aataaaccat ttttcaacta     300
ttgatgatct agaatatata ataactgtac aaattatatt gattatggaa ctacaattaa     360
attaagaaat tgatgatgaa attttaaatt taaactaatg gaatcaagaa agaatgaaag     420
gaaatataca atgcctacga ttaataaaag gaagtttatt agattttgtg ttagaaacag     480

<210> SEQ ID NO 52
<211> LENGTH: 478
<212> TYPE: DNA
<213> ORGANISM: Artificial Sequence
<220> FEATURE:
<223> OTHER INFORMATION: Staphylococcus aureus

<400> SEQUENCE: 52
ttcgtcattg gcggatcaaa cggcctgcac aaggacgtct tacaacgcag taactacgca      60
ctatcattca gcaaaatgac attcccacat caaatgatgc gggttgtgtt aattgaacaa     120
gtgtacagag catttaagat tatgcgtgga gaagcgtatc ataaataaaa ctaaaaatta     180
ggttgtgtat aatttaaaaa tttaatgaga tgtggaggaa ttacatatat gaaatattgg     240
attatacctt gcaatatcat acgatgttta tagagtgttt aataaaccat ttttcaacta     300
ttgatgatct agaatatata ataactgtac aaattatatt gattatggaa ctacaattaa     360
attaagaaat tgatgatgaa attttaaatt taaactaatg gaatcaagaa agaatgaaag     420
gaaatataca atgcctacga ttaataaaag gaagtttatt agattttgtg ttagaaac      478

<210> SEQ ID NO 53
<211> LENGTH: 479
<212> TYPE: DNA
<213> ORGANISM: Artificial Sequence
<220> FEATURE:
<223> OTHER INFORMATION: Staphylococcus aureus

<400> SEQUENCE: 53
```

```
ttcgtcattg gcggatcaaa cggcctgcac aaggacgtct tacaacgcag taactacgca    60
ctatcattca gcaaaatgac attcccacat caaatgatgc gggttgtgtt aattgaacaa   120
gtgtacagag catttaagat tatgcgtgga gaagcgtatc ataaataaaa ctaaaaatta   180
ggttgtgtat aatttaaaaa tttaatgaga tgtggaggaa ttacatatat gaaatattgg   240
attataccct gcaatatcat acgatgttta tagagtgttt aataaaccat ttttcaacta   300
ttgatgatct agaatatata ataactgtac aaattatatt gattatggaa ctacaattaa   360
attaagaaat tgatgatgaa attttaaatt taaactaatg gaatcaagaa agaatgaaag   420
gaaatataca atgcctacga ttaataaaag gaagtttatt agattttgtg ttagaaaca    479
```

<210> SEQ ID NO 54
<211> LENGTH: 480
<212> TYPE: DNA
<213> ORGANISM: Artificial Sequence
<220> FEATURE:
<223> OTHER INFORMATION: Staphylococcus aureus
<220> FEATURE:
<221> NAME/KEY: misc_feature
<222> LOCATION: 406
<223> OTHER INFORMATION: n = a, t, c, or g

<400> SEQUENCE: 54

```
ttcgtcattg gcggatcaaa cggcctgcac aaggacgtct tacaacgcag taactacgca    60
ctatcattca gcaaaatgac attcccacat caaatgatgc gggttgtgtt aattgaacaa   120
gtgtacagag catttaagat tatgcgtgga gaagcgtatc ataaataaaa ctaaaaatta   180
ggttgtgtat aatttaaaaa tttaatgaga tgtggaggaa ttacatatat gaaatattgg   240
attataccct gcaatatcat acgatgttta tagagtgttt aataaaccat ttttcaacta   300
ttgatgatct agaatatata ataactgtac aaattatatt gattatggaa ctacaattaa   360
attaagaaat tgatgatgaa attttaaatt taaactaatg gaatcncgaa agaatgaaag   420
gaaatataca atgcctacga ttaataaaag gaagtttatt agattttgtg ttagaaacag   480
```

<210> SEQ ID NO 55
<211> LENGTH: 480
<212> TYPE: DNA
<213> ORGANISM: Artificial Sequence
<220> FEATURE:
<223> OTHER INFORMATION: Staphylococcus aureus

<400> SEQUENCE: 55

```
ttcgtcattg gcggatcaaa cggcctgcac aaggacgtct tacaacgcag taactacgca    60
ctatcattca gcaaaatgac attcccacat caaatgatgc gggttgtgtt aattgaacaa   120
gtgtacagag catttaagat tatgcgtgga gaagcgtatc ataaataaaa ctaaaaatta   180
ggttgtgtat aatttaaaaa tttaatgaga tgtggaggaa ttacatatat gaaatattgg   240
attataccct gcaatatcat acgatgttta tagagtgttt aataaaccat ttttcaacta   300
ttgatgatct agaatatata ataactgtac aaattatatt gattatggaa ctacaattaa   360
attaagaaat tgatgatgaa attttaaatt taaactaatg gaatcaagaa agaatgaaag   420
gaaatataca atgcctacga ttaataaaag gaagtttatt agattttgtg ttagaaacag   480
```

<210> SEQ ID NO 56
<211> LENGTH: 1256
<212> TYPE: DNA
<213> ORGANISM: Artificial Sequence
<220> FEATURE:
<223> OTHER INFORMATION: Staphylococcus aureus

<400> SEQUENCE: 56

```
ttcagaaaaa tgattaatgt gtttcaataa aatctctcct tctttgtgaa catattcatt      60
tttatactaa ttaatataat ttccaaaaaa gtttctgttt aaaagtgaaa aatattattt     120
accgtttgac ttaaatcttc aatatatagg tgtttatatg tatcattttg cgccaatttg     180
aataaacggg aatcaagtct gtttctgagt ttatttcaac tttcttatag taaacattgt     240
cttaatatga tgaacttcaa taaaactttc cctatgcccc ataaaatttt ctcaaaatca     300
aaaataacat accttacaac ttttaccgtc gatatcaatt gctcttttct taatttagga     360
ttgctttcaa attttgtact ataacgtgaa actactttc cttctttata attaaaattt     420
actaattcac aatcattttt acttccattt acaaaaacat ccactgtttc taacacaaaa     480
tctaataaac ttccttttat taatcgtagg cattgtatat ttcctttcat tctttcttga     540
ttccattagt ttaaatttaa aatttcatcc atcaatttct taatttaatt gtagttccat     600
aatcaatata atttgtacag ttattatata ttctagatca tcaatagttg aaaaatggtt     660
tattaaacac tctataaaca tcgtatgata ttgcaaggta taatccaata tttcatatat     720
gtaattcctc cacatctcat taaattttta aattatacac aacctaattt ttagtttttat     780
ttatgatacg cttctccacg cataatctta aatgctctgt acacttgttc aattaacaca     840
acccgcatca tttgatgtgg gaatgtcatt ttgctgaatg atagtgcgta gttactgcgt     900
tgtaagacgt ccttgtgcag gccgtttgat ccgccaatga cgaatacaaa gtcgctttgc     960
ccttgggtca tgcgttggtt caattcttgg gccaatcctt cggaagatag catctttcct    1020
tgtatttcta atgtaatgac tgttgattgt ggtttgattt tggctagtat tcgttggcct    1080
tctttttctt ttacttgctc aatttctttg tcgctcatat tttctggtgc ttttcgtct     1140
ggaacttcta tgatgtctat cttggtgtat gggcctaaac gttttcata ttctgctatg     1200
gcttgcttcc aatatttctc ttttagtttc cctacagcta aatggtgat tttcat         1256
```

<210> SEQ ID NO 57
<211> LENGTH: 679
<212> TYPE: DNA
<213> ORGANISM: Artificial Sequence
<220> FEATURE:
<223> OTHER INFORMATION: Staphylococcus aureus

<400> SEQUENCE: 57

```
ataagaggga acagtgtgaa caagttaata acttgtggat aactggaaag ttgataacaa      60
tttggaggac caaacgacat gaaaatcacc attttagctg tagggaaact aaaagagaaa     120
tattggaagc aagccatagc agaatatgaa aaacgtttag gcccatacac caagatagac     180
atcatagaag ttccagacga aaaagcacca gaaaatatga gcgacaaaga aattgagcaa     240
gtaaaagaaa aagaaggcca acgaatacta gccaaaatca aaccacaatc cacagtcatt     300
acattagaaa tacaaggaaa gatgctatct tccgaaggat tggcccaaga attgaaccaa     360
cgcatgaccc aagggcaaag cgactttgta ttcgtcattg gcggatcaaa cggcctgcac     420
aaggacgtct tacaacgcag taactatgca ctatcattta gcaaaatgac attcccacat     480
caaatgatgc gggttgtgtt aattgaacaa gtgtatagag catttaagat tatgcgtgga     540
gaggcttatc ataaataaaa ctaaaaatta gattgtgtat aatttaaaaa tttaatgaga     600
tgtggaggaa ttacatatat gaaatattgg agtatacctt gcaatatcat acgatgttta     660
tagagtgttt aataaaacca                                                 679
```

```
<210> SEQ ID NO 58
<211> LENGTH: 782
<212> TYPE: DNA
<213> ORGANISM: Artificial Sequence
<220> FEATURE:
<223> OTHER INFORMATION: Staphylococcus aureus

<400> SEQUENCE: 58
caatgcccac agagttatcc acaaatacac aggttataca ctaaaaattg ggcatgaatg      60
tcagaaaaat atcaaaaact gcaaagaata ttggtataat aagagggaac agtgtgaaca     120
agttaataac ttgtggataa ctggaaagtt gataacaatt tggaggacca aacgacatga     180
aaatcaccat tttagctgta gggaaactaa aagagaaata ttggaagcaa gccatagcag     240
aatatgaaaa acgtttaggc ccatacacca agatagacat catagaagtt ccagacgaaa     300
aagcaccaga aaatatgagc gacaaagaaa ttgagcaagt aaaagaaaaa gaaggccaac     360
gaatactagc caaaatcaaa ccacaatcaa cagtcattac attagaaata caaggaaaga     420
tgctatcttc cgaaggattg gcccaagaat tgaaccaacg catgacccaa gggcaaagcg     480
actttgtatt cgtcattggc ggatcaaacg gcctgcacaa ggacgtctta caacgcagta     540
actacgcact atcattcagc aaaatgacat tcccacatca aatgatgcgg ttgtgttaa      600 ttgaacaagt gtacagagca tttaagatta tgcgtggaga agcgtatcat aaataaaact     660
aaaaattagg ttgtgtataa tttaaaaatt taatgagatg tggaggaatt acatatatga     720
aatattggat tataccttgc aatatcatac gatgtttata gagtgtttaa taaaccattt     780
tt                                                                    782

<210> SEQ ID NO 59
<211> LENGTH: 1045
<212> TYPE: DNA
<213> ORGANISM: Artificial Sequence
<220> FEATURE:
<223> OTHER INFORMATION: Staphylococcus aureus

<400> SEQUENCE: 59
ccagtttttt gtttaatgaa caaggtaaat tacgagataa tatttgaaga aaacaataaa      60
gtagagatgg atttccatat cctctttagt agcggttttt atctgtaagg tttattaata     120
attaaataaa taggcgggat agttatatat agcttattaa tgaaagaata tgattattaa     180
tttagtatta tattttaata ttaaaaagaa gatatgaaat aattattcat accttccacc     240
ttacaataat tagttttcaa tcgaatatta agattattag tagtcttaaa agttaagact     300
tccttatatt aatgacctaa tttattattt gcctcatgaa ttatcttttt atttctttga     360
tatgtcccaa accacatcgt gatatacact acaataaata ttatgatgaa actaataata     420
ttctcaaagt tcagatggaa ccaacctgct agaatagcga gtgggaagaa taggattatc     480
atcaatataa agtgaactac agtctgtttt gttatactcc aatcggtatc tgtaaatatc     540
aaattaccat aagtaaacaa aattccaatc aatgcccata gtgctacaca tattagcata     600 ataccgctt cattaaagtt ttcataataa attttaccca taaagaaatc tggatatagt      660
ggtacatatt tatcccttga aaaaaataag tgaagtaatg acagaaatca taagaccagt     720
gaacgcacct ttttgaacag cgtggaataa ttttttcata gtgagatgga ccattccatt     780
tgtttctaac ttcaagtgat caatgtaatt tagattgata atttctgatt ttgaaatacg     840
cacgaatatt gaaccgacaa gctcttcaat ttggtaaagt cgctgataaa gttttaaagc     900
tttattattc attgttatcg catacctgtt tatcttctac tatgaactgt gcaatttgtt     960
ctagatcaat tgggtaaaca tgatggttct gttgcaaagt aaaaaaatat agctaaccac    1020
```

```
taatttatca tgtcagtgtt cgctt                                      1045

<210> SEQ ID NO 60
<211> LENGTH: 1118
<212> TYPE: DNA
<213> ORGANISM: Artificial Sequence
<220> FEATURE:
<223> OTHER INFORMATION: Staphylococcus aureus

<400> SEQUENCE: 60
cagagcattt aagattatgc gtggagaagc gtaccacaaa tgatgcggtt ttttatccag    60 tttttgttt aatgaacaag gtaaattacg agataatatt tgaagaaaac aataaagtag   120
agatggattt ccatatcctc tttagtagcg gtttttatct gtaaggttta ttaataatta   180
aataaatagg cgggatagtt atatatagct tattaatgaa agaatatgat tattaattta   240
gtattatatt ttaatattaa aaagaagata tgaaataatt attcatacct tccaccttac   300
aataattagt tttcaatcga atattaagat tattagtagt cttaaaagtt aagacttcct   360
tatattaatg acctaattta ttatttgcct catgaattat ctttttattt ctttgatatg   420
tcccaaacca catcgtgata tacactacaa taaatattat gatgaaacta ataatattct   480
caaagttcag atggaaccaa cctgctagaa tagcgagtgg gaagaatagg attatcatca   540
atataaagtg aactacagtc tgttttgtta tactccaatc ggtatctgta aatatcaaat   600
taccataagt aaacaaaatt ccaatcaatg cccatagtgc tacacatatt agcataataa   660
ccgcttcatt aaagttttca taataaattt tacccataaa agaatctgga tatagtagta   720
catatttatc ccttgaaaaa aataagtgaa gtaatgacag aaatcataag accagtgaac   780 gcacctttttt gaacagcgtg gaataatttt ttcatagtga gatggaccat tccatttgtt   840
tctaacttca agtgatcaat gtaatttaga ttgataattt ctgattttga aatacgcacg   900
aatattgaac cgacaagctc ttcaatttgg taaagtcgct gataaagttt taaagcttta   960
ttattcattg ttatcgcata cctgtttatc ttctactatg aactgtgcaa tttgttctag  1020
atcaattggg taaacatgat ggttctgttg caaagtaaaa aaatatagct aaccactaat  1080
ttatcatgtc agtgttcgct taacttgcta gcatgatg                         1118

<210> SEQ ID NO 61
<211> LENGTH: 1118
<212> TYPE: DNA
<213> ORGANISM: Artificial Sequence
<220> FEATURE:
<223> OTHER INFORMATION: Staphylococcus aureus

<400> SEQUENCE: 61
cagagcattt aagattatgc gtggagaagc gtaccacaaa tgatgcggtt ttttatccag    60 tttttgttt aatgaacaag gtaaattacg agataatatt tgaagaaaac aataaagtag   120
agatggattt ccatatcctc tttagtagcg gtttttatct gtaaggttta ttaataatta   180
aataaatagg cgggatagtt atatatagct tattaatgaa agaatatgat tattaattta   240
gtattatatt ttaatattaa aaagaagata tgaaataatt attcatacct tccaccttac   300
aataattagt tttcaatcga atattaagat tattagtagt cttaaaagtt aagacttcct   360
tatattaatg acctaattta ttatttgcct catgaattat ctttttattt ctttgatatg   420
tcccaaacca catcgtgata tacactacaa taaatattat gatgaaacta ataatattct   480
caaagttcag atggaaccaa cctgctagaa tagcgagtgg gaagaatagg attatcatca   540
atataaagtg aactacagtc tgttttgtta tactccaatc ggtatctgta aatatcaaat   600
```

| | | |
|---|---|---|
| taccataagt aaacaaaatt ccaatcaatg cccatagtgc tacacatatt agcataataa | 660 | |
| ccgcttcatt aaagttttca taataaattt tacccataaa agaatctgga tatagtagta | 720 | |
| catatttatc ccttgaaaaa aataagtgaa gtaatgacag aaatcataag accagtgaac | 780 | |
| gcacctttt gaacagcgtg gaataatttt ttcatagtga gatggaccat tccatttgtt | 840 | |
| tctaacttca agtgatcaat gtaatttaga ttgataattt ctgattttga aatacgcacg | 900 | |
| aatattgaac cgacaagctc ttcaatttgg taaagtcgct gataaagttt taaagctta | 960 | |
| ttattcattg ttatcgcata cctgtttatc ttctactatg aactgtgcaa tttgttctag | 1020 | |
| atcaattggg taaacatgat ggttctgttg caaagtaaaa aaatatagct aaccactaat | 1080 | |
| ttatcatgtc agtgttcgct taacttgcta gcatgatg | 1118 | |

<210> SEQ ID NO 62
<211> LENGTH: 1113
<212> TYPE: DNA
<213> ORGANISM: Artificial Sequence
<220> FEATURE:
<223> OTHER INFORMATION: Staphylococcus aureus

<400> SEQUENCE: 62

| | | |
|---|---|---|
| agcatttaag attatgcgtg gagaagcgta ccacaaatga tgcggttttt tatccagttt | 60 | |
| tttgtttaat gaacaaggta aattacgaga taatatttga agaaaacaat aaagtagaga | 120 | |
| tggatttcca tatcctcttt agtagcggtt tttatctgta aggtttatta ataattaaat | 180 | |
| aaataggcgg gatagttata tatagcttat taatgaaaga atatgattat taatttagta | 240 | |
| ttatattta atattaaaaa gaagatatga ataattatt catacctcc accttacaat | 300 | |
| aattagttt caatcgaata ttaagattat tagtagtctt aaaagttaag acttccttat | 360 | |
| attaatgacc taatttatta tttgcctcat gaattatctt tttatttctt tgatatgtcc | 420 | |
| caaaccacat cgtgatatac actacaataa atattatgat gaaactaata atattctcaa | 480 | |
| agttcagatg gaaccaacct gctagaatag cgagtgggaa gaataggatt atcatcaata | 540 | |
| taaagtgaac tacagtctgt tttgttatac tccaatcggt atctgtaaat atcaaattac | 600 | |
| cataagtaaa caaaattcca atcaatgccc atagtgctac acatattagc ataataaccg | 660 | |
| cttcattaaa gttttcataa taaatttac ccataaaaga atctggatat agtggtacat | 720 | |
| atttatccct tgaaaaaaat aagtgaagta atgacagaaa tcataagacc agtgaacgca | 780 | |
| ccttttgaa cagcgtggaa taatttttc atagtgagat ggaccattcc atttgtttct | 840 | |
| aacttcaagt gatcaatgta atttagattg ataatttctg attttgaaat acgcacgaat | 900 | |
| attgaaccga caagctcttc aatttggtaa agtcgctgat aaagttttaa agctttatta | 960 | |
| ttcattgtta tcgcatacct gtttatcttc tactatgaac tgtgcaattt gttctagatc | 1020 | |
| aatgggtaa acatgatggt tctgttgcaa agtaaaaaaa tatagctaac cactaattta | 1080 | |
| tcatgtcagt gttcgcttaa cttgctagca tga | 1113 | |

<210> SEQ ID NO 63
<211> LENGTH: 2153
<212> TYPE: DNA
<213> ORGANISM: Artificial Sequence
<220> FEATURE:
<223> OTHER INFORMATION: Staphylococcus aureus

<400> SEQUENCE: 63

| | | |
|---|---|---|
| ctgtagggaa actaaaagag aaatactgga agcaagccat agcagaatat gaaaaacgtt | 60 | |
| taggcccata caccaagata gacatcatag aagttccaga cgaaaaagca ccagaaaata | 120 | |

```
tgagcgacaa agaaatcgag caagtaaaag aaaagaagg ccaacgaata ctagccaaaa        180
tcaaaccaca atccacagtc attacattag aaatacaagg aaagatgcta tcttccgaag        240
gattggccca agaattgaac caacgcatga cccaagggca aagcgacttt gtattcgtca        300
ttggcggatc aaacggcctg cacaaggacg tcttacaacg cagtaactac gcactatcat        360
tcagcaaaat gacattccca catcaaatga tgcgggttgt gttaattgaa caagtgtaca        420
gagcatttaa gattatgcgt ggagaagcgt accacaaatg atgcggtttt ttatccagtt        480
ttttgtttaa tgaacaaggt aaattacgag ataatatttg aagaaaacaa taaagtagag        540
atggatttcc atatcctctt tagtagcggt ttttatctgt aaggtttatt aataattaaa        600
taaataggcg ggatagttat atatagctta ttaatgaaag aatatgatta ttaatttagt        660
attatatttt aatattaaaa agaagatatg aaataattat tcataccttc caccttacaa        720
taattagttt tcaatcgaat attaagatta ttagtagtct taaaagttaa gacttcctta        780
tattaatgac ctaattttatt atttgcctca tgaattatct ttttatttct ttgatatgtc        840
ccaaaccaca tcgtgatata cactacaata aatattatga tgaaactaat aatattctca        900
aagttcagat ggaaccaacc tgctagaata gcgagtggga agaataggat tatcatcaat        960
ataaagtgaa ctacagtctg ttttgttata ctccaatcgg tatctgtaaa tatcaaatta       1020
ccataagtaa acaaaattcc aatcaatgcc catagtgcta cacatattag cataataacc       1080
gcttcattaa agttttcata ataaattta cccataaaag aatctggata tagtggtaca       1140
tatttatccc ttgaaaaaa taagtgaagt aatgacagaa atcataagac cagtgaacgc       1200 accttttga acagcgtgga ataattttt catagtgaga tggaccattc catttgtttc       1260
taacttcaag tgatcaatgt aatttagatt gataatttct gattttgaaa tacgcacgaa       1320
tattgaaccg acaagctctt caatttggta aagtcgctga taaagttta aagctttatt       1380 attcattgtt atcgcatacc tgtttatctt ctactatgaa ctgtgcaatt tgttctagat       1440
caattgggta acatgatgg ttctgttgca aagtaaaaaa atatagctaa ccactaattt       1500
atcatgtcag tgttcgctta acttgctagc atgatgctaa tttcgtggca tggcgaaaat       1560
ccgtagatct gatgagacct gcggttcttt ttatatagag cgtaaataca ttcaatacct       1620
tttaaagtat tctttgctgt attgatactt tgataccttg tctttcttac tttaatatga       1680
cggtgatctt gctcaatgag gttattcaaa tatttcgatg tacaatgaca gtcaggttta       1740
agtttaaaag ctttaattac tttagccatt gctaccttcg ttgaaggtgc ctgatctgta       1800
attacctttt gaggtttacc aaattgttta atgagacgtt taataaacgc atatgctgaa       1860
tgattatctc gttgcttacg caaccaaata tctaatgtat gtccctctgc atcaatggca       1920
cgatataaat agctccattt tccttttatt ttgatgtacg tctcatcaat acgccatttg       1980
taataagctt ttttatgctt tttcttccaa atttgatata aaattggggc atattcttga       2040
acccaacggt agaccgttga atgatgaacg tttacaccac gtccccttaa tatttcagat       2100
atatcacgat aactcaatgc atatcttaga tagtagccaa cggctacagt gat             2153
```

<210> SEQ ID NO 64
<211> LENGTH: 2122
<212> TYPE: DNA
<213> ORGANISM: Artificial Sequence
<220> FEATURE:
<223> OTHER INFORMATION: Staphylococcus aureus

<400> SEQUENCE: 64

```
ggaaactaaa agagaaatat tggaagcaag ccatagcaga atatgaaaaa cgtttaggcc         60
```

```
catacaccaa gatagacatc atagaagttc cagacgaaaa agcaccagaa aatatgagcg      120
acaaagaaat tgagcaagta aagaaaaag aaggccaacg aatactagcc aaaatcaaac       180
cacaatcaac agtcattaca ttagaaatac aaggaaagat gctatcttcc gaaggattgg      240
cccaagaatt gaaccaacgc atgacccaag gcaaagcga ctttgtattc gtcattggcg       300
gatcaaacgg cctgcacaag gacgtcttac aacgcagtaa ctacgcacta tcattcagca     360
aaatgacatt cccacatcaa atgatgcggg ttgtgttaat tgaacaagtg tacagagcat     420
ttaagattat gcgtggagaa gcgtaccaca aatgatgcgg ttttttatcc agttttttgt     480
ttaatgaaca aggtaaatta cgagataata tttgaagaaa acaataaagt agagatggat     540
ttccatatcc tctttagtag cggtttttat ctgtaaggtt tattaataat taaataaata    600
ggcgggatag ttatatatag cttattaatg aaagaatatg attattaatt tagtattata    660
ttttaatatt aaaagaaga tatgaaataa ttattcatac cttccacctt acaataatta     720 gtttcaatc gaatattaag attattagta gtcttaaaag ttaagacttc cttatattaa     780
tgacctaatt tattatttgc ctcatgaatt atctttttat ttctttgata tgtcccaaac    840
cacatcgtga tatacactac aataaatatt atgatgaaac taataatatt ctcaaagttc    900
agatggaacc aacctgctag aatagcgagt gggaagaata ggattatcat caatataaag    960
tgaactacag tctgttttgt tatactccaa tcggtatctg taaatatcaa attaccataa    1020
gtaaacaaaa ttccaatcaa tgcccatagt gctacacata ttagcataat aaccgcttca    1080 ttaaagttttt cataataaat tttacccata aagaatctg gatatagtgg tacatattta   1140
tcccttgaaa aaataagtg aagtaatgac agaaatcata agaccagtga acgcaccttt    1200
ttgaacagcg tggaataatt ttttcatagt gagatggacc attccatttg tttctaactt    1260
caagtgatca atgtaattta gattgataat ttctgatttt gaaatacgca cgaatattga    1320
accgacaagc tcttcaattt ggtaaagtcg ctgataaagt tttaaagctt tattattcat    1380
tgttatcgca tacctgttta tcttctacta tgaactgtgc aatttgttct agatcaattg    1440
ggtaaacatg atggttctgt tgcaaagtaa aaaaatatag ctaaccacta atttatcatg    1500
tcagtgttcg cttaacttgc tagcatgatg ctaatttcgt ggcatggcga aaatccgtag    1560
atctgatgag acctgcggtt ctttttatat agagcgtaaa tacattcaat accttttaaa    1620
gtattctttg ctgtattgat actttgatac cttgtctttc ttactttaat atgacggtga    1680
tcttgctcaa tgaggttatt cagatatttc gatgtacaat gacagtcagg tttaagttta    1740
aaagctttaa ttactttagc cattgctacc ttcgttgaag gtgcctgatc tgtaattacc    1800
ttttgaggtt taccaaattg tttaatgaga cgtttgataa acgcatatgc tgaatgatta    1860
tctcgttgct tacgcaacca aatatctaat gtatgtccct ctgcatcaat ggcacgatat    1920
aaatagctcc attttccttt tattttgatg tacgtctcat caatacgcca tttgtaataa    1980
gcttttttat gcttttttctt ccaaatttga tacaaaattg gggcatattc ttgaacccaa    2040
cggtagaccg ttgaatgatg aacgtttaca ccacgttccc ttaatatttc agatatatca    2100
cgataactca atgtatatct ta                                              2122
```

<210> SEQ ID NO 65
<211> LENGTH: 737
<212> TYPE: DNA
<213> ORGANISM: Artificial Sequence
<220> FEATURE:
<223> OTHER INFORMATION: Staphylococcus aureus

<400> SEQUENCE: 65

```
tttaagatta tgcgtggaga agcatatcat aaatgatgcg gttatttcag ccgtaatttt      60
ataatataaa gcagagttta ttaaattta atgattactt tttattaaga attaattcta      120
gttgatatat tataatgtga aacacaaaat aataatttgt aattgttagt ttataggcat     180
ctgtatttgg aatttttgt agactattta aaaaatagtg tatataagta ttgagttcat      240
gtattaactg tcttttttca tcgttcatca agtataagga tgtagagatt tgttggataa     300
tttcttcgga tgtttttaaa attatcatta aattagatgg tatctgatct tgagttttgt    360
ttttagtgta tgtatatttt aaaaaattt tgattgttgt tatttgactc tcttttaatt     420
tgacaccctc atcaataaat gtgttaaata tatcttcatt tgtacttaaa tcatcaaaat    480
ttgccaacaa atatttgaac gtctctaaat cattatgttt gagttccgtt ttgctattcc    540
ataattccaa accatttggt agaaagccca agctgtgatt ttgatctccc catatagctg   600
aatttaaatc agtgagttga ttaattttt caacacagaa atgtaatttt ggaatgagga    660
atcgaagttg ttcttctact tgctgtactt ttcttttgtt ttcaataaaa tttctacacc   720
atactgttat caaaccg                                                   737
```

<210> SEQ ID NO 66
<211> LENGTH: 1592
<212> TYPE: DNA
<213> ORGANISM: Artificial Sequence
<220> FEATURE:
<223> OTHER INFORMATION: Staphylococcus aureus

<400> SEQUENCE: 66

```
aactaaaaga gaaatattgg aagcaagcca tagcagaata tgaaaaacgt ttaggcccat    60
acaccaagat agacatcata gaagttccag acgaaaaagc accagaaaat atgagtgaca   120
aagaaattga gcaagtaaaa gaaaagaag gccaacgaat actagccaaa atcaaaccac    180
aatccacagt cattacatta gaaatacaag gaaagatgct atcttccgaa ggattggccc    240
aagaattgaa ccaacgcatg acccaagggc aaagcgactt tgttttcgtc attggcggat    300
caaacggcct gcacaaggac gtcttacaac gcagtaacta cgcactatca ttcagcaaaa   360
tgacattccc acatcaaatg atgcgggttg tgttaattga acaagtgtac agagcattta   420
agattatgcg aggagaagca tcataaat gatgcggtta tttcagccgt aatttttataa   480 tataaagcag agtttattaa attttaatga ttactttta ttaagaatta attctagttg    540
atatattata atgtgaaaca caaataataa atttgtaatt gttagtttat aggcatctgt   600
atttggaatt ttttgtagac tatttaaaaa atagtgtata taagtattga gttcatgtat   660
taactgtctt ttttcatcgt tcatcaagta taaggatgta gagatttgtt ggataattc    720 ttcggatgtt tttaaaatta tcattaaatt agatggtatc tgatcttgag ttttgttttt   780
agtgtatgta tattttaaaa aatttttgat tgttgttatt tgactctctt ttaatttgac   840
accctcatca ataaatgtgt taaatatatc ttcatttgta cttaaatcat caaaatttgc    900
caacaaatat ttgaacgtct ctaaatcatt atgtttgagt tccgttttgc tattccataa    960
ttccaaacca tttggtagaa agcccaagct gtgattttga tctccccata tagctgaatt   1020
taaatcagtg agttgattaa ttttttcaac acagaaatgt aatttggaa tgaggaatcg   1080 aagttgttct tctacttgct gtactttct tttgttttca ataaaatttc tacaccatac   1140
tgttatcaaa ccgccaatta ttgtgcacaa tcctccaatg attgtagata aaattgacaa  1200
tatattacac acctttctta gaggtttatt aacatctatt tttgaattta aaattattac   1260
tttggtagcg ttataaccta tttaacagat tagagaaaaa ttgaatgatc gattgaagaa  1320
```

| | |
|---|---|
| tttccaaaat accgtcccat atgcgttgaa ggagatttct attttcttct gtattcaaat | 1380 |
| ctttggcttt atcctttgct ttattcaata aatcatctga gttttttca atattttta | 1440 |
| atacatcttt ggcattttgt ttaaatactt taggatcgga agttagggca ttagagtttg | 1500 |
| ccacattaat catattatta ttaatcattt gaatttgatt atctgataat atctctgata | 1560 |
| acctacgctc atcgaggact ttattaacag tg | 1592 |

<210> SEQ ID NO 67
<211> LENGTH: 730
<212> TYPE: DNA
<213> ORGANISM: Artificial Sequence
<220> FEATURE:
<223> OTHER INFORMATION: Staphylococcus aureus

<400> SEQUENCE: 67

| | |
|---|---|
| agcatttaag attatgcgtg gagaagcata tcataaatga tgcggttatt tcagccgtaa | 60 |
| ttttataata taaagcagag tttattaaat tttaatgatt acttttatt aagaattaat | 120 |
| tctagttgat atattataat gtgaaacaca aaataataat ttgtaattgt tagtttatag | 180 |
| gcatctgtat ttggaattt ttgtagacta tttaaaaaat agtgtatata agtattgagt | 240 |
| tcatgtatta actgtctttt ttcatcgttc atcaagtata aggatgtaga gatttgttgg | 300 |
| ataatttctt cggatgtttt taaaattatc attaaattag atggtatctg atcttgagtt | 360 |
| ttgtttttag tgtatgtata ttttaaaaaa ttttgattg ttgttatttg actctctttt | 420 |
| aatttgacac cctcatcaat aaatgtgtta aatatatctt catttgtact taaatcatca | 480 |
| aaatttgcca acaaatattt gaacgtctct aaatcattat gtttgagttc cgttttgcta | 540 |
| ttccataatt ccaaaccatt tggtagaaag cccaagctgt gattttgatc tccccatata | 600 |
| gctgaattta aatcagtgag ttgattaatt ttttcaacac agaaatgtaa ttttggaatg | 660 |
| aggaatcgaa gttgttcttc tacttgctgt acttttcttt tgttttcaat aaaatttcta | 720 |
| caccatactg | 730 |

<210> SEQ ID NO 68
<211> LENGTH: 1696
<212> TYPE: DNA
<213> ORGANISM: Artificial Sequence
<220> FEATURE:
<223> OTHER INFORMATION: Staphylococcus aureus

<400> SEQUENCE: 68

| | |
|---|---|
| aaagagaaat attggaagca agccatagca gaatatgaaa aacgtttagg cccatacacc | 60 |
| aagatagaca tcatagaagt tccagacgaa aaagcaccag aaaatatgag tgacaaagaa | 120 |
| attgagcaag taaagaaaa agaaggccaa cgaatactag ccaaaatcaa accacaatcc | 180 |
| acagtcatta cattagaaat acaaggaaag atgctatctt ccgaaggatt ggcccaagaa | 240 |
| ttgaaccaac gcatgaccca agggcaaagc gactttgttt tcgtcattgg cggatcaaac | 300 |
| ggcctgcaca aggacgtctt acaacgcagt aactacgcac tatcattcag caaaatgaca | 360 |
| ttcccacatc aaatgatgcg ggttgtgtta attgaacaag tgtacagagc atttaagatt | 420 |
| atgcgaggag aagcatatca taatgatgc ggttatttca gccgtaattt tataatataa | 480 |
| agcagagttt attaaatttt aatgattact ttttattaag aattaattct agttgatata | 540 |
| ttataatgtg aaacacaaaa taataatttg taattgttag tttataggca tctgtatttg | 600 |
| gaattttttg tagactattt aaaaaatagt gtatataagt attgagttca tgtattaact | 660 |
| gtcttttttc atcgttcatc aagtataagg atgtagagat tgttggata atttcttcgg | 720 |

| | |
|---|---|
| atgttttaa aattatcatt aaattagatg gtatctgatc ttgagttttg tttttagtgt | 780 |
| atgtatattt taaaaaattt ttgattgttg ttatttgact ctcttttaat ttgacaccct | 840 |
| catcaataaa tgtgttaaat atatcttcat ttgtacttaa atcatcaaaa tttgccaaca | 900 |
| aatatttgaa cgtctctaaa tcattatgtt tgagttccgt tttgctattc cataattcca | 960 |
| aaccatttgg tagaaagccc aagctgtgat tttgatctcc ccatatagct gaatttaaat | 1020 |
| cagtgagttg attaatttt tcaacacaga aatgtaattt tggaatgagg aatcgaagtt | 1080 |
| gttcttctac ttgctgtact tttcttttgt tttcaataaa atttctacac catactgtta | 1140 |
| tcaaaccgcc aattattgtg cacaatcctc caatgattgt agataaaatt gacaatatat | 1200 |
| tacacacctt tcttagaggt ttattaacat ctattttga atttaaaatt attactttgg | 1260 |
| tagcgttata acctatttaa cagattagag aaaaattgaa tgatcgattg aagaatttcc | 1320 |
| aaaataccgt cccatatgcg ttgaaggaga tttctatttt cttctgtatt caaatctttg | 1380 |
| gctttatcct ttgctttatt caataaatca tctgagtttt tttcaatatt ttttaataca | 1440 |
| tctttggcat tttgtttaaa tactttagga tcggaagtta gggcattaga gtttgccaca | 1500 |
| ttaatcatat tattattaat catttgaatt tgattatctg ataatatctc tgataaccta | 1560 |
| cgctcatcga ggactttatt aacagtgtct tcaacttgtt gttgtgtgat tgtttatct | 1620 |
| tgattttgtt taatatctgc aagttgttct ttaatatctg ctatagaagc atttaaagct | 1680 |
| tcatctgaat acccat | 1696 |

<210> SEQ ID NO 69
<211> LENGTH: 991
<212> TYPE: DNA
<213> ORGANISM: Artificial Sequence
<220> FEATURE:
<223> OTHER INFORMATION: Staphylococcus aureus

<400> SEQUENCE: 69

| | |
|---|---|
| accattttag ctgtagggaa actaaaagag aaatactgga agcaagccat agcagaatat | 60 |
| gaaaaacgtt taggcccata caccaagata gacatcatag aagttccaga cgaaaaagca | 120 |
| ccagaaaata tgaactacaa agaaattgag caagtaaaag aaaagaagg ccaacgaata | 180 |
| ctagccaaaa tcaaaccaca atcaacagtc attacattag aaatacaagg aaagatgcta | 240 |
| tcttccgaag gattggccca agaattgaac caacgcatga cccaagggca aagcgacttt | 300 |
| gtattcgtca ttggcggatc aaacggcctg cacaaggacg tcttacaacg cagtaactac | 360 |
| gcactatcat tcagcaaaat gacattccca catcaaatga tgcgggttgt gttaattgaa | 420 |
| caagtgtaca gagcatttaa gattatgcga ggagaagcgt atcataagtg atggtaaaaa | 480 |
| atatgagtaa gtagatgaag agtgaaaatc agattaatta ataataatgt atcaaattta | 540 |
| aataaggggg tttttaagta tgaatttaag aggtcatgaa aatagactta aatttcatgc | 600 |
| gaaatatgat gtgacaccta tatcacattt aaaattatta gaaggtcaaa agaaagacgg | 660 |
| tgaaggcggc atactgacag atagctatta ctgttttca tacagcttaa aaggtaattc | 720 |
| taaaaaagtt ttaggtacgt ttaattgtgg ttatcatatt gctgaagatt tactaaaatt | 780 |
| atcaaatcaa gataaaattac ctttatttaa cccgtttaaa gtaattaatg aaggtaatca | 840 |
| attgcagggc gtaacgaata aaggtaattt aaatattaat aggcaaagaa aacagtataa | 900 |
| tgaagtggct ttacagcttt caaatgctat taattaatc ataatttgtt atgaggataa | 960 |
| tattaaagaa ccactttcaa cgataaaata c | 991 |

```
<210> SEQ ID NO 70
<211> LENGTH: 1282
<212> TYPE: DNA
<213> ORGANISM: Artificial Sequence
<220> FEATURE:
<223> OTHER INFORMATION: Staphylococcus aureus

<400> SEQUENCE: 70
accattttag ctgtagggaa actaaaagag aaatattgga agcaagccat agcagaatat      60
gaaaaacgtt taggcccata caccaagata gacatcatag aagttccaga cgaaaaagca     120
ccagaaaata tgagcgacaa agaaattgag caagtaaaag aaaaagaagg ccaacgaata     180
ctagccaaaa tcaaaccaca atccacagtc attacattag aaatacaagg aaagatgcta     240
tcttccgaag gattggccca agaattgaac caacgcatga cccaagggca aagcgacttt     300
gtattcgtca ttggcggatc aaacggcctg cacaaggacg tcttacaacg cagtaactat     360
gcactatcat ttagcaaaat gacattccca catcaaatga tgcgggttgt gttaattgaa     420
caagtgtata gagcatttaa gattatgcgt ggagaagcgt accacaaata aaactaaaaa     480
atatgagaaa attattaaat tagctcaaat ctttgaagaa taaaaagtga atattaagtt     540
tgataattta ggtacaagta aagattaaga atttccatta tttaatacat ggtgtgtaaa     600
tcgacttctt tttgtattag atgtttgcag taagcgatgt aaagaagatg ctaataaata     660
tgtgaggaat gattacgata ctagataagc ggctaatgaa attttttaaa gtacatatat     720
agacatattt ttcatttagt aaaattttga atttcacttt gctaagacta gtgtctagaa     780
atttataatg atttattaac acctatttga aacttaagta taataaatga ttcggatttt     840 attttttaata aagacaaact tgaacgtagc aaagtagttt ttatgataaa taataagttt     900
taataatgtg acgcttttat ataagcacat tattatgaac aatgtgaatt gagcatctac     960
aattacatta ataaatatat aaatgatgat ttaaattcac atatatttat aatacacata    1020
ctatatgaaa gttttgatta tccgaataaa tgctaaaatt aataaaataa ttaaaggaat    1080
catacttatt atacgtatac gtttagctac tgaactactg gattcatttg gagattctag    1140
tagttctttt tcaatctcta aatctaaatc agttttgtaa taaccattaa ttcctaatct    1200
ttcatctagc tctgtacttt tttcatcatt tttatctttg ttgatatgtt ccattttctc    1260
gcctcttttt aatcaagtag aa                                             1282

<210> SEQ ID NO 71
<211> LENGTH: 1108
<212> TYPE: DNA
<213> ORGANISM: Artificial Sequence
<220> FEATURE:
<223> OTHER INFORMATION: Staphylococcus aureus

<400> SEQUENCE: 71
accattttag ctgtagggaa actaaaagag aaatattgga agcaagccat agcagaatat      60
gaaaaacgtt taggcccata caccaagata gacatcatag aagttccaga cgaaaaagca     120
ccagaaaata tgagcgacaa agaaattgag caagtaaaag aaaaagaagg ccaacgaata     180
ctagccaaaa tcaaaccaca atccacagtc attacattag aaatacaagg aaagatgcta     240
tcttccgaag gattggccca agaattgaac caacgcatga cccaagggca aagcgacttt     300
gtattcgtca ttggcggatc aaacggcctg cacaaggacg tcttacaacg cagtaactat     360
gcactatcat ttagcaaaat gacattccca catcaaatga tgcgggttgt gttaattgaa     420
caagtgtata gagcatttaa gattatgcgt ggagaagcgt accacaaata aaactaaaaa     480
atatgagaaa attattaaat tagctcaaat ctttgaagaa taaaaagtga atattaagtt     540
```

-continued

```
tgataattta ggtacaagta aagattaaga atttccatta tttaatacat ggtgtgtaaa      600
tcgacttctt tttgtattag atgtttgcag taagcgatgt aaagaagatg ctaataaata      660
tgtgaggaat gattacgata ctagataagc ggctaatgaa attttttaaa gtacatatat      720
agacatattt ttcatttagt aaaattttga atttcacttt gctaagacta gtgtctagaa      780
atttataatg atttattaac acctatttga aacttaagta taataaatga ttcggatttt      840 attttttaata aagacaaact tgaacgtagc aaagtagttt ttatgataaa taataagttt      900
taataatgtg acgcttttat ataagcacat tattatgaac aatgtgaatt gagcatctac      960
aattacatta ataaatatat aaatgatgat ttaaattcac atatatttat aatacacata     1020
ctatatgaaa gttttgatta tccgaataaa tgctaaaatt aataaaataa ttaaaggaat     1080
catacttatt atacgtatac gtttagct                                        1108
```

<210> SEQ ID NO 72
<211> LENGTH: 1530
<212> TYPE: DNA
<213> ORGANISM: Artificial Sequence
<220> FEATURE:
<223> OTHER INFORMATION: Staphylococcus aureus

<400> SEQUENCE: 72

```
ttagctgtag ggaaactaaa agagaaatat tggaagcaag ccatagcaga atatgaaaaa       60
cgtttaggcc catacaccaa gatagacatc atagaagttc cagacgaaaa agcaccagaa      120
aatatgagcg acaaagaaat tgagcaagta aagaaaaag aaggccaacg atactagcc       180 aaaatcaaac cacaatccac agtcattaca ttagaaatac aaggaaagat gctatcttcc      240
gaaggattgg cccaagaatt gaaccaacgc atgacccaag gcaaagcga ctttgtattc       300 gtcattggcg gatcaaacgg cctgcacaag gacgtcttac aacgcagtaa ctatgcacta      360
tcatttagca aaatgacatt cccacatcaa atgatgcggg ttgtgttaat tgaacaagtg      420
tatagagcat ttaagattat gcgtggagaa gcatatcata aatgatgcgg ttttttcagc     480
cgcttcataa agggggggtga tcatatcgga acgtatgagg tttatgagaa ttgctgctat     540
gtttttatga agcgtatcat aaatgatgca gttttttgata atttttttctt tatcagagat    600 tttactaaaa atcccctcaa agtttgtttt tttcaacttc aactttgaag ggaataaata     660
aggaacttat ttatatttat cctttatctc attaatatct atttttttat taataatatt    720
ataaatatta aattctttag aaaagtcact atcactctta ttcttcatac taaacgttat    780
taatctaata atatcagcta ctatttcttt aaattctatt gcatcttctt ttttataagt    840
agcgcctgta tgaacaattt tatttctcat accatagtaa tctttcatat atttttttac     900 acaatttta atttcattag aattatccaa atctagatta tcaattgtct ttaataaatg     960
atcattaaca acattagcat acccacatcc aagcttcttt tttatctctt catcacttaa    1020
attttcatct aatttataat atcttttctaa aaaatttgtg ataaaaactt ctaatgcagt    1080
ctgaatttgt acaattgcta aattatagtc agatttataa aaagaacgtt cacctttttct    1140 catagccaaa acataaatat tgctaggatg attattgaaa atattataat ttttttttaat    1200 atttaataaa tcacttttttt tgatagatga atactgatct tcttctatct ttccaggcat    1260
gtcaatcatg aaaatactca tctctttttat atttccatct atagtatata ttatataata    1320
tggaatactt aatatatccc ctaatgatag ctggtatata ttatgatact gatatttaac    1380
gctaataatt ttaataagat tatttagaca attaaattgc ttattaaaaa ttttcgttag    1440
actattactt ttctttgatt ccctagaagt agaatttgat ttcaattttt taaactgatt    1500
```
gtgcttgatt attgaagtta tttcaacata                                      1530

<210> SEQ ID NO 73
<211> LENGTH: 1256
<212> TYPE: DNA
<213> ORGANISM: Artificial Sequence
<220> FEATURE:
<223> OTHER INFORMATION: Staphylococcus aureus

<400> SEQUENCE: 73
gctgtaggga aactaaaaga gaaatattgg aagcaagcca tagcagaata tgaaaaacgt      60
ttaggcccat acaccaagat agacatcata gaagttccag acgaaaaagc accagaaaat    120
atgagcgaca agaaattga gcaagtaaaa gaaaaagaag gccaacgaat actagccaaa     180
attaaaccac aatccacagt cattacatta gaaatacaag gaaagatgct atcttccgaa    240
ggattggccc aagaattgaa ccaacgcatg acccaagggc aaagcgactt tgtattcgtc    300
attggcggat caaacggcct gcacaaggac gtcttacaac gcagtaacta cgcactatca    360
ttcagcaaaa tgacattccc acatcaaatg atgcgggttg tgttaattga gcaagtgtat    420
agagcattta gattatgcg tggagaagca tcataaat gatgcggttt tttcagccgc       480
ttcataaagg gattttgaat gtatcagaac atatgaggtt tatgtgaatt gctgttatgt    540
ttttaagaag catatcataa gtgatgcggt ttttattaat tagttgctaa aaatgaagt    600
atgcaatatt aattattatt aaattttgat atatttaaag aaagattaag tttagggtga    660
atgaatggct tatcaaagtg aatatgcatt agaaaatgaa gtacttcaac aacttgagga    720
attgaactat gaaagagtaa atatacataa tattaaatta gaaattaatg aatatctcaa    780
agaactagga gtgttgaaaa atgaataagc agacaaatac tccagaacta agatttccag    840
agtttgatga ggaatggaaa aaaggaaat taggtgaagt agtaaattat aaaaatggtg     900
gttcatttga aagtttagtg aaaaaccatg gtgtatataa actcataact cttaaatctg    960
ttaatacaga aggaaagttg tgtaattctg aaaatatat cgatgataaa tgtgttgaaa    1020
cattgtgtaa tgatactta gtaatgatac tgagcgagca agcaccagga ctagttggaa    1080
tgactgcaat tatacctaat aataatgagt atgtactaaa tcaacgagta gcagcactag    1140
tgcctaaaca atttatagat agtcaatttc tatctaagtt aattaataga aaccagaaat    1200
atttcagtgt gagatctgct ggaacaaaag tgaaaaatat ttctaaagga catgta        1256

<210> SEQ ID NO 74
<211> LENGTH: 1032
<212> TYPE: DNA
<213> ORGANISM: Artificial Sequence
<220> FEATURE:
<223> OTHER INFORMATION: Staphylococcus aureus

<400> SEQUENCE: 74
accattttag ctgtagggaa actaaaagag aaatattgga agcaagccat agcagaatat     60
gaaaaacgtt taggcccata caccaagata gacatcatag aagttccaga cgaaaaagca    120
ccagaaaata tgagcgacaa agaaattgag caagtaaaag aaaagaagg ccaacgaata     180
ctagccaaaa ttaaaccaca atccacagtc attacattag aaatacaagg aaagatgcta    240
tcttccgaag gattggccca agaattgaac caacgcatga cccaagggca aagcgactt     300
gtattcgtca ttggcggatc aaacggcctg cacaaggacg tcttacaacg cagtaactac    360
gcactatcat tcagcaaaat gacattccca catcaaatga tgcgggttgt gttaattgag    420
caagtgtata gagcatttaa gattatgcgt ggagaagcat atcataagtg atgcggtttt    480

| | |
|---|---|
| tattaattag ttgctaaaaa atgaagtatg caatattaat tattattaaa ttttgatata | 540 |
| tttaagaaa gattaagttt agggtgaatg aatggcttat caaagtgaat atgcattaga | 600 |
| aaatgaagta cttcaacaac ttgaggaatt gaactatgaa agagtaaata tacataatat | 660 |
| taaattagaa attaatgaat atctcaaaga actaggagtg ttgaaaaatg aataagcaga | 720 |
| caaatactcc agaactaaga tttccagagt ttgatgagga atggaaaaaa aggaaattag | 780 |
| gtgaagtagt aaattataaa aatggtggtt catttgaaag tttagtgaaa aaccatggtg | 840 |
| tatataaact cataactctt aaatctgtta atacagaagg aaagttgtgt aattctggaa | 900 |
| aatatatcga tgataaatgt gttgaaacat tgtgtaatga tactttagta atgatactga | 960 |
| gcgagcaagc accaggacta gttggaatga ctgcaattat acctaataat aatgagtatg | 1020 |
| tactaaatca ac | 1032 |

<210> SEQ ID NO 75
<211> LENGTH: 1116
<212> TYPE: DNA
<213> ORGANISM: Artificial Sequence
<220> FEATURE:
<223> OTHER INFORMATION: Staphylococcus aureus

<400> SEQUENCE: 75

| | |
|---|---|
| accattttag ctgtagggaa actaaaagag aaatattgga agcaagccat agcagaatat | 60 |
| gaaaaacgtt taggcccata caccaagata gacatcatag aagttccaga cgaaaaagca | 120 |
| ccagaaaata tgagcgacaa agaaattgag caagtaaaag aaaaagaagg ccaacgaata | 180 |
| ctagccaaaa ttaaaccaca atccacagtc attacattag aaatacaagg aaagatgcta | 240 |
| tcttccgaag gattggccca agaattgaac caacgcatga cccaagggca aagcgacttt | 300 |
| gtattcgtca ttggcggatc aaacggcctg cacaaggacg tcttacaacg cagtaactac | 360 |
| gcactatcat tcagcaaaat gacattccca catcaaatga tgcgggttgt gttaattgag | 420 |
| caagtgtata gagcatttaa gattatgcgt ggagaagcat atcataaatg atgcggtttt | 480 |
| ttcagccgct tcataaaggg attttgaatg tatcagaaca tatgaggttt atgtgaattg | 540 |
| ctgttatgtt tttaagaagc atatcataaa tgatgcggtt ttttcagccg cttcataaag | 600 |
| ggattttgaa tgtatcagaa catatgaggt ttatgtgaat tgctgttatg tttttaagaa | 660 |
| gcatatcata agtgatgcgg ttttttattaa ttagttgcta aaaaatgaag tatgcaatat | 720 |
| taattattat taaattttga tatatttaaa gaaagattaa gtttagggtg aatgaatggc | 780 |
| ttatcaaagt gaatatgcat tagaaaatga agtacttcaa caacttgagg aattgaacta | 840 |
| tgaaagagta aatatacata atattaaatt agaaattaat gaatatctca agaactagg | 900 |
| agtgttgaaa aatgaataag cagacaaata ctccagaact aagatttcca gagtttgatg | 960 |
| aggaatggaa aaaaggaaa ttaggtgaag tagtaaatta taaaaatggt ggttcatttg | 1020 |
| aaagtttagt gaaaaaccat ggtgtatata aactcataac tcttaaatct gttaatacag | 1080 |
| aaggaaagtt gtgtaattct ggaaaatata tcgatg | 1116 |

<210> SEQ ID NO 76
<211> LENGTH: 1100
<212> TYPE: DNA
<213> ORGANISM: Artificial Sequence
<220> FEATURE:
<223> OTHER INFORMATION: Staphylococcus aureus

<400> SEQUENCE: 76

| | |
|---|---|
| accattttag ctgtagggaa actaaaagag aaatattgga agcaagccat agcagaatat | 60 |

```
gaaaaacgtt taggcccata caccaagata gacatcatag aagttccaga cgaaaaagca      120
ccagaaaata tgagcgacaa agaaattgag caagtaaaag aaaagaagg ccaacgaata       180 ctagccaaaa ttaaaccaca atccacagtc attacattag aaatacaagg aaagatgcta     240
tcttccgaag gattggccca agaattgaac caacgcatga cccaagggca aagcgacttt     300
gtattcgtca ttggcggatc aaacggcctg cacaaggacg tcttacaacg cagtaactac     360
gcactatcat tcagcaaaat gacattccca catcaaatga tgcgggttgt gttaattgag     420
caagtgtata gagcatttaa gattatgcgt ggagaagcgt atcacaaata aaactaaaaa     480
ataagttgta tataacttat tttgaaattg gttaagtata taatatctcc aataaaatgt     540
agttaactta cgataatgct gaactatagc tttgtaaact aaaatgtaaa taattacaat     600
caaattgcaa caatatagtt caagaatgct acaatttgag gacagattga tagcattaat     660 cccttttaaaa tgaagctagg agataactta cattatgatt agtaaacaaa taaaggattt    720
acgaaagcaa cataattata ctcaagaaga gctagctgaa aaattaaata cttcaagaca    780
aacaatttct aaatgggaac aaggtatttc agaaccagac ttaattatgc ttatgcaatt    840
gtcacaatta ttttctgtta gtacagacta tctcattaca ggaagtgaca atattattaa    900
aaaagataat aaaagctatt atgaaatgaa ttttgggca tttatgtctg aaaaatggtg     960
ggtaattatt attatagtaa tcataatttg tggaacaata ggacaaattt ttcaaaacta    1020
atgtaagtat ctctcaaata ttttgggagg ttttattatg aaaatcaaaa aattattaaa    1080
gacattatta attattttat                                                1100
```

<210> SEQ ID NO 77
<211> LENGTH: 1118
<212> TYPE: DNA
<213> ORGANISM: Artificial Sequence
<220> FEATURE:
<223> OTHER INFORMATION: Staphylococcus aureus

<400> SEQUENCE: 77

```
atgaaaatca ccattttagc tgtagggaaa ctaaaagaga atattggaa gcaagccata     60 gcagaatatg aaaaacgttt aggcccatac accaagatag acatcataga agttccagac    120
gaaaaagcac cagaaaatat gagcgacaaa gaaattgagc aagtaaaaga aaagaaggc    180 caacgaatac tagccaaaat caaaccacaa tcaacagtca ttacattaga aatacaagga    240
aagatgctat cttccgaagg attggcccaa gaattgaacc aacgcatgac ccaagggcaa    300
agcgactttg tattcgtcat tggcggatca aacggcctgc acaaggacgt cttacaacgc    360
agtaactacg cactatcatt cagcaaaatg acattccac atcaaatgat gcgggttgtg    420
ttaattgaac aagtgtacag agcatttaag attatgcgtg gagaagcgta tcacaaataa    480
aactaaaaaa taagttgtat ataacttatt tgaaattgg ttaagtatat agtatctcca    540
ataaaatgta gttaacttac gataatgctg aactatagct ttgtaaacta aaatgtaaat    600
aattacaatc aaattgcaac aatatagttc aagaatgcta caatttgagg acagattgat    660
agcattaatc cctttaaaat gaagctagga gataacttac attatgatta gtaaacaaat    720
aaaggattta cgaaagcaac ataattatac tcaagaagag ctagctgaaa aattaaatac    780
ttcaagacaa acaatttcta aatgggaaca aggtatttca gaaccagact taattatgct    840
tatgcaattg tcacaattat ttctgttag tacagactat ctcattacag gaagtgacaa    900
tattattaaa aaagataata aaagctatta tgaaatgaat ttttgggcat ttatgtctga    960
aaaatggtgg gtaattatta ttatagtaat cataatttgt ggaacaatag gacaaatttt    1020
```

| | |
|---|---|
| ttcaaactaa tgtaagtatc tctcaaatat tttgggaggt tttattatga aaatcaaaaa | 1080 |
| attattaaag acattattaa ttattttatt atgttttg | 1118 |

<210> SEQ ID NO 78
<211> LENGTH: 1168
<212> TYPE: DNA
<213> ORGANISM: Artificial Sequence
<220> FEATURE:
<223> OTHER INFORMATION: Staphylococcus aureus

<400> SEQUENCE: 78

| | |
|---|---|
| atgaaaatca ccattttagc tgtagggaaa ctaaaagaga atattggaa gcaagccata | 60 |
| gcagaatatg aaaaacgttt aggcccatac accaagatag acatcataga agttccagac | 120 |
| gaaaaagcac cagaaaatat gagcgacaaa gaaattgagc aagtaaaaga aaagaaggc | 180 |
| caacgaatac tagccaaaat caaaccacaa tcaacagtca ttacattaga aatacaagga | 240 |
| aagatgctat cttccgaagg attggcccaa gaattgaacc aacgcatgac ccaagggcaa | 300 |
| agcgactttg tattcgtcat tggcggatca acggcctgc acaaggacgt cttacaacgc | 360 |
| agtaactacg cactatcatt cagcaaaatg acattcccac atcaaatgat gcgggttgtg | 420 |
| ttaattgaac aagtgtacag agcatttaag attatgcgtg gagaagcgta tcacaaataa | 480 |
| aactaaaaaa taagttgtat ataacttatt ttgaaattgg ttaagtatat agtatctcca | 540 |
| ataaaatgta gttaacttac gataatgctg aactatagct ttgtaaacta aaatgtaaat | 600 |
| aattacaatc aaattgcaac aatatagttc aagaatgcta caatttgagg acagattgat | 660 |
| agcattaatc cctttaaaat gaagctagga gataacttac attatgatta gtaaacaaat | 720 |
| aaaggattta cgaaagcaac ataattatac tcaagaagag ctagctgaaa aattaaatac | 780 |
| ttcaagacaa acaatttcta aatgggaaca aggtatttca gaaccagact taattatgct | 840 |
| tatgcaattg tcacaattat tttctgttag tacagactat ctcattacag gaagtgacaa | 900 |
| tattattaaa aaagataata aaagctatta tgaaatgaat ttttgggcat ttatgtctga | 960 |
| aaaatggtgg gtaattatta ttatagtaat cataatttgt ggaacaatag gacaaatttt | 1020 |
| ttcaaactaa tgtaagtatc tctcaaatat tttgggaggt tttattatga aaatcaaaaa | 1080 |
| attattaaag acattattaa ttattttatt atgttttgta ttgtctgtta ttgtgcaaaa | 1140 |
| tatttcaatg ctatggcata ttgtgagc | 1168 |

<210> SEQ ID NO 79
<211> LENGTH: 1134
<212> TYPE: DNA
<213> ORGANISM: Artificial Sequence
<220> FEATURE:
<223> OTHER INFORMATION: Staphylococcus aureus

<400> SEQUENCE: 79

| | |
|---|---|
| atgaaaatca ccattttagc tgtagggaaa ctaaaagaga atattggaa gcaagccata | 60 |
| gcagaatatg aaaaacgttt aggcccatac accaagatag acatcataga agttccagac | 120 |
| gaaaaagcac cagaaaatat gagcgacaaa gaaattgagc aagtaaaaga aaagaaggc | 180 |
| caacgaatac tagccaaaat caaaccacaa tccacagtca ttacattaga aatacaagga | 240 |
| aagatgctat cttccgaagg attggcccaa gaattgaacc aacgcatgac ccaagggcaa | 300 |
| agcgactttg tattcgtcat tggcggatca acggcctgc acaaggacgt cttacaacgc | 360 |
| agtaactatg cactatcatt tagcaaaatg acattcccac atcaaatgat gcgggttgtg | 420 |
| ttaattgaac aagtgtatag agcatttaag attatgcgtg gagaggcgta tcataaataa | 480 |

-continued

| | |
|---|---:|
| aactaaaaaa cggattgtgt ataatatatt ttaaatataa aaaggattga ttttatgtta | 540 |
| aataaattag aaaatgttag ttataaatca ttcgataatt acactagtga agatgatttg | 600 |
| actaaagtaa atatattttt tggaagaaat gggagtggaa aaagctcatt aagtgaatgg | 660 |
| ttaagaagac tagataatga aaaaagtgtt atctttaata ctggttactt aaaaaataat | 720 |
| attgaagaag ttgaagaaat agatggtgtg aatttggtta ttggagaaga atctataaat | 780 |
| catagtgacc aaattaagca tttaaatagc gctataaata gtttagaaaa ttttattact | 840 |
| cggaaaaata gtgaacttaa gcattcaaaa gaaagaattt acaataaaat gaatatcaga | 900 |
| ctaaatgaag ctagagaaag atttgaaata ggtagtaatg tggttaagca gaagaggaat | 960 |
| gctgacaaag atccagttaa tgcttttat agttggaaga aaatgctaa cgatataatt | 1020 |
| caagagatga ctattgaatc tttagatgaa ttagaagaaa gaataacaag aaaagaagtc | 1080 |
| ttattaaata atataaaaac accaattta gcttttgatt ataatgattt tagt | 1134 |

<210> SEQ ID NO 80
<211> LENGTH: 818
<212> TYPE: DNA
<213> ORGANISM: Artificial Sequence
<220> FEATURE:
<223> OTHER INFORMATION: Staphylococcus aureus

<400> SEQUENCE: 80

| | |
|---|---:|
| aatattggaa gcaagccata gcagaatatg aaaaacgttt aggcccatac accaagatag | 60 |
| acatcataga agttccagac gaaaagcac cagaaaatat gagcgacaaa gaaattgagc | 120 |
| aagtgtatag agcatttaag attatgcgtg gagaagcata tcataaatga tgcggttttt | 180 |
| tcagccgctt cataaaggga ttttgaatgt atcagaacat atgaggttta tgtgaattgc | 240 |
| tgttatgttt ttaagaagct tatcataagt aatgaggttc atgattttg acatagttag | 300 |
| cctccgcagt ctttcatttc aagtaaataa tagcgaaata ttctttatac tgaatactta | 360 |
| tagtgaagca aagttctagc tttgagaaaa ttctttctgc aactaaatat agtaaattac | 420 |
| ggtaaaatat aaataagtac atattgaaga aaatgagaca taatatattt tataatagga | 480 |
| gggaatttca aatgatagac aactttatgc aggtccttaa attaattaaa gagaaacgta | 540 |
| ccaataatgt agtaaaaaaa tctgattggg ataaaggtga tctatataaa actttagtcc | 600 |
| atgataagtt acccaagcag ttaaaagtgc atataaaaga agataaatat tcagttgtag | 660 |
| ggaaggttgc tactgggaac tatagtaaag ttccttggat ttcaatatat gatgagaata | 720 |
| taacaaaaga aacaaaggat ggatattatt tggtatatct ttttcatccg gaaggagaag | 780 |
| gcatatactt atcttgaatc aaggatggtc aaagataa | 818 |

<210> SEQ ID NO 81
<211> LENGTH: 1090
<212> TYPE: DNA
<213> ORGANISM: Artificial Sequence
<220> FEATURE:
<223> OTHER INFORMATION: Staphylococcus aureus

<400> SEQUENCE: 81

| | |
|---|---:|
| atgaaaatca ccatttagc tgtagggaaa ctaaaagaga aatattggaa gcaagccata | 60 |
| gcagaatatg aaaaacgttt aggcccatac accaagatag acatcataga agttccagac | 120 |
| gaaaagcac cagaaaatat gagcgacaaa gaaattgagc aagtaaaaga aaagaaggc | 180 |
| caacgaatac tagccaaaat caaaccacaa tcaacagtca ttacattaga aatacaagga | 240 |
| aagatgctat cttccgaagg attggcccaa gaattgaacc aacgcatgac ccaagggcaa | 300 |

```
agcgactttg tattcgtcat tggcggatca acggcctgc acaaggacgt cttacaacgc    360
agtaactacg cactatcatt cagcaaaatg acattcccac atcaaatgat gcgggttgtg    420
ttaattgaac aagtgtacag agcatttaag attatgcgtg gagaagcata tcataagtga    480
tgcggttttt attaattagt tgctaaaaaa tgaagtatgc aatattaatt attattaaat    540
tttgatatat ttaaagaaag attaagttta gggtgaatga atggcttatc aaagtgaata    600
tgcattagaa aatgaagtac ttcaacaact tgaggaattg aactatgaaa gagtaaatat    660
acataatatt aaattagaaa ttaatgaata tctcaaagaa ctaggagtgt tgaaaaatga    720
ataagcagac aaatactcca gaactaagat ttccagagtt tgatgaggaa tggaaaaaaa    780
ggaaattagg tgaagtagta aattataaaa atggtggttc atttgaaagt ttagtgaaaa    840
accatggtgt atataaactc ataactctta aatctgttaa tacagaagga aagttgtgta    900
attctggaaa atatatcgat gataaatgtg ttgaaacatt gtgtaatgat actttagtaa    960
tgatactgag cgagcaagca ccaggactag ttggaatgac tgcaattata cctaataata   1020
atgagtatgt actaaatcaa cgagtagcag cactagtgcc taaacaattt atagatagtc   1080
aatttctatc                                                          1090

<210> SEQ ID NO 82
<211> LENGTH: 1063
<212> TYPE: DNA
<213> ORGANISM: Artificial Sequence
<220> FEATURE:
<223> OTHER INFORMATION: Staphylococcus aureus

<400> SEQUENCE: 82
atgaaaatca ccattttagc tgtagggaaa ctaaaagaga aatattggaa gcaagccata     60
gcagaatatg aaaaacgttt aggcccatac accaagatag acatcataga agttccagac    120
gaaaaagcac cagaaaatat gagcgacaaa gaaattgagc aagtaaaaga aaagaaggc    180 caacgaatac tagccaaaat caaaccacaa tcaacagtca ttacattaga aatacaagga    240
aagatgctat cttccgaagg attggcccaa gaattgaacc aacgcatgac ccaagggcaa    300
agcgactttg tattcgtcat tggcggatca acggcctgc acaaggacgt cttacaacgc    360
agtaactacg cactatcatt cagcaaaatg acattcccac atcaaatgat gcgggttgtg    420
ttaattgaac aagtgtacag agcatttaag attatgcgtg gagaagcata tcataagtga    480
tgcggttttt attaattagt tgctaaaaaa tgaagtatgc aatattaatt attattaaat    540
tttgatatat ttaaagaaag attaagttta gggtgaatga atggcttatc aaagtgaata    600
tgcattagaa aatgaagtac ttcaacaact tgaggaattg aactatgaaa gagtaaatat    660
acataatatt aaattagaaa ttaatgaata tctcaaagaa ctaggagtgt tgaaaaatga    720
ataagcagac aaatactcca gaactaagat ttccagagtt tgatgaggaa tggaaaaaaa    780
ggaaattagg tgaagtagta aattataaaa atggtggttc atttgaaagt ttagtgaaaa    840
accatggtgt atataaactc ataactctta aatctgttaa tacagaagga aagttgtgta    900
attctggaaa atatatcgat gataaatgtg ttgaaacatt gtgtaatgat actttagtaa    960
tgatactgag cgagcaagca ccaggactag ttggaatgac tgcaattata cctaataata   1020
atgagtatgt actaaatcaa cgagtagcag cactagtgcc taa                     1063

<210> SEQ ID NO 83
<211> LENGTH: 756
<212> TYPE: DNA
<213> ORGANISM: Artificial Sequence
```

<220> FEATURE:
<223> OTHER INFORMATION: Staphylococcus aureus

<400> SEQUENCE: 83

```
tgacattccc acatcaaatg atgcgggttg tgttaattga gcaagtgtat agagcattta      60
agattatgcg tggagaagcg tatcacaaat aaaactaaaa aataggttgc gcataatata     120
attagaaagg aattagacat aaattaggag tccttcacag aatagcgaag gactcccatt     180
aaatatatta tggtgtaaag aaatcacaaa tcaatatata tacttaatac catatattaa     240
cttgtactat tataaagtac gacatcagta ttaggtatca ctttgaacac atgaatttca     300
ttatcacttt tattattcac aaaaaatttt ccaattctca attactgaat tatgtgtata     360
catgttgtta aaaattaata aaggatattt atgtttgttt aaagcatatc acaagtgatg     420
cggtttttta taaagattta cttgttagtg attttgataa aaatgcttaa tactatttca     480
ataatatgta tttaaaaatt agattaatag tatttaactt caaatggcct cgtataaact     540
catagcaaat taacgtaaat caatgaaata aaatgaaaac aatttcaaga atacattata     600
aacataaagt atacaaaaaa taaatgagcg tatttgttta aacgtataca ctcattttta     660
ttaaattaat ttattatatt ttacgattgt tatttatgaa attaacaaat tccattttg      720
atagtgaaat taaaagcttt atcacttatt attgat                                756
```

<210> SEQ ID NO 84
<211> LENGTH: 771
<212> TYPE: DNA
<213> ORGANISM: Artificial Sequence
<220> FEATURE:
<223> OTHER INFORMATION: Staphylococcus aureus

<400> SEQUENCE: 84

```
tgacattccc acatcaaatg atgcgggttg tgttaattga gcaagtgtat agagcattta      60
agattatgcg tggagaagcg tatcacaaat aaaactaaaa aataggttgc gcataatata     120
attagaaagg aattagacat aaattaggag tccttcacag aatagcgaag gactcccatt     180
aaatatatta tggtgtaaag aaatcacaaa tcaatatata tacttaatac catatattaa     240
cttgtactat tataaagtac gacatcagta ttaggtatca ctttgaacac atgaatttca     300
ttatcacttt tattattcac aaaaaatttt ccaattctca attactgaat tatgtgtata     360
catgttgtta aaaattaata aaggatattt atgtttgttt aaagcatatc acaagtgatg     420
cggtttttta taaagattta cttgttagtg attttgataa aaatgcttaa tactatttca     480
ataatatgta tttaaaaatt agattaatag tatttaactt caaatggcct cgtataaact     540
catagcaaat taacgtaaat caatgaaata aaatgaaaac aatttcaaga atacattata     600
aacataaagt atacaaaaaa taaatgagcg tatttgttta aacgtataca ctcattttta     660
ttaaattaat ttattatatt ttacgattgt tatttatgaa attaacaaat tccattttg      720
atagtgaaat taaaagcttt atcacttatt attgataatt ttgactgcat c              771
```

<210> SEQ ID NO 85
<211> LENGTH: 681
<212> TYPE: DNA
<213> ORGANISM: Artificial Sequence
<220> FEATURE:
<223> OTHER INFORMATION: Staphylococcus aureus

<400> SEQUENCE: 85

```
ttcagcaaaa tgacattccc acatcaaatg atgcgggttg tgttaattga acaagtgtac      60
agagcattta agattatgcg tggagaagcg tatcataagt agcggaggag ttttttacct     120
```

```
tgtgacttat cataaagtac gatgtttatg taagtgatta tcattattta agcaggtttt    180
tcaaattaaa taataacaag aataaaatgc acttagcgac attgaaattt attaatctag    240
taaactaata gatttataga aaatttttatt tgcaaggggga taatttttgaa aagtagtatt   300
```

```
tgtgacttat cataaagtac gatgtttatg taagtgatta tcattattta agcaggtttt    180
tcaaattaaa taataacaag aataaaatgc acttagcgac attgaaattt attaatctag    240
taaactaata gatttataga aaattttatt tgcaaggggga taattttgaa aagtagtatt    300
ttctatcttt ccataataca ttgtaattac aacggagggg atattgtgat gaagtgtata    360
gataaaacgt gggttagcta ttataaagaa ttagctgata agttaacaga ttatcaaaat    420
aaacgttatg aattaattag aaatagtgaa ggaagtatat aaaaaaacgg aataaaatt     480 ccctacttta gcaagtgata atgtattgat ggacatagat cctttacaa tatttgcatt     540 atttaataaa aattccatga gagaaactaa taaggtaaaa atattaacag aattagcttc    600
ggaattgaat attaagtcca aaattccgtc agtttttgac agtattccaa cagtcaataa    660
tctgaatgct acatattata a                                              681

<210> SEQ ID NO 86
<211> LENGTH: 1119
<212> TYPE: DNA
<213> ORGANISM: Artificial Sequence
<220> FEATURE:
<223> OTHER INFORMATION: Staphylococcus aureus

<400> SEQUENCE: 86
gacattccca catcaaatga tgcgggttgt gttaattgag caagtgtata gagcatttaa     60
gattatgcgt ggagaggcgt atcataagta aaactaaaaa attctgtatg aggagataat    120
aatttggagg gtgttaaatg gtggacatta aatccacgtt cattcaatat ataagatata    180
tcacgataat tgcgcatata acttaagtag tagctaacag ttgaaattag gccctatcaa    240
attggtttat atctaaaatg attaatatag aatgcttctt tttgtcctta ttaaattata    300
aaagtaactt tgcaatagaa acagttattt cataatcaac agtcattgac gtagctaagt    360
aatgataaat aatcataaat aaaattacag atattgacaa aaaatagtaa atataccaat    420
gaagtttcaa aagaacaatt ccaagaaatt gagaatgtaa ataataaggt caaagaattt    480
tattaagatt tgaaagagta tcaatcaaga aagatgtagt tttttaataa actatttgga    540
aaataattat cataatttaa aaactgacaa tttgcgagac tcataaaatg taataatgga    600
aatagatgta aaatataatt aagggggtgta atatgaagat taatatttat aaatctatt    660 ataattttca ggaaacaaat acaaattttt tagagaatct agaatcttta aatgatgaca    720
attatgaact gcttaatgat aaagaacttg ttagtgattc aaatgaatta aaattaatta    780
gtaaagttta tacgtaaaa aaagacaaaa aactattaga ttggcaatta ttaataaaga    840
atgtatacct agatactgaa gaagatgaca atttatttc agaatccggt catcattttg    900
atgcaatatt atttctcaaa gaagatacta cattacaaaa taatgtatat attataccttt   960 ttggacaagc atatcatgat ataaataatt tgattgatta tgacttcgga attgattttg   1020
cagaaagagc aatcaaaaat gaagacatag ttaataaaaa tgttaatttt tttcaacaaa   1080
acaggcttaa agagattgtt aattatagaa ggaatagtg                          1119

<210> SEQ ID NO 87
<211> LENGTH: 1073
<212> TYPE: DNA
<213> ORGANISM: Artificial Sequence
<220> FEATURE:
<223> OTHER INFORMATION: Staphylococcus aureus

<400> SEQUENCE: 87
tattggaagc aagccatagc agaatatgaa aaacgtttag gcccatacac caagatagac     60
```

```
atcatagaag ttccagacga aaaagcacca gaaaatatga gcgacaaaga aattgagcaa      120
gtaaaagaaa aagaaggcca acgaatacta gccaaaatca aaccacaatc cacagtcatt      180
acattagaaa tacaaggaaa gatgctatct tccgaaggat tggcccaaga attgaaccaa      240
cgcatgaccc aagggcaaag cgactttgta ttcgtcattg gcggatcaaa cggcctgcac      300
aaggacgtct tacaacgcag taactatgca ctatcattta gcaaaatgac attcccacat      360
caaatgatgc gggttgtgtt aattgaacaa gtgtatagag catttaagat tatgcgtgga      420
gaggcgtatc ataagtgatg cttgttagaa tgattttaa caatatgaaa tagctgtgga      480
agcttaaaca atttgtttat ctaagtactt atttaataat tgattgaact gtgattggca      540
ccaggctgtc tggtaaattg agaagttggg ttttggagcg tataatgat agaattaata      600 taaaattcaa tttgaggagt aggagattat gtcgaatata aaaacaacac tagagacgtc      660
cgtaggacta gaaaaagaca acgataagct atttgattat ataactgaat tagagattca      720
aaacacgcct gaaaaccggg aagcaaaagt tgttattgaa gaaaggttac ataaagaata      780
taaatatgaa ttagatcaaa tgacaccaga gtatggaata caaaaaggca gtgttagaat      840
aggtcatgca gatgttgtaa tatttcatga ttctaaagat aaatctcaag agaatattaa      900
aataatagta gagtgtaaaa gaaagaatcg cagggatggt attgaacaat taaaaacata      960
tcttgcaggg tgtgagtctg cagaatacgg cgtttggttt aatggagaag atatagtata     1020
tataaaacga ttgaaaaaag caccacattg gaaaacagta tttaatatac cga            1073

<210> SEQ ID NO 88
<211> LENGTH: 595
<212> TYPE: DNA
<213> ORGANISM: Artificial Sequence
<220> FEATURE:
<223> OTHER INFORMATION: Staphylococcus aureus

<400> SEQUENCE: 88
atgaaaatca ccattttagc tgtagggaaa ctaaaagaga atattggaa gcaagccata       60 gcagaatatg aaaaacgttt aggcccatac accaagatag acatcataga agttccagac      120
gaaaaagcac cagaaaatat gagtgacaaa gaaattgagc aagtaaaaga aaaagaaggc      180
caacgaatac tagccaaaat caaaccacaa tccacagtca ttacattaga atacaagga       240 aagatgctat cttccgaagg attggcccaa gaattgaacc aacgcatgac ccaagggcaa      300
agcgactttg ttttcgtcat tggcggatca aacggcctgc acaaggacgt cttacaacgc      360
agtaactacg cactatcatt cagcaaaatg acattcccac atcaaatgat gcgggttgtg      420
ttaattgaac aagtgtacag agcatttaag attatgcgag gagaagcgta tcacaaataa      480
aactaaaaaa tagattgtgt ataatataaa aggagcggat ttatattaaa actttgaatt      540
caaaaattat tgaagggaa gctaccttag aaattgaatc tatggcaact aatac           595

<210> SEQ ID NO 89
<211> LENGTH: 29
<212> TYPE: DNA
<213> ORGANISM: Artificial Sequence
<220> FEATURE:
<223> OTHER INFORMATION: Staphylococcus aureus

<400> SEQUENCE: 89
gtcaaaaatc atgaacctca ttacttatg                                         29

<210> SEQ ID NO 90
<211> LENGTH: 28
```

```
<212> TYPE: DNA
<213> ORGANISM: Artificial Sequence
<220> FEATURE:
<223> OTHER INFORMATION: Staphylococcus aureus

<400> SEQUENCE: 90
ctatgtcaaa aatcatgaac ctcattac                                          28

<210> SEQ ID NO 91
<211> LENGTH: 23
<212> TYPE: DNA
<213> ORGANISM: Artificial Sequence
<220> FEATURE:
<223> OTHER INFORMATION: Staphylococcus aureus

<400> SEQUENCE: 91
ggaggctaac tatgtcaaaa atc                                               23

<210> SEQ ID NO 92
<211> LENGTH: 28
<212> TYPE: DNA
<213> ORGANISM: Artificial Sequence
<220> FEATURE:
<223> OTHER INFORMATION: Staphylococcus aureus
<220> FEATURE:
<221> NAME/KEY: misc_feature
<222> LOCATION: 27
<223> OTHER INFORMATION: n = a, t, c, or g

<400> SEQUENCE: 92
tcatgaacct cattacttat gataagnt                                          28

<210> SEQ ID NO 93
<211> LENGTH: 21
<212> TYPE: DNA
<213> ORGANISM: Artificial Sequence
<220> FEATURE:
<223> OTHER INFORMATION: Staphylococcus aureus

<400> SEQUENCE: 93
gatagactaa ttatcttcat c                                                 21

<210> SEQ ID NO 94
<211> LENGTH: 21
<212> TYPE: DNA
<213> ORGANISM: Artificial Sequence
<220> FEATURE:
<223> OTHER INFORMATION: Staphylococcus aureus

<400> SEQUENCE: 94
cagactgtgg acaaactgat t                                                 21

<210> SEQ ID NO 95
<211> LENGTH: 20
<212> TYPE: DNA
<213> ORGANISM: Artificial Sequence
<220> FEATURE:
<223> OTHER INFORMATION: Staphylococcus aureus

<400> SEQUENCE: 95
tgagatcatc tacatcttta                                                   20

<210> SEQ ID NO 96
<211> LENGTH: 20
<212> TYPE: DNA
<213> ORGANISM: Artificial Sequence
<220> FEATURE:
<223> OTHER INFORMATION: Staphylococcus aureus
```

```
<400> SEQUENCE: 96
ggatcaaaag ctactaaatc                                               20

<210> SEQ ID NO 97
<211> LENGTH: 20
<212> TYPE: DNA
<213> ORGANISM: Artificial Sequence
<220> FEATURE:
<223> OTHER INFORMATION: Staphylococcus aureus

<400> SEQUENCE: 97
atgctctttg ttttgcagca                                               20

<210> SEQ ID NO 98
<211> LENGTH: 23
<212> TYPE: DNA
<213> ORGANISM: Artificial Sequence
<220> FEATURE:
<223> OTHER INFORMATION: Staphylococcus aureus

<400> SEQUENCE: 98
atgaaagact gcggaggcta act                                           23

<210> SEQ ID NO 99
<211> LENGTH: 19
<212> TYPE: DNA
<213> ORGANISM: Artificial Sequence
<220> FEATURE:
<223> OTHER INFORMATION: Staphylococcus aureus

<400> SEQUENCE: 99
ggatcaaacg gcctgcaca                                                19

<210> SEQ ID NO 100
<211> LENGTH: 19
<212> TYPE: DNA
<213> ORGANISM: Artificial Sequence
<220> FEATURE:
<223> OTHER INFORMATION: Staphylococcus aureus

<400> SEQUENCE: 100
tcattggcgg atcaaacgg                                                19

<210> SEQ ID NO 101
<211> LENGTH: 22
<212> TYPE: DNA
<213> ORGANISM: Artificial Sequence
<220> FEATURE:
<223> OTHER INFORMATION: Staphylococcus aureus

<400> SEQUENCE: 101
acaacgcagt aactacgcac ta                                            22

<210> SEQ ID NO 102
<211> LENGTH: 22
<212> TYPE: DNA
<213> ORGANISM: Artificial Sequence
<220> FEATURE:
<223> OTHER INFORMATION: Staphylococcus aureus

<400> SEQUENCE: 102
taactacgca ctatcattca gc                                            22

<210> SEQ ID NO 103
<211> LENGTH: 22
```

```
<212> TYPE: DNA
<213> ORGANISM: Artificial Sequence
<220> FEATURE:
<223> OTHER INFORMATION: Staphylococcus aureus

<400> SEQUENCE: 103
acatcaaatg atgcgggttg tg                                              22

<210> SEQ ID NO 104
<211> LENGTH: 22
<212> TYPE: DNA
<213> ORGANISM: Artificial Sequence
<220> FEATURE:
<223> OTHER INFORMATION: Staphylococcus aureus

<400> SEQUENCE: 104
tcaaatgatg cgggttgtgt ta                                              22

<210> SEQ ID NO 105
<211> LENGTH: 24
<212> TYPE: DNA
<213> ORGANISM: Artificial Sequence
<220> FEATURE:
<223> OTHER INFORMATION: Staphylococcus aureus

<400> SEQUENCE: 105
caaatgatgc gggttgtgtt aatt                                            24

<210> SEQ ID NO 106
<211> LENGTH: 21
<212> TYPE: DNA
<213> ORGANISM: Artificial Sequence
<220> FEATURE:
<223> OTHER INFORMATION: Staphylococcus aureus

<400> SEQUENCE: 106
atcaaatgat gcgggttgtg t                                               21

<210> SEQ ID NO 107
<211> LENGTH: 20
<212> TYPE: DNA
<213> ORGANISM: Artificial Sequence
<220> FEATURE:
<223> OTHER INFORMATION: Staphylococcus aureus

<400> SEQUENCE: 107
accaaacgac atgaaaatca                                                 20

<210> SEQ ID NO 108
<211> LENGTH: 18
<212> TYPE: DNA
<213> ORGANISM: Artificial Sequence
<220> FEATURE:
<223> OTHER INFORMATION: Staphylococcus aureus

<400> SEQUENCE: 108
gtttgatccg ccaatgac                                                   18

<210> SEQ ID NO 109
<211> LENGTH: 23
<212> TYPE: DNA
<213> ORGANISM: Artificial Sequence
<220> FEATURE:
<223> OTHER INFORMATION: Staphylococcus aureus

<400> SEQUENCE: 109
gaggaccaaa cgacatgaaa atc                                             23
```

<210> SEQ ID NO 110
<211> LENGTH: 23
<212> TYPE: DNA
<213> ORGANISM: Artificial Sequence
<220> FEATURE:
<223> OTHER INFORMATION: Staphylococcus aureus

<400> SEQUENCE: 110
gccaaaatta aaccacaatc cac                                              23

<210> SEQ ID NO 111
<211> LENGTH: 24
<212> TYPE: DNA
<213> ORGANISM: Artificial Sequence
<220> FEATURE:
<223> OTHER INFORMATION: Staphylococcus aureus

<400> SEQUENCE: 111
cattttgctg aatgatagtg cgta                                             24

<210> SEQ ID NO 112
<211> LENGTH: 21
<212> TYPE: DNA
<213> ORGANISM: Artificial Sequence
<220> FEATURE:
<223> OTHER INFORMATION: Staphylococcus aureus

<400> SEQUENCE: 112
aagaattgaa ccaacgcatg a                                                21

<210> SEQ ID NO 113
<211> LENGTH: 21
<212> TYPE: DNA
<213> ORGANISM: Artificial Sequence
<220> FEATURE:
<223> OTHER INFORMATION: Staphylococcus aureus

<400> SEQUENCE: 113
aaacgacatg aaaatcacca t                                                21

<210> SEQ ID NO 114
<211> LENGTH: 21
<212> TYPE: DNA
<213> ORGANISM: Artificial Sequence
<220> FEATURE:
<223> OTHER INFORMATION: Staphylococcus aureus

<400> SEQUENCE: 114
tattgcaggt ttcgatgttg a                                                21

<210> SEQ ID NO 115
<211> LENGTH: 22
<212> TYPE: DNA
<213> ORGANISM: Artificial Sequence
<220> FEATURE:
<223> OTHER INFORMATION: Staphylococcus aureus

<400> SEQUENCE: 115
tgacccatat cgcctaaaat ac                                               22

<210> SEQ ID NO 116
<211> LENGTH: 22
<212> TYPE: DNA
<213> ORGANISM: Artificial Sequence
<220> FEATURE:
<223> OTHER INFORMATION: Staphylococcus aureus -continued

<400> SEQUENCE: 116
aaaggacaac aaggtagcaa ag                                              22

<210> SEQ ID NO 117
<211> LENGTH: 22
<212> TYPE: DNA
<213> ORGANISM: Artificial Sequence
<220> FEATURE:
<223> OTHER INFORMATION: Staphylococcus aureus

<400> SEQUENCE: 117
tctgtggata aacaccttga tg                                              22

<210> SEQ ID NO 118
<211> LENGTH: 23
<212> TYPE: DNA
<213> ORGANISM: Artificial Sequence
<220> FEATURE:
<223> OTHER INFORMATION: Staphylococcus aureus

<400> SEQUENCE: 118
ggcataaatg tcaggaaaat atc                                             23

<210> SEQ ID NO 119
<211> LENGTH: 22
<212> TYPE: DNA
<213> ORGANISM: Artificial Sequence
<220> FEATURE:
<223> OTHER INFORMATION: Staphylococcus aureus

<400> SEQUENCE: 119
gtgggaaatg gctgttgttg ag                                              22

<210> SEQ ID NO 120
<211> LENGTH: 22
<212> TYPE: DNA
<213> ORGANISM: Artificial Sequence
<220> FEATURE:
<223> OTHER INFORMATION: Staphylococcus aureus

<400> SEQUENCE: 120
ttcgttccct ccattaactg tc                                              22

<210> SEQ ID NO 121
<211> LENGTH: 21
<212> TYPE: DNA
<213> ORGANISM: Artificial Sequence
<220> FEATURE:
<223> OTHER INFORMATION: Staphylococcus aureus

<400> SEQUENCE: 121
gttcaagccc agaagcgatg t                                               21

<210> SEQ ID NO 122
<211> LENGTH: 23
<212> TYPE: DNA
<213> ORGANISM: Artificial Sequence
<220> FEATURE:
<223> OTHER INFORMATION: Staphylococcus aureus

<400> SEQUENCE: 122
tcgggcataa atgtcaggaa aat                                             23

<210> SEQ ID NO 123
<211> LENGTH: 33

```
<212> TYPE: DNA
<213> ORGANISM: Artificial Sequence
<220> FEATURE:
<223> OTHER INFORMATION: Staphylococcus aureus

<400> SEQUENCE: 123
ttattaggta aaccagcagt aagtgaacaa cca                                33

<210> SEQ ID NO 124
<211> LENGTH: 36
<212> TYPE: DNA
<213> ORGANISM: Artificial Sequence
<220> FEATURE:
<223> OTHER INFORMATION: Staphylococcus aureus

<400> SEQUENCE: 124
cgcttgccac atcaaatgat gcgggttgtg caagcg                             36

<210> SEQ ID NO 125
<211> LENGTH: 36
<212> TYPE: DNA
<213> ORGANISM: Artificial Sequence
<220> FEATURE:
<223> OTHER INFORMATION: Staphylococcus aureus

<400> SEQUENCE: 125
cccaccccac atcaaatgat gcgggttgtg ggtggg                             36

<210> SEQ ID NO 126
<211> LENGTH: 37
<212> TYPE: DNA
<213> ORGANISM: Artificial Sequence
<220> FEATURE:
<223> OTHER INFORMATION: Staphylococcus aureus

<400> SEQUENCE: 126
cccgcgcgta gttactgcgt tgtaagacgt ccgcggg                            37

<210> SEQ ID NO 127
<211> LENGTH: 48
<212> TYPE: DNA
<213> ORGANISM: Artificial Sequence
<220> FEATURE:
<223> OTHER INFORMATION: Staphylococcus aureus

<400> SEQUENCE: 127
cgaccggatt cccacatcaa atgatgcggg ttgtgttaat tccggtcg                48

<210> SEQ ID NO 128
<211> LENGTH: 37
<212> TYPE: DNA
<213> ORGANISM: Artificial Sequence
<220> FEATURE:
<223> OTHER INFORMATION: Staphylococcus aureus

<400> SEQUENCE: 128
cccgcgcrta gttactrcgt tgtaagacgt ccgcggg                            37

<210> SEQ ID NO 129
<211> LENGTH: 29
<212> TYPE: DNA
<213> ORGANISM: Artificial Sequence
<220> FEATURE:
<223> OTHER INFORMATION: Staphylococcus aureus

<400> SEQUENCE: 129
ccccgtagtt actgcgttgt aagacgggg                                     29
```

```
<210> SEQ ID NO 130
<211> LENGTH: 37
<212> TYPE: DNA
<213> ORGANISM: Artificial Sequence
<220> FEATURE:
<223> OTHER INFORMATION: Staphylococcus aureus

<400> SEQUENCE: 130
cccgcgcata gttactgcgt tgtaagacgt ccgcggg                              37

<210> SEQ ID NO 131
<211> LENGTH: 37
<212> TYPE: DNA
<213> ORGANISM: Artificial Sequence
<220> FEATURE:
<223> OTHER INFORMATION: Staphylococcus aureus

<400> SEQUENCE: 131
cccgcgcgta gttactacgt tgtaagacgt ccgcggg                              37

<210> SEQ ID NO 132
<211> LENGTH: 27
<212> TYPE: DNA
<213> ORGANISM: Artificial Sequence
<220> FEATURE:
<223> OTHER INFORMATION: Staphylococcus aureus

<400> SEQUENCE: 132
gtttttatca ccatattgaa tttatac                                        27

<210> SEQ ID NO 133
<211> LENGTH: 25
<212> TYPE: DNA
<213> ORGANISM: Artificial Sequence
<220> FEATURE:
<223> OTHER INFORMATION: Staphylococcus aureus

<400> SEQUENCE: 133
atttacttga aagactgcgg aggag                                          25

<210> SEQ ID NO 134
<211> LENGTH: 24
<212> TYPE: DNA
<213> ORGANISM: Artificial Sequence
<220> FEATURE:
<223> OTHER INFORMATION: Staphylococcus aureus

<400> SEQUENCE: 134
tgtttgagct tccacagcta tttc                                           24

<210> SEQ ID NO 135
<211> LENGTH: 27
<212> TYPE: DNA
<213> ORGANISM: Artificial Sequence
<220> FEATURE:
<223> OTHER INFORMATION: Staphylococcus aureus

<400> SEQUENCE: 135
ccctataatt ccaattattg cactaac                                        27

<210> SEQ ID NO 136
<211> LENGTH: 25
<212> TYPE: DNA
<213> ORGANISM: Artificial Sequence
<220> FEATURE:
<223> OTHER INFORMATION: Staphylococcus aureus
```

<400> SEQUENCE: 136
atgaggagat aataatttgg agggt                                    25

<210> SEQ ID NO 137
<211> LENGTH: 27
<212> TYPE: DNA
<213> ORGANISM: Artificial Sequence
<220> FEATURE:
<223> OTHER INFORMATION: Staphylococcus aureus

<400> SEQUENCE: 137
gctgaaaaaa ccgcatcatt trtgrta                                  27

<210> SEQ ID NO 138
<211> LENGTH: 27
<212> TYPE: DNA
<213> ORGANISM: Artificial Sequence
<220> FEATURE:
<223> OTHER INFORMATION: Staphylococcus aureus

<400> SEQUENCE: 138
gctgaaaaaa ccgcatcatt tatgata                                  27

<210> SEQ ID NO 139
<211> LENGTH: 28
<212> TYPE: DNA
<213> ORGANISM: Artificial Sequence
<220> FEATURE:
<223> OTHER INFORMATION: Staphylococcus aureus
<220> FEATURE:
<221> NAME/KEY: misc_feature
<222> LOCATION: 27
<223> OTHER INFORMATION: n = a, t, c, or g

<400> SEQUENCE: 139
gaaaaaaccg catcatttat gatatgnt                                 28

<210> SEQ ID NO 140
<211> LENGTH: 22
<212> TYPE: DNA
<213> ORGANISM: Artificial Sequence
<220> FEATURE:
<223> OTHER INFORMATION: Staphylococcus aureus

<400> SEQUENCE: 140
tatattgtgg catgatttct tc                                       22

<210> SEQ ID NO 141
<211> LENGTH: 23
<212> TYPE: DNA
<213> ORGANISM: Artificial Sequence
<220> FEATURE:
<223> OTHER INFORMATION: Staphylococcus aureus

<400> SEQUENCE: 141
cgaatggact agcactttct aaa                                      23

<210> SEQ ID NO 142
<211> LENGTH: 22
<212> TYPE: DNA
<213> ORGANISM: Artificial Sequence
<220> FEATURE:
<223> OTHER INFORMATION: Staphylococcus aureus

<400> SEQUENCE: 142
agacaacttt atgcaggtcc tt                                       22

<210> SEQ ID NO 143
<211> LENGTH: 22
<212> TYPE: DNA
<213> ORGANISM: Artificial Sequence
<220> FEATURE:
<223> OTHER INFORMATION: Staphylococcus aureus

<400> SEQUENCE: 143
taactgcttg ggtaacctta tc                                            22

<210> SEQ ID NO 144
<211> LENGTH: 29
<212> TYPE: DNA
<213> ORGANISM: Artificial Sequence
<220> FEATURE:
<223> OTHER INFORMATION: Staphylococcus aureus

<400> SEQUENCE: 144
atttcatata tgtaattcct ccacatctc                                     29

<210> SEQ ID NO 145
<211> LENGTH: 29
<212> TYPE: DNA
<213> ORGANISM: Artificial Sequence
<220> FEATURE:
<223> OTHER INFORMATION: Staphylococcus aureus

<400> SEQUENCE: 145
tttagtttta tttatgatac gcttctcca                                     29

<210> SEQ ID NO 146
<211> LENGTH: 25
<212> TYPE: DNA
<213> ORGANISM: Artificial Sequence
<220> FEATURE:
<223> OTHER INFORMATION: Staphylococcus aureus

<400> SEQUENCE: 146
ctctataaac atcgtatgat attgc                                         25

<210> SEQ ID NO 147
<211> LENGTH: 30
<212> TYPE: DNA
<213> ORGANISM: Artificial Sequence
<220> FEATURE:
<223> OTHER INFORMATION: Staphylococcus aureus
<220> FEATURE:
<221> NAME/KEY: misc_feature
<222> LOCATION: 29
<223> OTHER INFORMATION: n = a, t, c, or g

<400> SEQUENCE: 147
cctaattttt agttttattt atgatacgnt                                    30

<210> SEQ ID NO 148
<211> LENGTH: 35
<212> TYPE: DNA
<213> ORGANISM: Artificial Sequence
<220> FEATURE:
<223> OTHER INFORMATION: Staphylococcus aureus
<220> FEATURE:
<221> NAME/KEY: misc_feature
<222> LOCATION: 34
<223> OTHER INFORMATION: n = a, t, c, or g

<400> SEQUENCE: 148
cacaacctaa ttttagttt tatttatgat acgnt                               35

-continued

<210> SEQ ID NO 149
<211> LENGTH: 23
<212> TYPE: DNA
<213> ORGANISM: Artificial Sequence
<220> FEATURE:
<223> OTHER INFORMATION: Staphylococcus aureus

<400> SEQUENCE: 149
atattctaga tcatcaatag ttg                                              23

<210> SEQ ID NO 150
<211> LENGTH: 29
<212> TYPE: DNA
<213> ORGANISM: Artificial Sequence
<220> FEATURE:
<223> OTHER INFORMATION: Staphylococcus aureus

<400> SEQUENCE: 150
caaatattat ctcgtaattt accttgttc                                        29

<210> SEQ ID NO 151
<211> LENGTH: 26
<212> TYPE: DNA
<213> ORGANISM: Artificial Sequence
<220> FEATURE:
<223> OTHER INFORMATION: Staphylococcus aureus

<400> SEQUENCE: 151
ctactatgaa ctgtgcaatt tgttct                                           26

<210> SEQ ID NO 152
<211> LENGTH: 25
<212> TYPE: DNA
<213> ORGANISM: Artificial Sequence
<220> FEATURE:
<223> OTHER INFORMATION: Staphylococcus aureus

<400> SEQUENCE: 152
caatcggtat ctgtaaatat caaat                                            25

<210> SEQ ID NO 153
<211> LENGTH: 22
<212> TYPE: DNA
<213> ORGANISM: Artificial Sequence
<220> FEATURE:
<223> OTHER INFORMATION: Staphylococcus aureus

<400> SEQUENCE: 153
ttggttccat ctgaactttg ag                                               22

<210> SEQ ID NO 154
<211> LENGTH: 26
<212> TYPE: DNA
<213> ORGANISM: Artificial Sequence
<220> FEATURE:
<223> OTHER INFORMATION: Staphylococcus aureus

<400> SEQUENCE: 154
cacagaaatg taattttgga atgagg                                           26

<210> SEQ ID NO 155
<211> LENGTH: 29
<212> TYPE: DNA
<213> ORGANISM: Artificial Sequence
<220> FEATURE:
<223> OTHER INFORMATION: Staphylococcus aureus

```
<400> SEQUENCE: 155
ctctgcttta tattataaaa ttacggctg                                      29

<210> SEQ ID NO 156
<211> LENGTH: 24
<212> TYPE: DNA
<213> ORGANISM: Artificial Sequence
<220> FEATURE:
<223> OTHER INFORMATION: Staphylococcus aureus

<400> SEQUENCE: 156
tcgcatacct gtttatcttc tact                                           24

<210> SEQ ID NO 157
<211> LENGTH: 24
<212> TYPE: DNA
<213> ORGANISM: Artificial Sequence
<220> FEATURE:
<223> OTHER INFORMATION: Staphylococcus aureus

<400> SEQUENCE: 157
tttaaattca gctatatggg gaga                                           24

<210> SEQ ID NO 158
<211> LENGTH: 22
<212> TYPE: DNA
<213> ORGANISM: Artificial Sequence
<220> FEATURE:
<223> OTHER INFORMATION: Staphylococcus aureus

<400> SEQUENCE: 158
ttccgttttg ctattccata at                                             22

<210> SEQ ID NO 159
<211> LENGTH: 20
<212> TYPE: DNA
<213> ORGANISM: Artificial Sequence
<220> FEATURE:
<223> OTHER INFORMATION: Staphylococcus aureus

<400> SEQUENCE: 159
aaaagaaaga cggtgaaggc                                                20

<210> SEQ ID NO 160
<211> LENGTH: 25
<212> TYPE: DNA
<213> ORGANISM: Artificial Sequence
<220> FEATURE:
<223> OTHER INFORMATION: Staphylococcus aureus

<400> SEQUENCE: 160
cacttcatta tactgttttc tttgc                                          25

<210> SEQ ID NO 161
<211> LENGTH: 22
<212> TYPE: DNA
<213> ORGANISM: Artificial Sequence
<220> FEATURE:
<223> OTHER INFORMATION: Staphylococcus aureus

<400> SEQUENCE: 161
tcaccgtctt tcttttgacc tt                                             22

<210> SEQ ID NO 162
<211> LENGTH: 27
```

```
<212> TYPE: DNA
<213> ORGANISM: Artificial Sequence
<220> FEATURE:
<223> OTHER INFORMATION: Staphylococcus aureus

<400> SEQUENCE: 162
cactttttat tcttcaaaga tttgagc                                          27

<210> SEQ ID NO 163
<211> LENGTH: 28
<212> TYPE: DNA
<213> ORGANISM: Artificial Sequence
<220> FEATURE:
<223> OTHER INFORMATION: Staphylococcus aureus

<400> SEQUENCE: 163
atggaaattc ttaatcttta cttgtacc                                         28

<210> SEQ ID NO 164
<211> LENGTH: 24
<212> TYPE: DNA
<213> ORGANISM: Artificial Sequence
<220> FEATURE:
<223> OTHER INFORMATION: Staphylococcus aureus

<400> SEQUENCE: 164
agcatcttct ttacatcgct tact                                             24

<210> SEQ ID NO 165
<211> LENGTH: 21
<212> TYPE: DNA
<213> ORGANISM: Artificial Sequence
<220> FEATURE:
<223> OTHER INFORMATION: Staphylococcus aureus

<400> SEQUENCE: 165
ttgaggatca aaagttgttg c                                                21

<210> SEQ ID NO 166
<211> LENGTH: 21
<212> TYPE: DNA
<213> ORGANISM: Artificial Sequence
<220> FEATURE:
<223> OTHER INFORMATION: Staphylococcus aureus

<400> SEQUENCE: 166
cgatgatttt atagtaggag a                                                21

<210> SEQ ID NO 167
<211> LENGTH: 28
<212> TYPE: DNA
<213> ORGANISM: Artificial Sequence
<220> FEATURE:
<223> OTHER INFORMATION: Staphylococcus aureus

<400> SEQUENCE: 167
ttcaatctct aaatctaaat cagttttg                                         28

<210> SEQ ID NO 168
<211> LENGTH: 24
<212> TYPE: DNA
<213> ORGANISM: Artificial Sequence
<220> FEATURE:
<223> OTHER INFORMATION: Staphylococcus aureus

<400> SEQUENCE: 168
aggcgagaaa atgaacata tcaa                                              24
```

<210> SEQ ID NO 169
<211> LENGTH: 23
<212> TYPE: DNA
<213> ORGANISM: Artificial Sequence
<220> FEATURE:
<223> OTHER INFORMATION: Staphylococcus aureus

<400> SEQUENCE: 169
cagcaattcw cataaacctc ata                                       23

<210> SEQ ID NO 170
<211> LENGTH: 27
<212> TYPE: DNA
<213> ORGANISM: Artificial Sequence
<220> FEATURE:
<223> OTHER INFORMATION: Staphylococcus aureus

<400> SEQUENCE: 170
acaaactttg agggganttt tagtaaa                                   27

<210> SEQ ID NO 171
<211> LENGTH: 24
<212> TYPE: DNA
<213> ORGANISM: Artificial Sequence
<220> FEATURE:
<223> OTHER INFORMATION: Staphylococcus aureus

<400> SEQUENCE: 171
ggatgtgggt atgctaatgt tgtt                                      24

<210> SEQ ID NO 172
<211> LENGTH: 27
<212> TYPE: DNA
<213> ORGANISM: Artificial Sequence
<220> FEATURE:
<223> OTHER INFORMATION: Staphylococcus aureus

<400> SEQUENCE: 172
tgaacaattt tatttctcat accatag                                   27

<210> SEQ ID NO 173
<211> LENGTH: 26
<212> TYPE: DNA
<213> ORGANISM: Artificial Sequence
<220> FEATURE:
<223> OTHER INFORMATION: Staphylococcus aureus

<400> SEQUENCE: 173
tcccctaatg atagctggta tatatt                                    26

<210> SEQ ID NO 174
<211> LENGTH: 27
<212> TYPE: DNA
<213> ORGANISM: Artificial Sequence
<220> FEATURE:
<223> OTHER INFORMATION: Staphylococcus aureus

<400> SEQUENCE: 174
tctagggaat caaagaaaag taatagt                                   27

<210> SEQ ID NO 175
<211> LENGTH: 26
<212> TYPE: DNA
<213> ORGANISM: Artificial Sequence
<220> FEATURE:
<223> OTHER INFORMATION: Staphylococcus aureus

```
<400> SEQUENCE: 175
ggtacaagta aagattaaga atttcc                                          26

<210> SEQ ID NO 176
<211> LENGTH: 25
<212> TYPE: DNA
<213> ORGANISM: Artificial Sequence
<220> FEATURE:
<223> OTHER INFORMATION: Staphylococcus aureus

<400> SEQUENCE: 176
actagaatct ccaaatgaat ccagt                                           25

<210> SEQ ID NO 177
<211> LENGTH: 24
<212> TYPE: DNA
<213> ORGANISM: Artificial Sequence
<220> FEATURE:
<223> OTHER INFORMATION: Staphylococcus aureus

<400> SEQUENCE: 177
tgataagcca ttcattcacc ctaa                                            24

<210> SEQ ID NO 178
<211> LENGTH: 24
<212> TYPE: DNA
<213> ORGANISM: Artificial Sequence
<220> FEATURE:
<223> OTHER INFORMATION: Staphylococcus aureus

<400> SEQUENCE: 178
aatggcttat caaagtgaat atgc                                            24

<210> SEQ ID NO 179
<211> LENGTH: 24
<212> TYPE: DNA
<213> ORGANISM: Artificial Sequence
<220> FEATURE:
<223> OTHER INFORMATION: Staphylococcus aureus

<400> SEQUENCE: 179
taatttcctt ttttttccatt cctc                                           24

<210> SEQ ID NO 180
<211> LENGTH: 25
<212> TYPE: DNA
<213> ORGANISM: Artificial Sequence
<220> FEATURE:
<223> OTHER INFORMATION: Staphylococcus aureus

<400> SEQUENCE: 180
tgagatctgc tggaacaaaa gtgaa                                           25

<210> SEQ ID NO 181
<211> LENGTH: 20
<212> TYPE: DNA
<213> ORGANISM: Artificial Sequence
<220> FEATURE:
<223> OTHER INFORMATION: Staphylococcus aureus

<400> SEQUENCE: 181
cggtcgagtt tgctgaagaa                                                 20

<210> SEQ ID NO 182
<211> LENGTH: 26
```

```
<212> TYPE: DNA
<213> ORGANISM: Artificial Sequence
<220> FEATURE:
<223> OTHER INFORMATION: Staphylococcus aureus

<400> SEQUENCE: 182
ctattgttcc acaaattatg attact                                          26

<210> SEQ ID NO 183
<211> LENGTH: 26
<212> TYPE: DNA
<213> ORGANISM: Artificial Sequence
<220> FEATURE:
<223> OTHER INFORMATION: Staphylococcus aureus

<400> SEQUENCE: 183
cttcttttct tgttattctt tcttct                                          26

<210> SEQ ID NO 184
<211> LENGTH: 23
<212> TYPE: DNA
<213> ORGANISM: Artificial Sequence
<220> FEATURE:
<223> OTHER INFORMATION: Staphylococcus aureus

<400> SEQUENCE: 184
gttgccatag attcaatttc tag                                             23

<210> SEQ ID NO 185
<211> LENGTH: 19
<212> TYPE: DNA
<213> ORGANISM: Artificial Sequence
<220> FEATURE:
<223> OTHER INFORMATION: Staphylococcus aureus

<400> SEQUENCE: 185
caccctgcaa gatatgttt                                                  19

<210> SEQ ID NO 186
<211> LENGTH: 25
<212> TYPE: DNA
<213> ORGANISM: Artificial Sequence
<220> FEATURE:
<223> OTHER INFORMATION: Staphylococcus aureus

<400> SEQUENCE: 186
aatggaattt gttaatttca taaat                                           25

<210> SEQ ID NO 187
<211> LENGTH: 23
<212> TYPE: DNA
<213> ORGANISM: Artificial Sequence
<220> FEATURE:
<223> OTHER INFORMATION: Staphylococcus aureus

<400> SEQUENCE: 187
ttccgaagct aattctgtta ata                                             23

<210> SEQ ID NO 188
<211> LENGTH: 25
<212> TYPE: DNA
<213> ORGANISM: Artificial Sequence
<220> FEATURE:
<223> OTHER INFORMATION: Staphylococcus aureus

<400> SEQUENCE: 188
ttccgaagtc ataatcaatc aaatt                                           25
```

<210> SEQ ID NO 189
<211> LENGTH: 24
<212> TYPE: DNA
<213> ORGANISM: Artificial Sequence
<220> FEATURE:
<223> OTHER INFORMATION: Staphylococcus aureus

<400> SEQUENCE: 189
caaattgtag cattcttgaa ctat                                          24

<210> SEQ ID NO 190
<211> LENGTH: 23
<212> TYPE: DNA
<213> ORGANISM: Artificial Sequence
<220> FEATURE:
<223> OTHER INFORMATION: Staphylococcus aureus

<400> SEQUENCE: 190
gccaaaatca aaccacaatc aac                                           23

<210> SEQ ID NO 191
<211> LENGTH: 23
<212> TYPE: DNA
<213> ORGANISM: Artificial Sequence
<220> FEATURE:
<223> OTHER INFORMATION: Staphylococcus aureus

<400> SEQUENCE: 191
gccaaaatca aaccacaatc cac                                           23

<210> SEQ ID NO 192
<211> LENGTH: 2150
<212> TYPE: DNA
<213> ORGANISM: Artificial Sequence
<220> FEATURE:
<223> OTHER INFORMATION: Staphylococcus aureus

<400> SEQUENCE: 192
tgaatcgttt aacgtgtcac atgatgcgat agatccgcaa ttttatattt tccataataa      60
ctataagaag tttacgattt taacagatac gggttacgtg tctgatcgta tgaaaggtat     120
gatacgtggc agcgatgcat ttatttttga gagtaatcat gacgtcgata tgttgagaat     180
gtgtcgttat ccatggaaga cgaaacaacg cattttaggc gatatgggtc atgtatctaa     240
tgaggatgcg ggtcatgcga tgacagacgt gattacaggt aacacgaaac gtatttactt     300
atcgcattta tcacaagata taatatgaa agatttggcg cgtatgagtg ttggccaagt     360
attgaacgaa cacgatattg atacggaaaa agaagtattg ctatgtgata cggataaagc     420
tattccaaca ccaatatata caatataaat gagagtcatc cgataaagtt ccgcactgct     480
gtgaaacgac tttatcgggt gctttttat gttgttggtg ggaaatggct gttgttgagt     540
tgaatcggat tgattgaaat gtgtaaaata attcgatatt aaatgtaatt tataaataat     600
ttacataaaa tcaaacattt taatataagg attatgataa tatattggtg tatgacagtt     660
aatggaggga acgaaatgaa agctttatta cttaaaacaa gtgtatggct cgttttgctt     720
tttagtgtga tgggattatg gcatgtctcg aacgcggctg agcagcatac accaatgaaa     780
gcacaagcag caacaacaga taagcaacaa gtaacgccaa caaggaagc ggctcatcaa     840 tctggtgaag aagcggcaac caacgtatca gcatcagtac agggaacagc tgatgataca     900
aacaacaaag taacatccaa cgcaccatct aacaaaccat ctacagcagt tcaacaaca      960 gtaaacgaaa cgcgcgacgt agatgcacaa caagcctcaa cacaaaaacc aactcaatca    1020

```
gcaacattca aattatcaaa tgctaaaaca gcatcacttt caccacgaat gtttgctgct    1080
aatgcaccac aaacaacaac acataaaata tggttctgtt gcaaagtaaa aaaatatagc    1140
taaccactaa tttatcatgt cagtgttcgc ttaacttgct agcatgatgc taatttcgtg    1200
gcatggcgaa aatccgtaga tctgaagaga cctgcggttc ttttatata gagcgtaaat     1260 acattcaata cctttaaag tattctttgc tgtattgata ctttgatacc ttgtctttct     1320
tactttaata tgacggtgat cttgctcaat gaggttattc agatatttcg atgtacaatg    1380
acagtcaggt ttaagtttaa aagctttaat tactttagcc attgctacct tcgttgaagg    1440
tgcctgatct gtaattacct tttgaggttt accaaattgt ttaatgagac gtttgataaa    1500
cgcatatgct gaatgattat ctcgttgctt acgcaaccaa atatctaatg tatgtccctc    1560
tgcatcaatg gcacgatata aatagctcca ttttccttt attttgatgt acgtctcatc     1620
aatacgccat ttgtaataag ctttttatg ctttttcttc caatttgat acaaattgg       1680 ggcatattct tgaacccaac ggtagaccgt tgaatgatga acgttacac cacgttccct     1740 taatatttca gatatatcac gataactcaa tgtatatctt agatagtagc caacggctac    1800
agtgataaca tccttgttaa attgtttata tctgaaatag ttcatacaga agactccttt    1860
ttgttaaaat tatactataa attcaacttt gcaacagaac cgaaaaacta gacttgatta    1920
caaaatggag cttgggacat aaatgatttt ttaaaaatga gatgagacgt agattaactc    1980
cataatcaat acgaatctat cgacttcttt atttatgata ttcatctctt tttaatggaa    2040
ataaaagtgc gattaatgtg ataatacagt tacgttaatt aaaaaaataa aaatgcaagg    2100
agaggtaata tgctaactgt atatggacat agaggattac ctagtaaagc                2150

<210> SEQ ID NO 193
<211> LENGTH: 23
<212> TYPE: DNA
<213> ORGANISM: Artificial Sequence
<220> FEATURE:
<223> OTHER INFORMATION: Staphylococcus aureus

<400> SEQUENCE: 193
gccaaaatta aaccacaatc cac                                               23

<210> SEQ ID NO 194
<211> LENGTH: 24
<212> TYPE: DNA
<213> ORGANISM: Artificial Sequence
<220> FEATURE:
<223> OTHER INFORMATION: Staphylococcus aureus

<400> SEQUENCE: 194
ctcccatttc ttccaaaaaa tata                                              24

<210> SEQ ID NO 195
<211> LENGTH: 29
<212> TYPE: DNA
<213> ORGANISM: Artificial Sequence
<220> FEATURE:
<223> OTHER INFORMATION: Staphylococcus aureus

<400> SEQUENCE: 195
caaatattat ctcgtaattt accttgttc                                         29

<210> SEQ ID NO 196
<211> LENGTH: 29
<212> TYPE: DNA
<213> ORGANISM: Artificial Sequence
```

```
<220> FEATURE:
<223> OTHER INFORMATION: Staphylococcus aureus

<400> SEQUENCE: 196
ctctgcttta tattataaaa ttacggctg                                        29

<210> SEQ ID NO 197
<211> LENGTH: 22
<212> TYPE: DNA
<213> ORGANISM: Artificial Sequence
<220> FEATURE:
<223> OTHER INFORMATION: Staphylococcus aureus

<400> SEQUENCE: 197
caagctccat tttgtaatca ag                                               22

<210> SEQ ID NO 198
<211> LENGTH: 22
<212> TYPE: DNA
<213> ORGANISM: Artificial Sequence
<220> FEATURE:
<223> OTHER INFORMATION: Staphylococcus aureus

<400> SEQUENCE: 198
caagctccat tttgtaatca ag                                               22

<210> SEQ ID NO 199
<211> LENGTH: 26
<212> TYPE: DNA
<213> ORGANISM: Artificial Sequence
<220> FEATURE:
<223> OTHER INFORMATION: Staphylococcus aureus

<400> SEQUENCE: 199
atgtcaaaaa tcatgaacct cattac                                           26

<210> SEQ ID NO 200
<211> LENGTH: 686
<212> TYPE: DNA
<213> ORGANISM: Artificial Sequence
<220> FEATURE:
<223> OTHER INFORMATION: Staphylococcus aureus

<400> SEQUENCE: 200
atgacagaat acttattaag tgctggcata tgtatggcaa ttgtttcaat attacttata      60
gggatggcta tcagtaatgt ttcgaaaggg caatacgcaa agaggttttt cttttttcgct    120 actagttgct tagtgttaac tttagttgta gtttcaagtc taagtagctc agcaaatgca    180
tcacaaacag ataacggcgt aaatagaagt ggttctgaag atccaacagt atatagtgca    240
acttcaacta aaaaattaca taaagaacct gcgacattaa ttaaagcgat tgatggtgat    300
acggttaaat taatgtacaa aggtcaacca atgacattca gactattatt agttgataca    360
cctgaaacaa agcatcctaa aaaaggtgta gagaaatatg gccctgaagc aagtgcattt    420
acgaaaaaaa tggtagaaaa tgcaaataaa attgaagtcg agtttgacaa aggtcaaaga    480
actgataaat atggacgtgg cttagcgtat atttatgctg atggaaaaat ggtaaacgaa    540
gctttagttc gtcaaggctt ggctaaagtt gcttatgttt ataaacctaa caatacacat    600
gaacaacttt aagaaaaag tgaagcacaa gcgaaaaaag agaaattaaa tatttggagc    660
gaagacaacg ctgattcagg tcaata                                          686

<210> SEQ ID NO 201
<211> LENGTH: 29
```

```
<212> TYPE: DNA
<213> ORGANISM: Artificial Sequence
<220> FEATURE:
<223> OTHER INFORMATION: Staphylococcus aureus

<400> SEQUENCE: 201
atttcatata tgtaattcct ccacatctc                                    29

<210> SEQ ID NO 202
<211> LENGTH: 37
<212> TYPE: DNA
<213> ORGANISM: Artificial Sequence
<220> FEATURE:
<223> OTHER INFORMATION: Staphylococcus aureus

<400> SEQUENCE: 202
cccgcgcgta gttactgcgt tgtaagacgt ccgcggg                           37

<210> SEQ ID NO 203
<211> LENGTH: 37
<212> TYPE: DNA
<213> ORGANISM: Artificial Sequence
<220> FEATURE:
<223> OTHER INFORMATION: Staphylococcus aureus

<400> SEQUENCE: 203
cccgcgcata gttactgcgt tgtaagacgt ccgcggg                           37

<210> SEQ ID NO 204
<211> LENGTH: 37
<212> TYPE: DNA
<213> ORGANISM: Artificial Sequence
<220> FEATURE:
<223> OTHER INFORMATION: Staphylococcus aureus

<400> SEQUENCE: 204
cccgcgcgta gttactacgt tgtaagacgt ccgcggg                           37

<210> SEQ ID NO 205
<211> LENGTH: 18
<212> TYPE: DNA
<213> ORGANISM: Artificial Sequence
<220> FEATURE:
<223> OTHER INFORMATION: Staphylococcus aureus

<400> SEQUENCE: 205
ggatcaaacg gcctgcac                                                18
```

DETECTION OF *STAPHYLOCOCCUS AUREUS* AND IDENTIFICATION OF METHICILLIN-RESISTANT *STAPHYLOCOCCUS AUREUS*

RELATED APPLICATIONS

The present application claims priority to U.S. Provisional Application Ser. No. 60/870,823, filed on Dec. 19, 2006, by Jean et al. entitled "DETECTION OF STAPHYLOCOCCUS AUREUS AND IDENTIFICATION OF METHICILLIN-RESISTANT STAPHYLOCOCCUS AUREUS," which is hereby expressly incorporated by reference in its entirety.

SEQUENCE LISTING

The present application is being filed along with a Sequence Listing in electronic format. The Sequence Listing is provided as a file entitled GENOM.072A.TXT, created Nov. 29, 2007, which is 124 KB in size. The information in the electronic format of the Sequence Listing is incorporated herein by reference in its entirety.

BACKGROUND OF THE INVENTION

Members of the genus *Staphylococcus* are major human pathogens, causing a wide variety of hospital and community acquired infections worldwide. The coagulase-positive species *Staphylococcus aureus* is well documented as a human opportunistic pathogen (Murray et al. Eds, 2003, Manual of Clinical Microbiology, 8th Ed., ASM Press, Washington, D.C.). Nosocomial infections caused by *S. aureus* are a major cause of morbidity and mortality. Some of the most common infections caused by *S. aureus* involve the skin, and they include furuncles or boils, cellulitis, impetigo, and postoperative wound infections at various sites. Some of the more serious infections produced by *S. aureus* are bacteremia, pneumonia, osteomyelitis, acute endocarditis, myocarditis, pericarditis, cerebritis, meningitis, scalded skin syndrome, and various abcesses. Food poisoning mediated by staphylococcal enterotoxins is another important syndrome associated with *S. aureus*. Toxic shock syndrome, a community-acquired disease, has also been attributed to infection or colonization with toxigenic *S. aureus*.

Coagulase-negative Staphylococci had been regarded as harmless skin commensals prior to the 1970s, however, they are now recognized as important causes of human infections (Kloos, et al. (2004) Clin. Microbiol. Rev. 7:117-140). In addition to being among the most frequently isolated bacteria in clinical microbiology laboratories, coagulase-negative Staphylococci serve as reservoirs of antimicrobial resistance determinants (Bastos, et al. (1999) Eur. J. Clin. Microbiol. Infect. Dis. 18:393-398). As such, it is important to characterize and distinguish *S. aureus* strains from other, coagulase-negative Staphylococci.

*S. aureus* strains produce an extracellular thermostable nuclease (thermostable TNase) with a frequency similar to that at which they produce coagulase. The sequence of the gene encoding TNase, nuc, was first disclosed in 1985 (Kovacevi et al. (1985), J. Bact. 162:521-528). TNase is a 17 kDa protein that degrades both RNA and DNA at temperatures up to 100° C. TNase activity is not specific for *S. aureus*, however, *S. aureus* species-specific sequences exist. See, e.g., Brackstad, et al. (1992), J. Clin. Microbiol. 30:1654-1660; Zhang, et al. (2004), J. Clin. Microbiol. 42:4947-4955; Chesneau, et al. (1993) Mol. Cell. Probes 7:301-310, Wilson, et al. (1991) Appl. Environ. Microbiol. 57:1793-1798; Poulsen et al., (2003) J. Antimicrob. Chemo. 51:419-421, Costa et al., (2005), Diag. Microbiol. and Infect. Dis, 51: 13-17, Shittu et al., (2006), Diagn Microbiol Infect Dis. 2006 Jul. 17. To date, none of the *S. aureus*-specific nuc sequences have been proven to be clinically useful by way of a large specificity study. Therefore, there exists a need for oligonucleotides that have been proven to be both highly specific and sensitive, which are useful in rapid detection and identification of *S. aureus* from clinical samples.

Both *S. aureus* and coagulase-negative Staphylococci have a remarkable ability to accumulate additional antibiotic resistant determinants, resulting in the formation of multidrug-resistant strains. This resistance limits therapeutic options for treatment and substantially increases patient morbidity and mortality. Methicillin-resistant *S. aureus* (MRSA) emerged in the 1980s as a major clinical and epidemiologic problem in hospitals (Oliveira et al., (2002) Lancet Infect Dis. 2:180-189). MRSA are resistant to all β-lactams including penicillins, cephalosporins, carbapenems, and monobactams, which are the most commonly used antibiotics to cure *S. aureus* infections. MRSA infections can only be treated with more toxic and more costly antibiotics, which are normally used as the last line of defense. Since MRSA can spread easily from patient to patient via personnel, hospitals over the world are confronted with the problem to control MRSA.

Methicillin resistance in *S. aureus* is unique in that it is due to acquisition of DNA from other coagulase-negative staphylococci (CNS), coding for a surnumerary β-lactam-resistant penicillin-binding protein (PBP), which takes over the biosynthetic functions of the normal PBPs when the cell is exposed to β-lactam antibiotics. *S. aureus* normally contains four PBPs, of which PBPs 1, 2 and 3 are essential. The low-affinity PBP in MRSA, termed PBP 2a (or PBP2'), is encoded by the chromosomal mecA gene and functions as a β-lactam-resistant transpeptidase. The mecA gene is absent from methicillin-sensitive *S. aureus* but is widely distributed among other species of staphylococci and is highly conserved (Ubukata et al., (1990) Antimicrob. Agents Chemother. 34:170-172).

Nucleotide sequence determination of the DNA region surrounding the mecA gene from *S. aureus* strain N315 (isolated in Japan in 1982), led to the discovery that the mecA gene is carried by a novel genetic element, designated staphylococcal cassette chromosome mec (SCCmec), which is inserted into the chromosome. SCCmec is a mobile genetic element characterized by the presence of terminal inverted and direct repeats, a set of site-specific recombinase genes (ccrA and ccrB), and the mecA gene complex (Ito et al., (1999) Antimicrob. Agents Chemother. 43:1449-1458; Katayama et al., (2000) Antimicrob. Agents Chemother. 44:1549-1555). SCCmec is precisely excised from the chromosome of *S. aureus* strain N315 and integrates into a specific *S. aureus* chromosomal site in the same orientation through recombinases encoded by the ccrA and ccrB genes. Cloning and sequence analysis of the DNA surrounding the mecA gene from MRSA strains NCTC 10442 (the first MRSA strain isolated in England in 1961) and 85/2082 (a strain from New Zealand isolated in 1985) led to the discovery of two novel genetic elements that shared similar structural features of SCCmec. The three SCCmec have been designated type I (NCTC 10442), type II (N315) and type III (85/2082) based on the year of isolation of the strains (Ito et al., (2001) Antimicrob. Agents Chemother. 45:1323-1336). Hiramatsu et al. have found that the SCCmec DNAs are integrated at a specific site in the chromosome of methicillin-sensitive *S. aureus* (MSSA). The nucleotide sequence of the regions surrounding the left and right boundaries of SCCmec DNA (i.e. attL and attR, respectively), as well as those of the regions around the SCCmec DNA integration site (i.e. attBscc which is the bacterial chromosome attachment site for SCCmec DNA), were analyzed. Sequence analysis of the attL, attR and attBscc sites revealed that attBscc is located at the 3' end of a novel open reading frame (ORF), orfX orfX encodes a putative 159-amino acid polypeptide that exhibits sequence homology with some previously identified polypeptides of unknown function (Ito et al., (1999) Antimicrob. Agents Chemother. 43:1449-1458). Two new types of SCCmec, designated type IV and type V were recently described (Ma et al., (2002) Antimicrob. Agents Chemother. 46:1147-1152, Ito et al., (2004) Antimicrob Agents Chemother. 48:2637-2651, Oliveira et al., (2001) Microb. Drug Resist. 7:349-360). Oliveira et al. also recently reported the existence of SCCmec type VI. Oliveira et al., (2006), Antimicrob Agents Chemother. 50:3457-3459. The sequence of the right extremity of some *Staphylococcus* strains classified as SCCmec type IV has been determined. See, Ma et al., (2002) Antimicrob. Agents Chemother. 46:1147-1152; Ito et al., (2001) Antimicrob. Agents Chemother. 45:1323-1336; Oliveira et al., (2001) Microb. Drug Resist. 7:349-360. Sequences from *S. aureus* strains CA05 and 8/6-3P, classified as SCCmec type IV, were nearly identical over 2000 nucleotides to that of type II SCCmec of *S. aureus* strain N315 (Ma et al., (2002) Antimicrob. Agents Chemother. 46:1147-1152; Ito et al., (2001) Antimicrob. Agents Chemother. 45:1323-1336).

Methods to detect and identify MRSA based on the detection of the mecA gene and *S. aureus*-specific chromosomal sequences have been described. See, Schuenck et al., Res. Microbiol., (2006), in press, Shittu et al., (2006), Diagn Microbiol Infect Dis. July 17, Grisold et al., (2006), Methods Mol. Biol. 345 : 79-89, Costa et al., (2005), Diag. Microbiol. and Infect. Dis, 51: 13-17, Mc Donald et al., (2005), J. Clin. Microbiol., 43: 6147-6149, Zhang et al., (2005), J. Clin. Microbiol. 43: 5026-5033, Hagen et al. (2005), Int J Med Microbiol. 295:77-86, Maes, et al. (2002) J. Clin. Microbiol. 40:1514-1517, Saito et al., (1995) J. Clin. Microbiol. 33:2498-2500; Ubukata et al., (1992) J. Clin. Microbiol. 30:1728-1733; Murakami et al., (1991) J. Clin. Microbiol. 29:2240-2244; Hiramatsu et al., (1992) Microbiol. Immunol. 36:445-453). Furthermore, Levi and Towner (2003), J. Clin. Microbiol., 41:3890-3892 and Poulsen et al. (2003), J Antimicrob Chemother., 51:419-421 describe detection of methicillin resistance in coagulase-negative Staphylococci and in *S. aureus* using the EVIGENE™ MRSA Detection kit.

However, because the mecA gene is widely distributed in both *S. aureus* and coagulase-negative staphylococci, each of the methods described above are incapable of discriminating between samples containing both methicillin-sensitive *S. aureus* ("MSSA") and methicillin-resistant coagulase-negative staphylococci, and samples that contain only MRSA or that have both methicillin-sensitive *S. aureus* and MRSA.

To address this problem, Hiramatsu et al. developed a PCR-based assay specific for MRSA that utilizes primers that hybridize to the right extremities of DNA of SCCmec types I-III in combination with primers specific to the *S. aureus* chromosome, which corresponds to the nucleotide sequence on the right side of the SCCmec integration site. (U.S. Pat. No. 6,156,507, hereinafter the "'507 patent"). More recently, Zhang et al., (2005), J. Clin. Microbiol. 43: 5026-5033, described a multiplex assay for subtyping SCCmec types Ito V MRSA. Nucleotide sequences surrounding the SCCmec integration site in other staphylococcal species (e.g., *S. epidermidis* and *S. haemolyticus*) are different from those found in *S. aureus*, therefore multiplex PCR assays that utilize oligonucleotides that hybridize to the right extremities of SCCmec and the *S. aureus* chromosome have the advantage of being specific for the detection of MRSA.

The PCR assay described in the '507 patent also led to the development of "MREP typing" (mec right extremity polymorphism) of SCCmec DNA (Ito et al., (2001) Antimicrob. Agents Chemother. 45:1323-1336; Hiramatsu et al., (1996) J. Infect. Chemother. 2:117-129). The MREP typing method takes advantage of the fact that the nucleotide sequences of the three MREP types differ at the right extremity of SCCmec DNAs adjacent to the integration site among the three types of SCCmec. Compared to type I, type III has a unique nucleotide sequence while type II has an insertion of 102 nucleotides to the right terminus of SCCmec. The MREP typing method described by Hiramatsu et al. uses the following nomenclature: SCCmec type I is MREP type i, SCCmec type II is MREP type ii, and SCCmec type III is MREP type iii. Hiramatsu later revised this nomenclature in view of the publication of the sequences of the genomes of strains N315 and Mu50, since the sequences revealed that SCCmec elements are located downstream of orfX. Consequently, MREP can now be referred to as MLEP (mec left extremity polymorphism) (Chongtrakool et al., (2006), Antimicrob. Agents Chemother. 50:1001-1012).

Recently, Chongtrakool et al. proposed replacing the SCCmec nomenclature with new nomenclature. Chongtrakool et al., (2006), Antimicrob. Agents Chemother. 50:1001-1012. Chongtrakool et al.'s proposed nomenclature is based on the structure of SCCmec elements and has three features. The first feature is a description of the SCC type and is defined by ccr type and mec class. The second feature is the description of the J regions (junkyard regions), which are part of the SCCmec element, located between and around the mec and ccr complexes. The third feature is the enumeration which allows the numbering of ccr type and J regions according to their time of identification.

As stated above, SCCmec types II and IV have the same nucleotide sequence to the right extremity. Consequently, the MREP (or MLEP according to recent revision) typing method described above cannot differentiate the SCCmec type IV described by Hiramatsu et al. (Ma et al., (2002) Antimicrob. Agents Chemother. 46:1147-1152) from SCCmec type II).

We recently described DNA sequences and regions in MRSA named MREJ. PCT Application No. PCT/CA02/00824. The phrase MREJ refers to the mec right extremity junction « mec right extremity junction ». MREJ's are approximately 1 kilobase (kb) in length and include sequences from the SCCmec right extremity as well as bacterial chromosomal DNA to the right of the SCCmec integration site. Importantly, MREJ sequences provide advantages over MREP/MLEP sequences in classifying MRSA in that MREJ/MLEJ sequences enable the differentiation between strains classified as SCCmec type II and SCCmec type IV. As discussed in PCT Application No. PCT/CA02/00824, the strains that Hiramatsu classified as MREP types i-iii fall under MREJ types i-iii according to the MREJ typing system. We recently identified novel MREJ types iv-xx, and developed nucleic acid assays with improved ubiquity capable of detection and identification of MRSA of MREJ types i-xx. (Huletsky et al., 2004, J. Clin. Microbiol. 42:1875-1884, International Patent Application PCT/CA02/00824, U.S. patent application Ser. No. 11/248,438). Based on the revision of MREP to MLEP, one can understand that previously called MREJ types could now be reclassified as MLEJ (mec left extremity junction). The skilled artisan will appreciate that any *S. aureus* and MRSA classification system is contemplated in the methods disclosed herein, as sequences can specifically detect *S. aureus* and identify those which are resistant to methicillin.

Maes et al. describe a PCR assay to discriminate *S. aureus* from coagulase negative Staphylococci and to determine methicillin resistance in blood cultures (Maes, et al. (2002) J. Clin. Microbiol. 40:1514-1517). The assay described in Maes et al. cannot distinguish MRSA from methicillin-resistant coagulase-negative Staphylococci.

Poulsen et al. describe detection of methicillin resistance in coagulase-negative Staphylococci and in *S. aureus* using the EVIGENE™ MRSA Detection kit. The assay described in Poulsen et al. cannot discriminate between a sample that has both methicillin-sensitive *S. aureus* and methicillin-resistant coagulase-negative staphylococci, and a sample that contains only MRSA or that has both methicillin-sensitive *S. aureus* and MRSA.

Accordingly, there remains a need for a rapid assay to detect and identify both MRSA and methicillin-sensitive *S. aureus* in the same reaction and to be able to distinguish *S. aureus* from coagulase-negative Staphylococci in the same reaction.

SUMMARY OF THE INVENTION

Disclosed herein are methods and compositions for specifically detecting the presence of a *Staphylococcus aureus* (*S. aureus*) strain and detecting the presence of a methicillin-resistant *S. aureus* (MRSA) strain from a clinical sample in a single assay. Also provided herein are methods and compositions for the specific detection of *S. aureus* from a sample.

Some embodiments relate to methods of detecting *S. aureus* and identifying the presence of MRSA from a sample that includes nucleic acids. In some embodiments, the sample can be contacted with at least one primer and or probe of at least 10 nucleotides that anneals under stringent conditions a *S. aureus*-specific sequence of the nuc gene, and at least one primer and/or probe specific for a MRSA strain. *S aureus* strains are rendered methicillin-resistant due to the presence of an SCCmec cassette containing a mecA gene that is inserted in bacterial nucleic acids. The insertion of the SCCmec cassette can generate a polymorphic right extremity junction (MREJ). The MRSA-specific primer(s) and/or probe(s) can anneal under stringent conditions to polymorphic MREJ nucleic acids, including, for example, MREJ types i to xx. *S. aureus*-specific and MRSA-specific primers anneal under conditions of, for example, 4 mM MgCl$_2$, 100 mM Tris (pH 8.3), 10 mM KCl, and 5 mM (NH$_4$)$_2$SO$_4$ at 59° C. The presence and/or amount of annealed probe(s), or amplification products produced through annealing of the primers to the nucleic acids, can be used as an indication of the presence and/or amount of *S. aureus* (MSSA and MRSA) and MRSA in the sample.

The at least one primer specific for a *S. aureus* strain can anneal under stringent conditions to the SEQ ID NO: 200, the complement thereof or any sequence which differs from SEQ ID NO: 200 by 1 to 20 nucleotides.

In some embodiments, the at least one primer and/or probe that anneals under stringent conditions to the *S. aureus* specific nuc sequence hybridizes under stringent conditions to one of the following SEQ ID NOs: 1, 2, 3, 4, 5, 6, 7, 8, 9, 10, 11, or 12 or the complement thereof. Preferably, the at least one primer and/or probe that anneals under stringent conditions to the *S. aureus* specific nuc sequence comprises, consists essentially of, or consists of one of the following SEQ ID NOs: 1, 2, 3, 4, 5, 6, 7, 8, 9, 10, 11, or 12.

In preferred embodiments, the *S. aureus*-specific primer(s) and/or probe(s) are at least 10 nucleotides in length, and anneal under stringent conditions to the nucleic acid of any one of SEQ ID NOs: 1 to 12 or the complement thereof.

In still more preferred embodiments, the sample is also contacted with a probe that anneals under stringent conditions to the nucleic acid of any one of SEQ ID NOs: 9, 10, 11, or 12, or the complement thereof. In some embodiments, the probe is a molecular beacon probe. Preferably, the probe comprises, consists essentially of, or consists of the sequence of SEQ ID NOs: 9, 10, 11, or 12.

In some embodiments, the method also includes adding internal control DNA to the sample, and at least one primer and/or probe that anneals under stringent conditions to the internal control DNA. For example, in some embodiments, the Internal Control can be a linearized 4.23 kb plasmid purified from *E. coli*. The internal control can be used to monitor the presence of inhibitory substances coming from a specimen.

The at least one primer specific for an MRSA strain can anneal under stringent conditions to the MREJ sequences of types i to xx, as defined in any one of SEQ ID NOs: 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, and 88, the complement thereof or any sequence which differs from SEQ ID NOs 14 to 88 by 1 to 20 nucleotides.

In preferred embodiments, *S. aureus*-specific and MRSA-specific primers and/or probes are chosen to anneal to the sample nucleic acids under the same annealing conditions. In more preferred embodiments, the primer(s) and/or probe(s) are placed altogether in the same physical enclosure.

In preferred embodiments, the MRSA-specific primer(s) and/or probe(s) are at least 10 nucleotides in length, and anneal under stringent conditions to the nucleic acid of any one of SEQ ID NOs: 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 15, 156, 157, 158, 159, 160, 161, 162, 163, 164, 165, 166, 167, 168, 169, 170, 171, 172, 173, 174, 175, 176, 177, 178, 179, 180, 181, 201 (types i-ix) 182, 183, 184, 195, 186, 187, 188, 189, 190, 191, 193, 194, 195, 196, 197, 198 (types x-xx) or 199 or the complement thereof. Preferably, the MRSA-specific primer(s) and/or probe(s) comprise, consist essentially of, or consist of the nucleic acid of any one of SEQ ID NOs: 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 15, 156, 157, 158, 159, 160, 161, 162, 163, 164, 165, 166, 167, 168, 169, 170, 171, 172, 173, 174, 175, 176, 177, 178, 179, 180, 181, 201 (types i-ix) 182, 183, 184, 195, 186, 187, 188, 189, 190, 191, 193, 194, 195, 196, 197, (types xi-xx) or 199. In some embodiments, MRSA-specific primers also include an oligonucleotide that hybridizes under stringent condition to orf22 of the *S. aureus* chromosome, wherein the primer can be used in an amplification reaction with SEQ ID NO: 197 to detect MREJ type x. In more preferred embodiments, the MRSA-specific primer(s) and/or probe(s) anneal under stringent conditions to the nucleic acid of any one of SEQ ID NOs: 99, 199, 144, 150, 155, and 163 or the complement thereof, such as a primer and/or probe that comprises, consists essentially of, or consists of the nucleic acid of any one of SEQ ID NOs: 99, 199, 144, 150, 155, and 163. In still more preferred embodiments, the sample is also contacted with a probe that anneals under stringent conditions to the nucleic acid of any one of SEQ ID NOs: 126, 128, 130 and 131, or the complement thereof. In some embodiments, the probe is a molecular beacon probe. Preferably, the probe comprises, consists essentially of, or consists of the nucleic acid of any one of SEQ ID NOs: 126, 128, 130 and 131.

In some embodiments, the sample and primer(s) and/or probe(s) described above are used in an amplification reaction, such as a PCR, LCR, NABSA, 3SR, SDA, bDNA, TMA, CPT, SPA, NDSA, rolling circle amplification, anchored-strand displacement amplification, solid-phase (immobilized) rolling circle amplification, or Q beta replicase amplification reaction.

Other aspects relate to the specific detection of an *S. aureus* strain in a sample that includes nucleic acids. At least one primer and/or probe that is specific for the nuc gene of *S. aureus* is provided. The primers and/or probe(s) include a nucleic acid that can anneal to at least 11 consecutive nucleotides of any one of the nucleic acids of SEQ ID NOs: 1, 2, 3, 4, 5, 6, 7, 8, 9, 10, 11, or 12, or the complement thereof, under stringent conditions, such as 50 mM KCl, 10 mM Tris-HCl (pH 9.0), 0.1% Triton X-100, 2.5 mM MgCl$_2$ at 59° C.; or 4 mM MgCl$_2$, 100 mM Tris (pH 8.3), 10 mM KCl, and 5 mM (NH$_4$)$_2$SO$_4$ at 59° C. The primer(s) and/or probe(s) are allowed to anneal to the nucleic acids of the sample. Annealed primer(s) and/or probe(s) indicate the presence of an *S. aureus* strain in the sample. The annealed primer(s) and/or probe(s) can be detected, and the presence and/or amount of annealed probe(s), the amount of an amplification product produced through annealing of the primers to the nucleic acids, indicates the presence and/or amount of *S. aureus* present in the sample.

In some embodiments, the sample and primer(s) and/or probe(s) described above are used in an amplification reaction, such as a PCR, LCR, NABSA, 3SR, SDA, bDNA, TMA, CPT, SPA, NDSA, rolling circle amplification, anchored-strand displacement amplification, solid-phase (immobilized) rolling circle amplification, or Q beta replicase amplification reaction.

In preferred embodiments, a primer pair including a first primer that anneals under stringent conditions to SEQ ID NO:1 or the complement thereof (such as a primer that comprises, consists essentially of, or consists of SEQ ID NO: 1), and a second primer that anneals under stringent conditions to SEQ ID NO: 6 (such as a primer that comprises, consists essentially of, or consists of SEQ ID NO: 6), or the complement thereof, is allowed to anneal to the nucleic acids of the sample. In more preferred embodiments, a probe that anneals under stringent conditions to SEQ ID NO:9 or 10 (such as a probe that comprises, consists essentially of, or consists of SEQ ID NO: 9 or 10), or the complement thereof, is also provided.

In other preferred embodiments, a primer pair including a first primer that anneals under stringent conditions to SEQ ID NO: 3 (such as a primer that comprises, consists essentially of, or consists of SEQ ID NO: 3) or the complement thereof, and a second primer that anneals under stringent conditions to SEQ ID NO: 8 (such as a primer that comprises, consists essentially of, or consists of SEQ ID NO: 8) or the complement thereof, is allowed to anneal to the nucleic acids of the sample. In more preferred embodiments, a probe that anneals under stringent conditions to SEQ ID NO: 11 or 12, (such as a primer that comprises, consists essentially of, or consists of SEQ ID NO: 11 or 12) or the complement thereof, is also provided.

In still other preferred embodiments, the sample is contacted with at least one primer pair, that includes a first primer and a second primer that anneal under stringent conditions to the nucleic acid sequence of at least one of the following pairs:
SEQ ID NOs: 1 and 5;
SEQ ID NOs: 1 and 6;
SEQ ID NOs: 2 and 5;
SEQ ID NOs: 2 and 6;
SEQ ID NOs: 3 and 7
SEQ ID NOs: 3 and 8;
SEQ ID NOs: 4 and 7; and
SEQ ID NOs: 4 and 8, or the complements thereof.

For example, in preferred embodiments, the sample is contacted with at least one primer pair that includes a first primer and a second primer that comprise, consist essentially of, or consist of the nucleic acid sequence of at least one of the following pairs:
SEQ ID NOs: 1 and 5;
SEQ ID NOs: 1 and 6;
SEQ ID NOs: 2 and 5;
SEQ ID NOs: 2 and 6;
SEQ ID NOs: 3 and 7
SEQ ID NOs: 3 and 8;
SEQ ID NOs: 4 and 7; and
SEQ ID NOs: 4 and 8.

In preferred embodiments, the sample is also contacted with at least one primer pair including a first primer and a second primer that anneal under stringent conditions to the nucleic acid sequence of at least one of the following pairs:
SEQ ID NOs: 99 and 199;
SEQ ID NOs: 99 and 144;
SEQ ID NOs: 99 and 150;
SEQ ID NOs: 99 and 155; and
SEQ ID NOs: 99 and 163, or the complement thereof.

For example, in some embodiments, the sample is contacted with at least one primer pair including a first primer and a second primer that comprise, consist essentially of, or consist of at least one of the following pairs:
SEQ ID NOs: 99 and 199;
SEQ ID NOs: 99 and 144;
SEQ ID NOs: 99 and 150;
SEQ ID NOs: 99 and 155; and
SEQ ID NOs: 99 and 163.

In preferred embodiments, the sample is contacted with a plurality of primer pairs, wherein the primers anneal under stringent conditions to the nucleic acid sequences of
SEQ ID NOs: 1 and 6
SEQ ID NOs: 99 and 199;
SEQ ID NOs: 99 and 144;
SEQ ID NOs: 99 and 150;
SEQ ID NOs: 99 and 155; and
SEQ ID NOs: 99 and 163, or the complements thereof, such as primer pairs that comprise, consist essentially of, or consist of the nucleic acid sequences of:
SEQ ID NOs: 1 and 6
SEQ ID NOs: 99 and 199;
SEQ ID NOs: 99 and 144;
SEQ ID NOs: 99 and 150;
SEQ ID NOs: 99 and 155; and
SEQ ID NOs: 99 and 163.

In other preferred embodiments, the sample is contacted with a plurality of primer pairs, wherein the primers anneal under stringent conditions to the nucleic acid sequences of SEQ ID NOs: 3 and 8
SEQ ID NOs: 99 and 199;
SEQ ID NOs: 99 and 144;
SEQ ID NOs: 99 and 150;
SEQ ID NOs: 99 and 155; and
SEQ ID NOs: 99 and 163, or the complements thereof, such as primer pairs that comprise, consist essentially of, or consist of the nucleic acid sequences of:
SEQ ID NOs: 3 and 8
SEQ ID NOs: 99 and 199;
SEQ ID NOs: 99 and 144;
SEQ ID NOs: 99 and 150;
SEQ ID NOs: 99 and 155; and
SEQ ID NOs: 99 and 163.

Preferably, the sample is also contacted with at least one probe that anneals under stringent conditions to the nucleic acid sequence of any one of SEQ ID NOs: 9, 10, 11, 12, 126, 128, 130 and 131 or the complement thereof, such as a probe that comprises, consists essentially of, or consists of the nucleic acid sequence of any one of SEQ ID NOs: 9, 10, 11, 12, 126, 128, 130 and 131.

Other aspects relate to oligonucleotides useful for the specific detection of S. aureus. Some embodiments provide oligonucleotides which anneal under stringent conditions with at least 11 consecutive nucleotides of the nucleic acid sequence of one of the following SEQ ID NOs: 1, 2, 3, 4, 5, 6, 7, 8, 9, 10, 11, or 12, such as nucleic acids that comprise, consist essentially of, or consist of one of SEQ ID NOs: 1, 2, 3, 4, 5, 6, 7, 8, 9, 10, 11, or 12.

Yet other aspects relate to kits for detecting the presence of an S. aureus strain in a sample that includes nucleic acids. The kit can include at least one oligonucleotide that anneals under stringent conditions to one of the following SEQ ID NOs: 1, 2, 3, 4, 5, 6, 7, 8, 9, 10, 11 or 12, or the complement thereof. For example, the kit can include at least one oligonucleotide that comprises, consists essentially of, or consists of SEQ ID NOs: 1, 2, 3, 4, 5, 6, 7, 8, 9, 10, 11 or 12. In preferred embodiments, the kit also includes at least one probe, wherein the probe can anneal to the nucleic acid sequence of SEQ ID NO: 9, 10, 11 or 12, or the complement thereof, under stringent conditions. In preferred embodiments, the probe can comprise, consist essentially of, or consist of SEQ ID NO: 9, 10, 11 or 12.

In preferred embodiments, the kit also includes at least one primer specific for an MRSA strain. S aureus strains are rendered methicillin-resistant due to the presence of an SCCmec insert containing a mecA gene that is inserted in bacterial nucleic acids. The insertion of the SCCmec insert can generate a polymorphic right extremity junction (MREJ). The MRSA-specific primer(s) and/or probe(s) can anneal under stringent conditions to polymorphic MREJ nucleic acids, including, for example, MREJ types i to xx.

In preferred embodiments, the kit includes at least one MRSA-specific oligonucleotide that anneals under stringent conditions to one of the following SEQ ID NOs: SEQ ID NOs: 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, and 88, or the complement thereof. For example, in some embodiments, a kit can contain at least one MRSA-specific oligonucleotide that is at least 10 nucleotides in length, and anneals under stringent conditions to the nucleic acid sequence of any one of the following SEQ ID NOs: 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 15, 156, 157, 158, 159, 160, 161, 162, 163, 164, 165, 166, 167, 168, 169, 170, 171, 172, 173, 174, 175, 176, 177, 178, 179, 180, 181, 201 (types i-ix) 182, 183, 184, 195, 186, 187, 188, 189, 190, 191, 193, 194, 195, 196, 197, (types xi-xx) or 199 or the complement thereof. In some embodiments, the MRSA-specific oligonucleotides can also include an oligonucleotide that hybridizes under stringent conditions to orf22 of the S. aureus chromosome, wherein the oligonucleotide can be used in an amplification reaction with SEQ ID NO: 197 to detect MREJ type x. Preferably, the MRSA-specific oligonucleotide can comprise, consist essentially of, or consist of any one of the following SEQ ID NOs: 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 15, 156, 157, 158, 159, 160, 161, 162, 163, 164, 165, 166, 167, 168, 169, 170, 171, 172, 173, 174, 175, 176, 177, 178, 179, 180, 181, 201 (types i-ix) 182, 183, 184, 195, 186, 187, 188, 189, 190, 191, 193, 194, 195, 196, 197, (types xi-xx) or 199.

In some embodiments, the kit contains a plurality of oligonucleotides that anneal under stringent conditions to SEQ ID NOs: 1, 6, 99, 144, 150, 155, and 163. For example, in preferred embodiments, the kit can contain a plurality of oligonucleotides that comprise, consist essentially of, or consist of SEQ ID NOs: 1, 6, 99, 144, 150, 155, and 163. In some embodiments, the kit contains a plurality of oligonucleotides that anneal under stringent conditions to SEQ ID NOs: 3, 8, 99, 144, 150, 155, and 163, such as a plurality of oligonucleotides that comprise, consist essentially of, or consist of SEQ ID NOs: 3, 8, 99, 144, 150, 155, and 163. Preferably, the kit also includes at least one probe that anneals under stringent conditions to the following SEQ ID NOs: 9, 10, 11, 12, 126, 128, 130 or 131, such as at least one probe that comprises, consists essentially of, or consists of SEQ ID NOs: 9, 10, 11, 12, 126, 128, 130 or 131.

DETAILED DESCRIPTION OF THE PREFERRED EMBODIMENTS

Figure 1A:
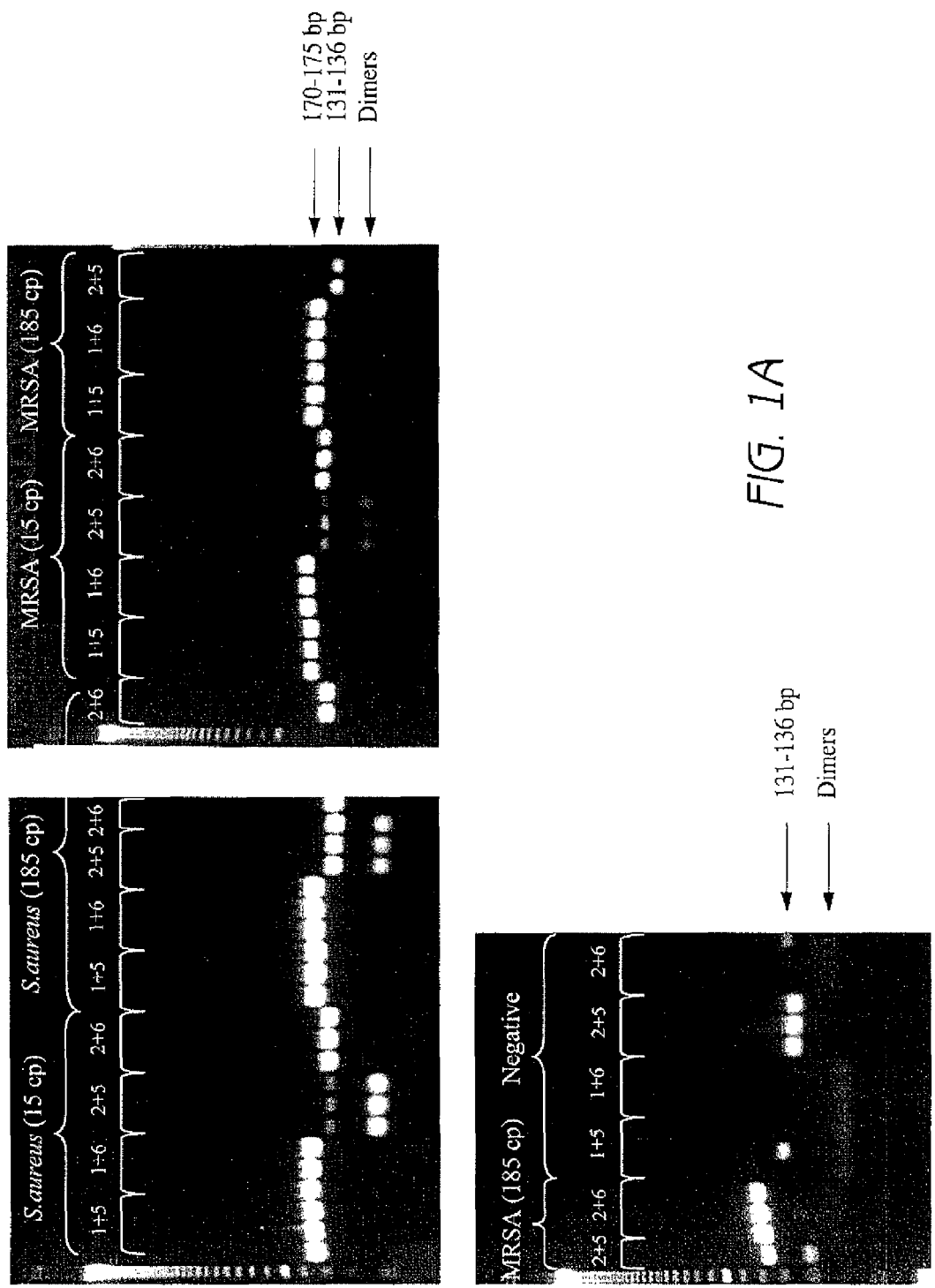
FIGS. 1A and 1B show photographs of agarose gels showing the products of PCR amplification reactions. The number of copies and source of template DNA are indicated (15 cp=15 copies; 185 cp=185 copies) (S. aureus=MSSA strain ATCC 25923; MRSA=MRSA strain ATCC 43300). Arrows indicate the PCR product sizes and primer dimers.

Methods and compositions disclosed herein relate to detection and/or quantification of S. aureus in a sample, and also relate to detection and/or quantification of a Staphylococcus

*aureus* (*S. aureus*) strain and identification a methicillin-resistant *S. aureus* strain from a sample in a single assay. The embodiments disclosed herein are useful for detection and/or quantification of *S. aureus* and MRSA from any type of sample, such as any clinical sample, any environmental sample, any microbial culture, any microbial colony, any tissue, and any cell line.

Staphylococci are Gram-positive cocci. *S. aureus* can be distinguished from other clinically relevant species of *Staphylococcus* by a positive result on the basis of their ability to clot blood plasma (the coagulase reaction) and their ability to form clumps in the presence of fibrinogen. *S. aureus*, as some other staphylococci has the ability to produce a thermostable nuclease (TNase), Becker et al., (2005), Diagn Microbiol Infect Dis., 51:237-244, Brakstad et al, (1995), APMIS, 103: 219-224, Chesneau, et al. (1993) Mol. Cell. Probes 7:301-310. Nevertheless, some nucleotide sequences in the gene encoding the nuclease are specific of *S. aureus* strains (Costa et al., (2005), Diag. Microbiol. and Infect. Dis, 51: 13-17, Mc Donald et al., (2005), J. Clin. Microbiol., 43: 6147-6149, Zhang, et al. (2004), J. Clin. Microbiol. 42:4947-4955; Maes, et al. (2002) J. Clin. Microbiol. 40:1514-1517), Methods of Detecting *S. aureus* or *S. aureus* and MRSA Some embodiments relate to methods of specifically detecting *S. aureus* in a sample. Disclosed herein are novel primers and/or probes (e.g., SEQ ID NOs: 1, 2, 3, 4, 5, 6, 7, 8, 9, 10, 11, and 12) that anneal to *S. aureus*-specific sequences of the nuc gene, exemplified by SEQ ID NO: 200, which are useful to distinguish *S. aureus* from other Staphylococci, as well as other TNase-producing species of bacteria. In some embodiments, at least one primer and/or probe that anneals under stringent conditions to SEQ ID NOs: 1, 2, 3, 4, 5, 6, 7, 8, 9, 10, 11, or 12, or the complement thereof is provided. For example, in some embodiments, the at least one primer and/or probe can comprise, consist essentially of, or consist of SEQ ID NOs: 1, 2, 3, 4, 5, 6, 7, 8, 9, 10, 11, or 12. The at least one primer is allowed to anneal to the nucleic acids of the sample, e.g., under standard PCR conditions or stringent conditions. The presence and/or amount of annealed probe(s) and/or the amount of an amplification product produced through annealing of the primers to the nucleic acids, is detected, thereby indicating the presence and/or amount of *S. aureus* present in the sample.

The term "consisting essentially of," when used in reference to nucleic acid can refer to the specified nucleic acid sequences, and can include any additional nucleotide that does not materially affect the basic and novel characteristics of the specified sequence. The term "consisting essentially of" also can refer to variants that are substantially similar to, and differ from a reference sequence in an inconsequential way as judged by examination of the sequence. For example, nucleic acid sequences encoding the same amino acid sequence are substantially similar despite differences in degenerate positions or modest differences in length or composition of any non-coding regions.

Primers and/or Probes and nucleotides

As used herein, the terms "primer" and "probe" are not limited to oligonucleotides or nucleic acids, but rather encompass molecules that are analogs of nucleotides, as well as nucleotides. Nucleotides and polynucleotides, as used herein shall be generic to polydeoxyribonucleotides (containing 2-deoxy-D-ribose), to polyribonucleotides (containing D-ribose), to any other type of polynucleotide which is an N- or C-glycoside of a purine or pyrimidine base, and to other polymers containing normucleotidic backbones, for example, polyamide (e.g., peptide nucleic acids (PNAs)) and polymorpholino (commercially available from the Anti-Virals, Inc., Corvallis, Oreg., as NEUGENE™ polymers), and other synthetic sequence-specific nucleic acid polymers providing that the polymers contain nucleobases in a configuration which allows for base pairing and base stacking, such as is found in DNA and RNA.

The terms nucleotide and polynucleotide include, for example, 3'-deoxy-2',5'-DNA, oligodeoxyribonucleotide N3'→P5' phosphoramidates, 2'-O-alkyl-substituted RNA, double- and single-stranded DNA, as well as double- and single-stranded RNA, DNA:RNA hybrids, and hybrids between PNAs and DNA or RNA. The terms also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides will also include modifications on the sugar moiety, e.g., wherein one or more of the hydroxyl groups are replaced with a halogen, an aliphatic group, or are functionalized as ethers, amines, or the like. Other modifications to nucleotides or polynucleotides involve rearranging, appending, substituting for, or otherwise altering functional groups on the purine or pyrimidine base which form hydrogen bonds to a respective complementary pyrimidine or purine. The resultant modified nucleotide or polynucleotide may form a base pair with other such modified nucleotidic units but not with A, T, C, G or U. For example, guanosine (2-amino-6-oxy-9-beta.-D-ribofuranosyl-purine) may be modified to form isoguanosine (2-oxy-6-amino-9-.beta.-D-ribofuranosyl-purine). Such modification results in a nucleoside base which will no longer effectively form a standard base pair with cytosine. However, modification of cytosine (1-.beta.-D-ribofuranosyl-2-oxy-4-amino-pyrimidine) to form isocytosine (1-.beta.-D-ribofuranosyl-2-amino-4-oxy-pyrimidine) results in a modified nucleotide which will not effectively base pair with guanosine but will form a base pair with isoguanosine. Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al. (1993) J. Am. Chem. Soc. 115:4461-4467 and references cited therein; and isoguanine nucleotides may be prepared using the method described by Switzer et al. (1993), supra, and Mantsch et al. (1993) Biochem. 14:5593-5601, or by the method described U.S. Pat. No. 5,780,610 to Collins et al. The non-natural base pairs referred to as κ and π., may be synthesized by the method described in Piccirilli et al. (1990) Nature 343:33-37 for the synthesis of 2,6-diaminopyrimidine and its complement (1-methylpyrazolo[4,3]-pyrimidine-5,7-(4H, 6H)-dione. Other such modified nucleotidic units which form unique base pairs have been described in Leach et al. (1992) J. Am. Chem. Soc. 114:3675-3683 and Switzer et al., supra, or will be apparent to those of ordinary skill in the art.

Primers and/or probes are preferably between 10 and 45 nucleotides in length. For example, the primers and or probes can be at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more nucleotides in length. Primers and/or probes can be provided in any suitable form, included bound to a solid support, liquid, and lyophilized, for example.

Annealing and Specific Binding

Binding or annealing of the primers and/or probes to target nucleic acid sequences is accomplished through hybridization. It will be appreciated by one skilled in the art that specific hybridization is achieved by selecting sequences which are at least substantially complementary to the target or reference nucleic acid sequence. This includes base-pairing of the oligonucleotide target nucleic acid sequence over the entire length of the oligonucleotide sequence. Such sequences can be referred to as "fully complementary" with respect to each other. Where an oligonucleotide is referred to as "substantially complementary" with respect to a nucleic acid sequence herein, the two sequences can be fully complementary, or they may form mismatches upon hybridization, but retain the ability to hybridize under stringent conditions or standard PCR conditions as discussed below.

A positive correlation exists between probe length and both the efficiency and accuracy with which a probe will anneal to a target sequence. In particular, longer sequences have a higher melting temperature ($T_m$) than do shorter ones, and are less likely to be repeated within a given target sequence, thereby minimizing promiscuous hybridization.

As used herein, "$T_m$" and "melting temperature" are interchangeable terms which refer to the temperature at which 50% of a population of double-stranded polynucleotide molecules becomes dissociated into single strands. Formulae for calculating the $T_m$ of polynucleotides are well known in the art. For example, the $T_m$ may be calculated by the following equation: $T_m=69.3+0.41$ x.(G+C)%–6–50/L, wherein L is the length of the probe in nucleotides. The $T_m$ of a hybrid polynucleotide may also be estimated using a formula adopted from hybridization assays in 1 M salt, and commonly used for calculating $T_m$ for PCR primers: [(number of A+T)× 2° C.+(number of G+C)×4° C.]. See, e.g., C. R. Newton et al. PCR, 2nd Ed., Springer-Verlag (New York: 1997), p. 24. Other more sophisticated computations exist in the art, which take structural as well as sequence characteristics into account for the calculation of $T_m$. A calculated $T_m$ is merely an estimate; the optimum temperature is commonly determined empirically.

Primer or probe sequences with a high G+C content or that comprise palindromic sequences tend to self-hybridize, as do their intended target sites, since unimolecular, rather than bimolecular, hybridization kinetics are generally favored in solution. However, it is also important to design a probe that contains sufficient numbers of G:C nucleotide pairings since each G:C pair is bound by three hydrogen bonds, rather than the two that are found when A and T (or A and U) bases pair to bind the target sequence, and therefore forms a tighter, stronger bond. Preferred G+C content is about 50%.

Hybridization temperature varies inversely with probe annealing efficiency, as does the concentration of organic solvents, e.g., formamide, which might be included in a hybridization mixture, while increases in salt concentration facilitate binding. Under stringent annealing conditions, longer hybridization probes, or synthesis primers, hybridize more efficiently than do shorter ones, which are sufficient under more permissive conditions. Preferably, stringent hybridization is performed in a suitable buffer under conditions that allow the reference or target nucleic acid sequence to hybridize to the probes. Stringent hybridization conditions can vary (for example from salt concentrations of less than about 1 M, more usually less than about 500 mM and preferably less than about 200 mM) and hybridization temperatures can range (for example, from as low as 0° C. to greater than 22° C., greater than about 30° C. and (most often) in excess of about 37° C. depending upon the lengths and/or the nucleic acid composition of the probes. Stringent hybridization temperatures for PCR range from 40 and 75° C., preferably between 45 and 70° C., depending on lengths and compositions of primers. Longer fragments may require higher hybridization temperatures for specific hybridization. As several factors affect the stringency of hybridization, the combination of parameters is more important than the absolute measure of a single factor. Accordingly, by way of example, the term "stringent hybridization conditions" may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. For additional details and explanation of stringency of hybridization reactions, see Ausubel et al., Current Protocols in Molecular Biology, Wiley Interscience Publishers, (1995). For example, the term "stringent conditions" encompasses standard PCR conditions, as described below.

For a review of PCR technology, including standard PCR conditions, applied to clinical microbiology, see DNA Methods in Clinical Microbiology, Singleton P., published by Dordrecht; Boston: Kluwer Academic, (2000) Molecular Cloning to Genetic Engineering White, B. A. Ed. in *Methods in Molecular Biology* 67: Humana Press, Totowa (1997) and "PCR Methods and Applications", from 1991 to 1995 (Cold Spring Harbor Laboratory Press). Non-limiting examples of "PCR conditions" include the conditions disclosed in the references cited herein, and also in the examples below, such as, for example, 50 mM KCl, 10 mM Tris-HCl (pH 9.0), 0.1% Triton X-100, 2.5 mM MgCl$_2$, with an annealing temperature of 72° C.; or 4 mM MgCl$_2$, 100 mM Tris, pH 8.3, 10 mM KCl, 5 mM (NH$_4$)$_2$SO$_4$, 0.15 mg BSA, 4% Trehalose, with an annealing temperature of 59° C., or 50 mM KCl, 10 mM Tris-HCl (pH 9.0), 0.1% Triton X-100, 2.5 mM MgCl$_2$, with an annealing temperature of 55° C.

As used herein, when used to describe primers and/or probes, the terms "specific" or "species-specific" refer to primers and/or probes which hybridize or anneal under stringent conditions and/or standard PCR conditions to nucleic acids of a specified species or type (e.g. *S. aureus* or MRSA), and which do not substantially anneal or hybridize under the same conditions to unrelated nucleic acids, such as nucleic acids other than the specified species or MREJ type.

In a preferred embodiment, the probes or primers described herein hybridize under stringent conditions to target sequences (e.g., S. aureus specific nuc sequences or MREJ sequences). In other preferred embodiments, the primers or probes described herein exhibit 100% complementarity over at least 10 to 45 nucleotides in length. For example, the primers and or probes exhibit complementarity over at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more nucleotides to the target sequence. In some embodiments, the primers or probes exhibit 100% complementarity to the target sequence over 10 to 45 consecutive nucleotides in all but at least 1 position (e.g., the primer and/or probe contains a mismatch), 2 positions, 3 positions, 4 positions, 5 positions, 6 positions, 7 positions or more.

Probes or primers that include sequences that can hybridize as described herein and that also include a portion that does not hybridize to the target sequence (e.g., a tag or a marker), are also contemplated. For example, in some embodiments, the primer and/or probe can contain a detectable moiety, such as a fluorescent moiety, or any other detectable marker, such as those described below. In some embodiments, the primer and/or probe may contain nucleic acid or other molecular components that facilitate subsequent manipulations, such as polymerization reactions, or enzymatic reactions such as digestion with restriction endonucleases, and the like, or that couple the primer and/or probe to a solid support.

Amplification and Detection

In the methods described herein, detection of annealed primers and/or probes can be direct or indirect. For example, probes can be annealed to the sample being tested, and detected directly. On the other hand, primers can be annealed to the sample being tested, followed by an amplification step. The amplified products can be detected directly, or through detection of probes that anneal to the amplification products.

In preferred embodiments, an amplification and/or detection step follows the annealing step. In other preferred embodiments, detection occurs during the annealing step. Any type of nucleic acid amplification technology can be used in the methods described herein. Non-limiting examples of amplification reactions that can be used in the methods described herein include but are not restricted to: polymerase chain reaction (PCR) (See, PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y. (Innis)), ligase chain reaction (LCR) (See, Wu (1989) *Genomics* 4:560; Landegren (1988) *Science* 241:1077; Barringer (1990) Gene 89:117), nucleic acid sequence-based amplification (NASBA), self-sustained sequence replication (3SR) (See, Guatelli (1990) *Proc. Natl. Acad. Sci. USA,* 87:1874), strand displacement amplification (SDA), branched DNA signal amplification bDNA, transcription-mediated amplification (TMA)(See, Kwoh (1989) *Proc. Natl. Acad. Sci. USA* 86:1173), cycling probe technology (CPT), nested PCR, multiplex PCR, solid phase amplification (SPA), nuclease dependent signal amplification (NDSA), rolling circle amplification technology (RCA), Anchored strand displacement amplification, solid-phase (immobilized) rolling circle amplification, Q Beta replicase amplification and other RNA polymerase mediated techniques (e.g., NASBA, Cangene, Mississauga, Ontario). These and other techniques are also described in Berger (1987) *Methods Enzymol.* 152:307-316; Sambrook, Ausubel, Mullis (1987) U.S. Pat. Nos. 4,683,195 and 4,683,202; Amheim (1990) *C&EN* 36-47; Lomell *J. Clin. Chem.,* 35:1826 (1989); Van Brunt, *Biotechnology,* 8:291-294 (1990); Wu (1989) *Gene* 4:560; Sooknanan (1995) *Biotechnology* 13:563-564.

In preferred embodiments, PCR is used to amplify nucleic acids in the sample. During DNA amplification by PCR, two oligonucleotide primers binding respectively to each strand of the heat-denatured target DNA from the microbial genome, are used to amplify exponentially in vitro the target DNA. Successive thermal cycles allow denaturation of the DNA, annealing of the primers and synthesis of new targets at each cycle. (Persing et al, (1993), Diagnostic Molecular Microbiology: Principles and Applications, American Society for Microbiology, Washington, D.C.).

The skilled artisan will appreciate that standard amplification protocols may be modified to improve nucleic acid amplification efficiency, including modifications to the reaction mixture. (Ralser et al., (2006), *Biochem Biophys Res Commun.,* 347:747-51, Kang et al., (2005), J Biochem Biophys Methods. (2005), 64:147-51, Chakrabarti and Schutt, (2002), Biotechniques, 32:866-874; Al-Soud and Radstrom, (2000), J. Clin. Microbiol., 38:4463-4470; Al-Soud and Radstrom, 1998, Appl. Environ. Microbiol., 64:3748-3753; Wilson, 1997, Appl. Environ. Microbiol., 63:3741-3751). Such modifications of the amplification reaction mixture include but are not limited to the use of various polymerases or the addition of nucleic acid amplification facilitators such as betaine, BSA, sulfoxides, protein gp32, detergents, cations, and tetramethylamonium chloride.

Detection of amplified nucleic acids may include any real-time or post-amplification technologies known to those skilled in the art. Classically, the detection of PCR amplification products is performed by standard ethidium bromide-stained agarose gel electrophoresis, however, the skilled artisan will readily appreciate that other methods for the detection of specific amplification products, which may be faster and more practical for routine diagnosis, may be used, such as those described in co-pending patent application WO01/23604 A2. Amplicon detection may also be performed by solid support or liquid hybridization using species-specific internal DNA probes hybridizing to an amplification product. Such probes may be generated from any sequence from the MREJ or nuc nucleic acid sequences provided herein, and designed to specifically hybridize to DNA amplification products produced utilizing the methods disclosed herein. Alternatively, amplicons can be characterized by sequencing. See, e.g., co-pending patent application WO01/23604 A2 for examples of detection and sequencing methods.

Other non-limiting examples of nucleic acid detection technologies that can be used in the embodiments disclosed herein include, but are not limited to the use of fluorescence resonance energy transfer (FRET)-based methods such as adjacent hybridization of probes (including probe-probe and probe-primer methods) (See, J. R. Lakowicz, "Principles of Fluorescence Spectroscopy," Kluwer Academic/Plenum Publishers, New York, 1999)., TaqMan probe technology (See, European Patent EP 0 543 942), molecular beacon probe technology (See, Tyagi et al., (1996) *Nat. Biotech.* 14:303-308.), Scorpion probe technology (See, Thewell (2000), *Nucl. Acids Res.* 28:3752), nanoparticle probe technology (See, Elghanian, et al. (1997) *Science* 277:1078-1081.) and Amplifluor probe technology (See, U.S. Pat. Nos. 5,866,366; 6,090,592; 6,117,635; and 6,117,986).

In preferred embodiments, molecular beacons are used for detection of the target nucleic acids. Molecular beacons are single stranded oligonucleotides that, unless bound to target, exist in a hairpin conformation. The 5' end of the oligonucleotide contains a fluorescent dye. A quencher dye is attached to the 3' end of the oligonucleotide. When the beacon is not bound to target, the hairpin structure positions the fluorophore and quencher in close proximity, such that no fluorescence can be observed. Once the beacon hybridizes with target, however, the hairpin structure is disrupted, thereby separating the fluorophore and quencher and enabling detection of fluorescence. (See, Kramer F R., 1996, Nat Biotechnol 3:303-8.). Other detection methods include target gene nucleic acids detection via immunological methods, solid phase hybridization methods on filters, chips or any other solid support. In these systems, the hybridization can be monitored by any suitable method known to those skilled in the art, including fluorescence, chemiluminescence, potentiometry, mass spectrometry, plasmon resonance, polarimetry, colorimetry, flow cytometry or scanometry. Nucleotide sequencing, including sequencing by dideoxy termination or sequencing by hybridization (e.g. sequencing using a DNA chip) represents another method to detect and characterize target nucleic acids, such as nuc or MREJ nucleic acid sequences.

Methods

In preferred embodiments, methods to detect a S. aureus strain in a sample include the step of providing a primer pair, with a first and a second primer. The first and the second primer can anneal under stringent conditions to at least one of SEQ ID NOs: 1, 2, 3, 4, 5, 6, 7, 8, 9, 10, 11, or 12, or the complements thereof, such as primers that comprise, consist essentially of, or consist of SEQ ID NOs: 1, 2, 3, 4, 5, 6, 7, 8, 9, 10, 11, or 12. In preferred embodiments, the primer pairs comprise first and second primers that anneal under stringent conditions to SEQ ID NOs: 1 and 5; SEQ ID NOs: 1 and 6; SEQ ID NOs: 2 and 5, SEQ ID NOs: 2 and 6; SEQ ID NOs: 3 and 7; SEQ ID NOs: 3 and 8; SEQ ID NOs: 4 and 7; or SEQ ID NOs: 4 and 8, or the complements thereof. For example, in preferred embodiments, the primer pairs can comprise, consist essentially of, SEQ ID NOs: 1 and 5; SEQ ID NOs: 1 and 6; SEQ ID NOs: 2 and 5, SEQ ID NOs: 2 and 6; SEQ ID NOs: 3 and 7; SEQ ID NOs: 3 and 8; SEQ ID NOs: 4 and 7; or SEQ ID NOs: 4 and 8. The sample can be contacted with and allowed to anneal to the primer pair. Preferably, an amplification reaction (e.g., PCR) is performed with the annealed primer pair to amplify S. aureus-specific nuc sequences using the techniques described herein. Amplification products can then be detected using any of the methods described herein.

In some embodiments, the primer pair includes a first primer that anneals under stringent conditions to SEQ ID NO: 1 or the complement thereof, and a second primer that anneals under stringent conditions to SEQ ID NO: 6, or the complement thereof, such as a primer pair that comprises, consists essentially of, or consists of SEQ ID NO: 1 and SEQ ID NO: 6. In some embodiments, the primer pair is used to amplify nuc sequences present in the sample. Optionally, a probe that anneals under stringent conditions to SEQ ID NO: 9 or 10 or the complement thereof is also provided, for example, a probe that comprises, consists essentially of, or consist of SEQ ID NO: 9 or 10. In some embodiments, the probe is a molecular beacon probe, and the resulting amplification product can be detected by the probe.

In other preferred embodiments, a first primer that anneals under stringent conditions to SEQ ID NO: 3 or the complement thereof and a second primer that anneals under stringent conditions to SEQ ID NO: 8, or the complement thereof, are provided, such as a primer pair that comprises, consists essentially of, or consists of SEQ ID NO: 3 and SEQ ID NO: 8. In some embodiments, the primer pair is used to amplify nuc sequences present in the sample. Optionally, a probe that anneals under stringent conditions to SEQ ID NO: 11 or 12 or the complement thereof is also provided for example, a probe that comprises, consists essentially of, or consist of SEQ ID NO: 11 or 12. In some embodiments, the probe is a molecular beacon probe.

Other aspects of the invention relate to methods and compositions for detecting the presence of S. aureus strains and identifying MRSA strains from a sample in a single assay or reaction. The term "single assay" or "single reaction" is intended to refer to the situation in which steps to detect S. aureus and steps to detect MRSA are performed simultaneously, or at substantially the same time, for example in the same physical enclosure. The skilled artisan will appreciate, however, that steps to detect S. aureus and steps to detect MRSA can also be performed sequentially. In preferred embodiments, S. aureus and MRSA are simultaneously detected, for example in a multiplex PCR reaction.

Some embodiments involve the steps of contacting the sample with at least one primer and/or probe that anneals under stringent conditions to a species-specific sequence of the nuc gene of S. aureus, and contacting the sample with at least one primer and/or probe that anneals under stringent conditions to a sequence that is specific to MREJ sequences of MRSA strains.

The MRSA-specific primer(s) and/or probe(s) can anneal under stringent conditions to polymorphic MREJ nucleic acids, including, for example, MREJ types i to xx. The phrase MREJ refers to the mec right extremity junction « mec right extremity junction» . MREJ's are approximately 1 kilobase (kb) in length and include sequences from the SCCmec right extremity as well as bacterial chromosomal DNA to the right of the SCCmec integration site (See, Huletsky et al., (2004) J. Clin. Microbiol., 42:1875-1884). Based on the determination of the whole-genome sequences of strain N315 and Mu50, the nomenclature was recently reviewed because SCCmec elements are located downstream (and not upstream) of orfX. Consequently, MREP (Mec Right Extremity Polymorphism) is also referred to as MLEP (Mec Left Extremity Polymorphism). By a similar token, MREJ types can be referred to as MLEJ (mec left extremity junction). (Chongtrakool et al., (2006), Antimicrob. Agents Chemother. 50:1001-1012). Nevertheless, any equivalent way to classify S. aureus and namely MRSA strains will be under the scope of this patent, since sequences will be able to specifically detect S. aureus and to identify those which are resistant to methicillin.

Non-limiting examples MREJ type i to xx sequences are listed in SEQ ID NOs: 14-88. Accordingly, in some embodiments, in addition to at least one S. aureus-specific nuc primer and/or probe, (e.g., an oligonucleotide that hybridizes under stringent conditions to one of the following SEQ ID NO: 200, the complement thereof or any sequence which differs from SEQ ID NO: 200 by 1 to 20 nucleotides, at least one primer and/or probe that specifically anneals under stringent conditions to at least one MREJ sequence of MREJ types i-xx (e.g., SEQ ID NOs: 14-88) or the complement thereof is provided. Exemplary primers and probes and combinations of primers and probes useful for the detection of MRSA of MREJ types i-xx are found in, for example, International Patent Application PCT/CA02/00824, and in U.S. patent application Ser. No. 11/248,438, hereby expressly incorporated by reference in their entireties. For example, in some embodiments, the at least one MRSA-specific primer and/or probe provided in the method is at least 10 nucleotides in length, and can hybridize under stringent conditions to one of the following SEQ ID NOs: 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 15, 156, 157, 158, 159, 160, 161, 162, 163, 164, 165, 166, 167, 168, 169, 170, 171, 172, 173, 174, 175, 176, 177, 178, 179, 180, 181, 201 (MREJ types i-ix) 182, 183, 184, 195, 186, 187, 188, 189, 190, 191, 193, 194, 195, 196, 197, (MREJ types xi-xx) or 199, or the complement thereof. For example, the MRSA-specific primers can comprise, consist essentially of, or consist of one of the following SEQ ID NOs: 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 15, 156, 157, 158, 159, 160, 161, 162, 163, 164, 165, 166, 167, 168, 169, 170, 171, 172, 173, 174, 175, 176, 177, 178, 179, 180, 181, 201 (MREJ types i-ix) 182, 183, 184, 195, 186, 187, 188, 189, 190, 191, 193, 194, 195, 196, 197, (MREJ types xi-xx) or 199. nuc-specific primers and/or probes (e.g., comprising an oligonucleotide that hybridizes under stringent conditions to one of the following SEQ ID NOs: 1, 2, 3, 4, 5, 6, 7, 8, 9, 10, 11, or 12 or the complement thereof, such as oligonucleotides that comprise, consist essentially of, or consist of one of the following SEQ ID NOs: 1, 2, 3, 4, 5, 6, 7, 8, 9, 10, 11, or 12) and MRSA (i.e., MREJ)-specific primers and/or probes (e.g., comprising an oligonucleotide that hybridizes under stringent conditions to SEQ ID NOs: 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 15, 156, 157, 158, 159, 160, 161, 162, 163, 164, 165, 166, 167, 168, 169, 170, 171, 172, 173, 174, 175, 176, 177, 178, 179, 180, 181, 201 (types i-ix) 182, 183, 184, 195, 186, 187, 188, 189, 190, 191, 193, 194, 195, 196, 197, (types xi-xx) or 199, or the complement thereof) are annealed to the nucleic acids of the sample, and the presence of annealed primers and/or probes, or amplification products produced therefrom, is detected, indicating the presence and/or amount of S. aureus as well as MRSA. For example, in some embodiments, the sample is contacted with at least one primer pair comprising oligonucleotides that hybridize under stringent conditions to SEQ ID NOs: 92 and 82; 92 and 83; 92 and 84; 104 and 86; 104 and 87; 104 and 88; 99 and 89; 99 and 199 (for the detection of MREJ type i); SEQ ID NOs: 92 and 82; 92 and 129; 92 and 130; 93 and 83; and 92 and 84; 99 and 89; 99 and 199 (for the detection of MREJ type ii); SEQ ID NOs: 92 and 136; 92 and 137; 92 and 138; 99 and 202; 99 and 144 (for the detection of MREJ type iii); SEQ ID NOs: 92 and 141; 99 and 105; 99 and 150 (for the detection of MREJ type iv); SEQ ID NOs: 92 and 146; 99 and 196; 99 and 155 (for the detection of MREJ type v); SEQ ID NOs: 92 and 152; 99 and 161; (for the detection of MREJ type vi); SEQ ID NOs: 92 and 153; 92 and 154; 99 and 162; 99 and 163 (for the detection of MREJ type vii); SEQ ID NOs: 92 and 162; 92 and 163; 99 and 170 (for the detection of MREJ type viii); SEQ ID NOs: 92 and 168; 99 and 177 (for the detection of MREJ type ix); SEQ ID NOs: 197 and an oligonucleotide that hybridizes under stringent conditions to orf22 (for the detection of MREJ type x); SEQ ID NOs: 189 and 106; 189 and 99; 189 and 190; 189 and 109 (for the detection of MREJ type xi); SEQ ID NOs: 194 and 106; 194 and 99; 104 and 191; 194 and 109 (for the detection of MREJ type xii); SEQ ID NOs: 177 and 106; 177 and 99; 177 and 190; and 177 and 109 (for the detection of MREJ type xiii); SEQ ID NOs: 177 and 106; 177 and 99; 177 and 193; 177 and 109 (for the detection of MREJ type xiv); SEQ ID NOs: 184 and 106; 108 and 99; 184 and 191; 184 and 191 (for the detection of MREJ type xv); SEQ ID NOs: 89 and 109 (for the detection of MREJ type xvi); SEQ ID NOs: 185 and 106; 185 and 99; 185 and 191; 185 and 109 (for the detection of MREJ type xvii); SEQ ID NOs: 186 and 106; 186 and 99; 186 and 193; 186 and 109 (for the detection of MREJ type xviii); SEQ ID NOs: 187 and 106; 107 and 99; 187 and 913; 187 and 109 (for the detection of MREJ type xix); SEQ ID NOs: 188 and 106; 188 and 99; 188 and 913; and 188 and 109 (for the detection of MREJ type xx), or the complement thereof.

The most clinically relevant MRSA strains have MREJ types i, ii, iii, iv, v, and vii. Accordingly, preferred methods and compositions relate to the detection of S. aureus and MRSA of MREJ types i-v and vii in a sample. At least one S. aureus-specific nuc-specific primer and/or probe is provided, and primers and/or probes useful for the specific detection of MREJ types i, ii, iii, iv, v and vii are provided. For example, in some embodiments, primers and/or probes that hybridize under stringent conditions to each of the following SEQ ID NOs or the complements thereof are provided: SEQ ID NOs: 99, 199, 144, 150, 155, and 163, such as primers and/or probes that comprise, consist essentially of, or consist of at least one of the following SEQ ID NOs: 99, 199, 144, 150, 155, and 163. Optionally, at least one probe comprising an oligonucleotide that hybridizes under stringent conditions to SEQ ID NOs: 126, 128, 130 and 131 or the complement thereof is provided, for the detection of MREJ sequences of types i, ii, iii, iv, v and vii. For example, at least one primer and/or probe that comprises, consists essentially of, or consists of at least one of the following SEQ ID NOs: 126, 128, 130 and 131, is provided.

In other preferred embodiments, the at least one primer(s) and/or probe(s) that anneal to MREJ sequences comprises a pair of oligonucleotides that hybridize under stringent conditions to SEQ ID NOs: 99 and 199 (for the detection of type i and type ii MREJ); SEQ ID NOs: 99 and 144 (for the detection of type iii MREJ); SEQ ID NOs: 99 and 150 (for the detection of type iv MREJ); SEQ ID NOs: 99 and 155 (for the detection of type v MREJ); and SEQ ID NOs: 99 and 163 (for the detection of type vii MREJ), or the complement thereof. Optionally oligonucleotides that hybridize under stringent conditions to each of SEQ ID NOs: 99 and 199 (for the detection of type i and type ii MREJ); SEQ ID NOs: 99 and 144 (for the detection of type iii MREJ); SEQ ID NOs: 99 and 150 (for the detection of type iv MREJ); SEQ ID NOs: 99 and 155 (for the detection of type v MREJ); and SEQ ID NOs: 99 and 163 (for the detection of type vii MREJ) are provided. Optionally, the sample is also contacted with a probe comprising an oligonucleotide that hybridizes under stringent conditions to the nucleic acid of SEQ ID NOs: 9, 10, 11, 12, 126, 128, 130 or 131, for the detection of MREJ sequences, or SEQ ID NOs: 9, 10, 11, and 12 for the detection of S. aureus nuc, or the complements thereof.

In preferred embodiments, the nuc-specific primer(s) and/or probe(s) comprise at least one first primer pair that hybridizes under stringent conditions to the following oligonucleotide pairs or the complements thereof: SEQ ID NOs: 1 and 5; SEQ ID NOs: 1 and 6; SEQ ID NOs: 2 and 5, SEQ ID NOs: 2 and 6; SEQ ID NOs: 3 and 7; SEQ ID NOs: 3 and 8; SEQ ID NOs: 4 and 7; or SEQ ID NOs: 4 and 8; for the detection of S. aureus in a sample. For example, in some embodiments, the nuc-specific primer(s) and/or probe(s) comprise at least one first primer pair that comprises, consists essentially of, or consists of: SEQ ID NOs: 1 and 5; SEQ ID NOs: 1 and 6; SEQ ID NOs: 2 and 5, SEQ ID NOs: 2 and 6; SEQ ID NOs: 3 and 7; SEQ ID NOs: 3 and 8; SEQ ID NOs: 4 and 7; or SEQ ID NOs: 4 and 8. Optionally, in embodiments where the sample is contacted with a first primer pair comprising oligonucleotides that hybridize under stringent conditions to SEQ ID NOs: 1 and 5, or 1 and 6, or the complements thereof, (e.g., oligonucleotides that comprise, consist essentially of, or consist of SEQ ID NOs: 1 and 5, or SEQ ID NOs: 1 and 6), the sample can also be contacted with a probe comprising an oligonucleotide that hybridizes under stringent conditions to SEQ ID NO: 9 (e.g., SEQ ID NO: 10) or the complement thereof. Optionally, in embodiments where the sample is contacted with a first primer pair comprising oligonucleotides that hybridize under stringent conditions to SEQ ID NOs: 3 and 7, or SEQ ID NOs: 3 and 8, or the complements thereof, (e.g., oligonucleotides that comprise, consist essentially of, or consist of SEQ ID NOs: 3 and 7, or SEQ ID NOs: 3 and 8), the sample can also be contacted with a probe comprising an oligonucleotide that hybridizes under stringent conditions SEQ ID NO: 11 (e.g., SEQ ID NO: 12) or the complement thereof. Preferably, the first primer pair comprises oligonucleotides that hybridize under stringent conditions to SEQ ID NOs: 1 and 6; or SEQ ID NOs: 3 and 8 or the complements thereof.

Optionally, the sample is also contacted with at least one probe comprising an oligonucleotide that hybridizes under stringent conditions to SEQ ID NOs: 9, 10, 11, 12, for the detection of S. aureus nuc sequences, or to SEQ ID NOs: 126, 128, 130 or 131, for the detection of MREJ sequences, or the complement thereof, e.g., at least one probe that comprises, consists essentially of, or consists of SEQ ID NOs: 9, 10, 11, 12, 126, 128, 130 or 131.

The presence and/or amount of annealed probe(s) can be detected, or the amount of an amplification product produced through annealing of the primers to the nucleic acids can be detected, as an indication of the presence and/or amount of S. aureus, and as an indication of the presence and/or amount of MRSA.

Compositions and Kits

Provided herein are also compositions and kits that comprise, consist essentially of, or consist of oligonucleotides described herein. Preferably, oligonucleotides are between 10 and 45 nucleotides in length. For example, oligonucleotides can be at least 10, 11, 12, 13, 14, 15, 16, 17, 18, 19, 20, 21, 22, 23, 24, 25, 30, 31, 32, 33, 34, 35 or more nucleotides in length. As will be understood by those skilled in the art, the nucleic acids of the embodiments disclosed herein can be single-stranded (coding or antisense), or double-stranded, and may be a DNA (genomic, cDNA, or synthetic) or RNA molecule. Additional coding or non-coding sequences may, but need not, be present within a nucleic acid of the embodiments disclosed herein, and a nucleic acid may, but need not, be linked to other molecules and/or support materials.

Accordingly, some embodiments comprise, consist essentially of, or consist of, at least one oligonucleotide of between about 10 to about 45 nucleotides, and preferably at least 10, 11, 12, 13, 14, 15, 16, 17, 18, 19, 20, 21, 22, 23, 24, 25, 30, 31, 32, 33, 34, 35 nucleotides in length which hybridizes under stringent conditions with any of nucleic acids of the following sequences derived from S. aureus nuc sequences or the complements thereof: SEQ ID NOs: 1, 2, 3, 4, 5, 6, 7, 8, 9, 10, 11 or 12, for example, oligonucleotides that comprise, consist essentially of, or consist of at least one of the following SEQ ID NOs: 1, 2, 3, 4, 5, 6, 7, 8, 9, 10, 11 or 12. Preferred embodiments comprise, consist essentially of, or consist of a primer pair that hybridizes under stringent conditions with any of the pairs of the following SEQ ID NOs: 1 and 5; SEQ ID NOs: 1 and 6; SEQ ID NOs: 2 and 5, SEQ ID NOs: 2 and 6; SEQ ID NOs: 3 and 7; SEQ ID NOs: 3 and 8; SEQ ID NOs: 4 and 7; or SEQ ID NOs: 4 and 8, or the complements thereof, for example primer pairs that comprise, consist essentially of, or consist of the following SEQ ID NOs: 1 and 5; SEQ ID NOs: 1 and 6; SEQ ID NOs: 2 and 5, SEQ ID NOs: 2 and 6; SEQ ID NOs: 3 and 7; SEQ ID NOs: 3 and 8; SEQ ID NOs: 4 and 7; or SEQ ID NOs: 4 and 8. In some embodiments, at least one probe comprising an oligonucleotide that hybridizes under stringent conditions SEQ ID NOs: 9 and 11 (e.g., SEQ ID NOs: 10 and 12), or the complement thereof, is provided.

Other aspects relate to compositions useful for the detection of S. aureus and MRSA in a single reaction. Accordingly, some embodiments comprise, consist essentially of, or consist of, at least one primer and/or probe that is preferably between about 10 to about 45 nucleotides in length, such as an oligonucleotide that is at least 10, 11, 12, 13, 14, 15, 16, 17, 18, 19, 20, 21, 22, 23, 24, 25, 30, 31, 32, 33, 34, 35 in length that hybridizes to an S. aureus-specific nuc sequence, and at least one primer and/or probe that hybridizes to at least one MREJ sequence of MREJ types i-xx. Some embodiments provide at least two primer pairs, wherein a first primer pair hybridizes under stringent conditions to S. aureus-specific nuc sequences (e.g., SEQ ID NOs: 1 and 5; SEQ ID NOs: 1 and 6; SEQ ID NOs: 2 and 5, SEQ ID NOs: 2 and 6; SEQ ID NOs: 3 and 7; SEQ ID NOs: 3 and 8; SEQ ID NOs: 4 and 7; or SEQ ID NOs: 4 and 8) and a second primer pair hybridizes to MREJ sequences (e.g., SEQ ID NOs: 92 and 82; 92 and 83; 92 and 84; 104 and 86; 104 and 87; 104 and 88; 99 and 89; 99 and 199 (for the detection of MREJ type i); SEQ ID NOs: 92 and 82; 92 and 129; 92 and 130; 93 and 83; and 92 and 84; 99 and 89; 99 and 199 (for the detection of MREJ type ii); SEQ ID NOs: 92 and 136; 92 and 137; 92 and 138; 99 and 202; 99 and 144 (for the detection of MREJ type iii); SEQ ID NOs: 92 and 141; 99 and 105; 99 and 150 (for the detection of MREJ type iv); SEQ ID NOs: 92 and 146; 99 and 196; 99 and 155 (for the detection of MREJ type v); SEQ ID NOs: 92 and 152; 99 and 161; (for the detection of MREJ type vi); SEQ ID NOs: 92 and 153; 92 and 154; 99 and 162; 99 and 163 (for the detection of MREJ type vii); SEQ ID NOs: 92 and 162; 92 and 163; 99 and 170 (for the detection of MREJ type viii); SEQ ID NOs: 92 and 168; 99 and 177 (for the detection of MREJ type ix); SEQ ID NOs: 197 and an oligonucleotide that hybridizes under stringent conditions to orf22 (for the detection of MREJ type x); SEQ ID NOs: 189 and 106; 189 and 99; 189 and 190; 189 and 109 (for the detection of MREJ type xi); SEQ ID NOs: 194 and 106; 194 and 99; 104 and 191; 194 and 109 (for the detection of MREJ type xii); SEQ ID NOs: 177 and 106; 177 and 99; 177 and 190; and 177 and 109 (for the detection of MREJ type xiii); SEQ ID NOs: 177 and 106; 177 and 99; 177 and 193; 177 and 109 (for the detection of MREJ type xiv); SEQ ID NOs: 184 and 106; 108 and 99; 184 and 191; 184 and 191 (for the detection of MREJ type xv); SEQ ID NOs: 89 and 109 (for the detection of MREJ type xvi); SEQ ID NOs: 185 and 106; 185 and 99; 185 and 191; 185 and 109 (for the detection of MREJ type xvii); SEQ ID NOs: 186 and 106; 186 and 99; 186 and 193; 186 and 109 (for the detection of MREJ type xviii); SEQ ID NOs: 187 and 106; 107 and 99; 187 and 913; 187 and 109 (for the detection of MREJ type xix); SEQ ID NOs: 188 and 106; 188 and 99; 188 and 913; and 188 and 109 (for the detection of MREJ type xx)). In some embodiments, at least one probe(s) that can hybridize to amplification products produced by an S. aureus-specific nuc primer pair and/or MREJ-specific primer pair described herein is also provided (e.g., SEQ ID NOs: 9, 10, 11, 12, 126, 128, 130 or 131).

Accordingly, some embodiments comprise, consist essentially of, or consist of primer pairs that hybridize under stringent conditions to the nucleic acid sequences of:

SEQ ID NOs: 1 and 6
SEQ ID NOs: 99 and 199;

SEQ ID NOs: 99 and 144;
SEQ ID NOs: 99 and 150;
SEQ ID NOs: 99 and 155; and
SEQ ID NOs: 99 and 163, or the complements thereof.

Other embodiments comprise, consist essentially of, or consist of a plurality of primer pairs, wherein the primers anneal under stringent conditions to the nucleic acid sequences of:
SEQ ID NOs: 3 and 8;
SEQ ID NOs: 99 and 199;
SEQ ID NOs: 99 and 144;
SEQ ID NOs: 99 and 150;
SEQ ID NOs: 99 and 155; and
SEQ ID NOs: 99 and 163, or the complements thereof.

Still other aspects relate to kits for the detection and/or quantification of *S. aureus*, or *S. aureus* and MRSA. In some embodiments, the kits comprise, consist essentially of, or consist of, at least one oligonucleotide of between about 10 to about 45 nucleotides in length, for example at least 10, 11, 12, 13, 14, 15, 16, 17, 18, 19, 20, 21, 22, 23, 24, 25, 30, 31, 32, 33, 34, 35 nucleotides in length, which hybridizes under stringent conditions with any of nucleic acids of the following sequences derived from *S. aureus* nuc sequences or the complements thereof: SEQ ID NOs: 1, 2, 3, 4, 5, 6, 7, 8, 9, 10, 11 or 12. Preferred embodiments provide kits that comprise, consist essentially of, or consist of a primer pair that hybridizes under stringent conditions with any of the pairs of the following SEQ ID NOs: 1 and 5; SEQ ID NOs: 1 and 6; SEQ ID NOs: 2 and 5, SEQ ID NOs: 2 and 6; SEQ ID NOs: 3 and 7; SEQ ID NOs: 3 and 8; SEQ ID NOs: 4 and 7; or SEQ ID NOs: 4 and 8, or the complements thereof. In some embodiments, the kit provides at least one probe comprising an oligonucleotide that hybridizes under stringent conditions SEQ ID NOs: 9 and 11 (e.g., SEQ ID NOs: 10 and 12), or the complement thereof.

Other embodiments provide kits useful for the detection of *S. aureus* and MRSA together. In some embodiments, the kits comprise, consist essentially of, or consist of, at least one primer and/or probe that is between about 10 to about 45 nucleotides in length, for example, at least 10, 11, 12, 13, 14, 15, 16, 17, 18, 19, 20, 21, 22, 23, 24, 25, 30, 31, 32, 33, 34, 35 nucleotides in length, that hybridizes to an *S. aureus*-specific nuc sequence, and at least one primer and/or probe that hybridizes to at least one MREJ sequence of MREJ types i-xx. Some embodiments provide kits, wherein the kits include at least two primer pairs. A first primer pair can hybridize under stringent conditions to *S. aureus*-specific nuc sequences (e.g., primers that are at least 10 nucleotides in length and can hybridize under stringent conditions to SEQ ID NOs: 1 and 5; SEQ ID NOs: 1 and 6; SEQ ID NOs: 2 and 5, SEQ ID NOs: 2 and 6; SEQ ID NOs: 3 and 7; SEQ ID NOs: 3 and 8; SEQ ID NOs: 4 and 7; or SEQ ID NOs: 4 and 8, or the complement thereof) and a second primer pair can hybridize under stringent conditions to MREJ sequences (e.g., primers that are at least 10 nucleotides in length and can hybridize under stringent conditions to SEQ ID NOs: 92 and 82; 92 and 83; 92 and 84; 104 and 86; 104 and 87; 104 and 88; 99 and 89; 99 and 199 (for the detection of MREJ type i); SEQ ID NOs: 92 and 82; 92 and 129; 92 and 130; 93 and 83; and 92 and 84; 99 and 89; 99 and 199 (for the detection of MREJ type ii); SEQ ID NOs: 92 and 136; 92 and 137; 92 and 138; 99 and 202; 99 and 144 (for the detection of MREJ type iii); SEQ ID NOs: 92 and 141; 99 and 105; 99 and 150 (for the detection of MREJ type iv); SEQ ID NOs: 92 and 146; 99 and 196; 99 and 155 (for the detection of MREJ type v); SEQ ID NOs: 92 and 152; 99 and 161; (for the detection of MREJ type vi); SEQ ID NOs: 92 and 153; 92 and 154; 99 and 162; 99 and 163 (for the detection of MREJ type vii); SEQ ID NOs: 92 and 162; 92 and 163; 99 and 170 (for the detection of MREJ type viii); SEQ ID NOs: 92 and 168; 99 and 177 (for the detection of MREJ type ix); SEQ ID NOs: 197 and an oligonucleotide that hybridizes under stringent conditions to orf22 (for the detection of MREJ type x); SEQ ID NOs: 189 and 106; 189 and 99; 189 and 190; 189 and 109 (for the detection of MREJ type xi); SEQ ID NOs: 194 and 106; 194 and 99; 104 and 191; 194 and 109 (for the detection of MREJ type xii); SEQ ID NOs: 177 and 106; 177 and 99; 177 and 190; and 177 and 109 (for the detection of MREJ type xiii); SEQ ID NOs: 177 and 106; 177 and 99; 177 and 193; 177 and 109 (for the detection of MREJ type xiv); SEQ ID NOs: 184 and 106; 108 and 99; 184 and 191; 184 and 191 (for the detection of MREJ type xv); SEQ ID NOs: 89 and 109 (for the detection of MREJ type xvi); SEQ ID NOs: 185 and 106; 185 and 99; 185 and 191; 185 and 109 (for the detection of MREJ type xvii); SEQ ID NOs: 186 and 106; 186 and 99; 186 and 193; 186 and 109 (for the detection of MREJ type xviii); SEQ ID NOs: 187 and 106; 107 and 99; 187 and 913; 187 and 109 (for the detection of MREJ type xix); SEQ ID NOs: 188 and 106; 188 and 99; 188 and 913; and 188 and 109 (for the detection of MREJ type xx) or the complements thereof). In some embodiments, the kits include at least one probe(s) that can hybridize under stringent conditions to amplification products produced by an *S. aureus*-specific nuc primer pair and/or MREJ-specific primer pair described herein is also provided (e.g., a probe comprising an oligonucleotide that can hybridize under stringent conditions to SEQ ID NOs: 9, 10, 11, 12, 126, 128, 130 or 131 or the complement thereof).

Accordingly, some embodiments provide kits that comprise, consist essentially of, or consist of primer pairs that hybridize under stringent conditions to the nucleic acid sequences of:
SEQ ID NOs: 1 and 6
SEQ ID NOs: 99 and 199;
SEQ ID NOs: 99 and 144;
SEQ ID NOs: 99 and 150;
SEQ ID NOs: 99 and 155; and
SEQ ID NOs: 99 and 163, or the complements thereof.

Other embodiments provide kits that comprise, consist essentially of, or consist of a plurality of primer pairs, wherein the primers anneal under stringent conditions to the nucleic acid sequences of:
SEQ ID NOs: 3 and 8;
SEQ ID NOs: 99 and 199;
SEQ ID NOs: 99 and 144;
SEQ ID NOs: 99 and 150;
SEQ ID NOs: 99 and 155; and
SEQ ID NOs: 99 and 163, or the complements thereof.

The diagnostic kits, primers and probes disclosed herein can be used to detect and/or identify *S. aureus*, as well as detect and/or identify both *S. aureus* and MRSA of MREJ types i to xx, in both in vitro and/or in situ applications. For example, it is contemplated that the kits may be used in combination with any previously described primers/probes for detecting MRSA of MREJ types i to xx. It is also contemplated that the diagnostic kits, primers and probes disclosed herein can be used alone or in combination with any other assay suitable to detect and/or identify microorganisms, including but not limited to: any assay based on nucleic acids detection, any immunoassay, any enzymatic assay, any biochemical assay, any lysotypic assay, any serological assay, any differential culture medium, any enrichment culture medium, any selective culture medium, any specific assay medium, any identification culture medium, any enumeration culture medium, any cellular stain, any culture on specific cell lines, and any infectivity assay on animals.

Having generally described this invention, a further understanding can be obtained by reference to certain specific examples which are provided herein for purposes of illustration only, and are not intended to be limiting.

EXAMPLE 1

This example illustrates the utility of various primer pairs, chosen for optimized, specific detection of S. aureus from a sample using PCR. SEQ ID NOs: 1, 2, 3, 4, 5, 6, 7, 8 were designed to anneal to S. aureus-specific regions of the nuc gene. PCR reaction mixtures included 0.5 µM of each of the indicated primers, 0.2 mM dNTPs (Roche), 2 mM $MgCl_2$ (SIGMA), 1 unit FASTSTART™ Taq DNA polymerase (Roche), 50 mM Tris (EMD), 10 mM KCl (Laboratoire Mat), and 5 mM $(NH_4)_2SO_4$ (SIGMA).

For each primer pair tested, three replicates containing varying amounts of chromosomal template DNA were run. One set of reactions included 15 copies of chromosomal template DNA from S. aureus strain ATCC 43300 (MRSA). Another set of reactions included 185 copies of ATCC 43300 template DNA. A negative control was also run, which did not have any added template DNA. Parallel sets of reactions were run with chromosomal template DNA from S. aureus strain ATCC 25923 (MSSA).

PCR reactions were performed using a SMARTCYCLER® QT-PCR machine (Cepheid). The cycling parameters were as follows: 95° C. for 900 min, followed by 45 cycles of 95° C. for 5 sec, 59° C. for 15 sec and 72° C. for 20 sec. Amplified products were visualized on agarose gels (FIGS. 1A and 1B).

Figure 1B:
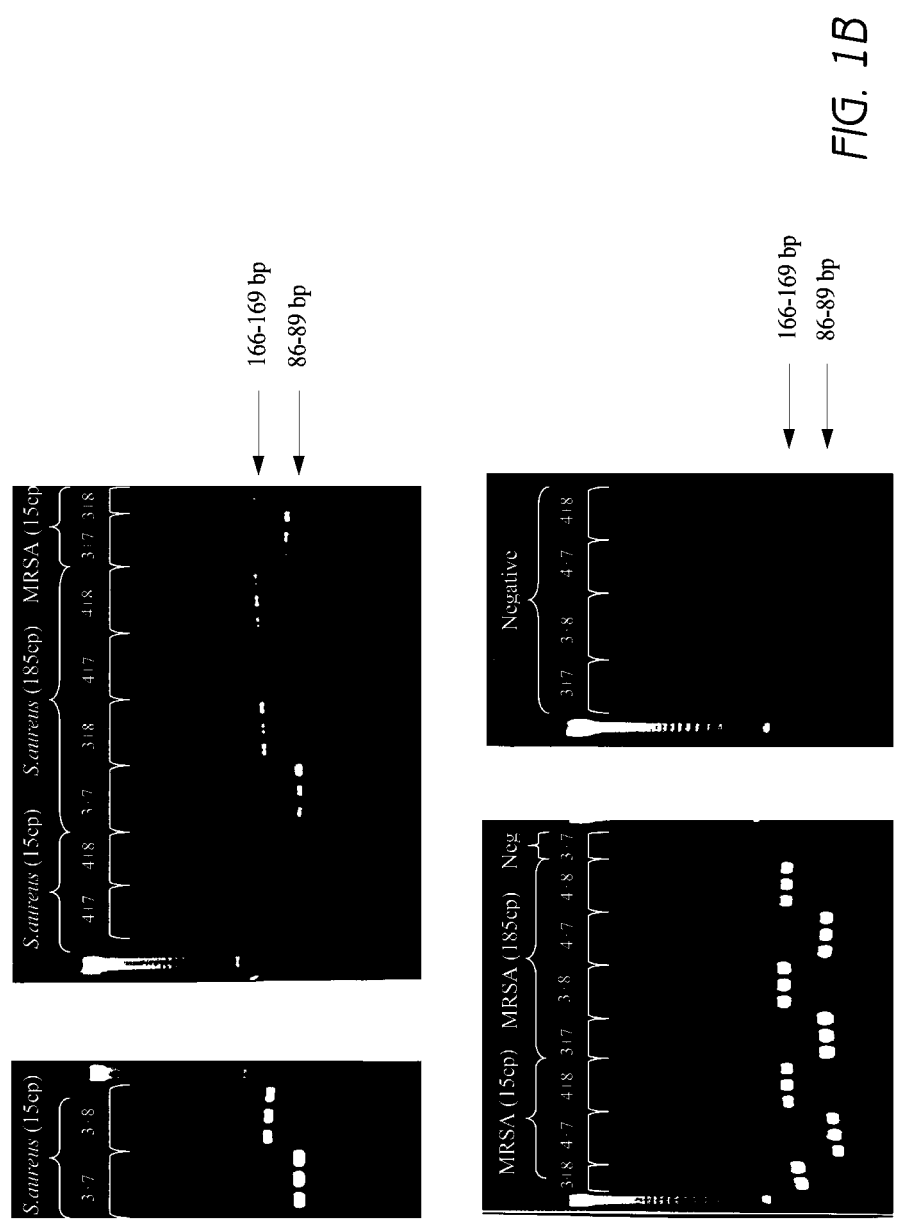

As shown in FIGS. 1A and 1B, the following primer pairs showed particularly good results in the specific amplification of DNA from both MSSA and MRSA S. aureus strains:
SEQ ID NOs: 1 and 5
SEQ ID NOs: 1 and 6
SEQ ID NOs: 2 and 6
SEQ ID NOs: 4 and 7
SEQ ID NOs: 4 and 8
SEQ ID NOs: 3 and 7, and
SEQ ID NOs: 3 and 8.

The primer pair SEQ ID NOs: 2 and 5 was less sensitive, as indicated by the relative amount of amplification product produced, compared to other primer pairs.

EXAMPLE 2

The ability to detect S. aureus and to identify MRSA in a single reaction was tested. A multiplex PCR reaction was designed to include primers that anneal under standard PCR conditions to the S. aureus species-specific orfX sequence and a sequence of SCCmec right extremity junction (MREJ) of the most commonly clinically encountered MRSA types (i.e., MRSA of MREJ types i, ii, iii, iv, v, vii). SEQ ID NOs: 99, 199, 144, 150, 155 and 163 were used for the detection of MRSA of MREJ types i, ii, iii, iv, v, and vii. Primers that anneal to S. aureus specific regions of the nuc gene under the same conditions (SEQ ID NOs: 3 and 8) were used in the reaction for the detection of both MRSA and MSSA strains in the test reactions. Molecular beacon probes which are detectable on the SMARTCYCLER® apparatus at FAM, Texas Red and TET channels were designed for hybridization to amplification products of the MRSA specific reactions (SEQ ID NOs: 126 and 130), nuc/S. aureus specific reactions (SEQ ID NO: 12), and an internal control, respectively.

PCR reactions included 0.9 µM SEQ ID NO: 99, 0.4 µM SEQ ID NO: 199; 0.6 µM SEQ ID NO: 144, 0.3 µM SEQ ID NO: 150, 0.2 µM SEQ ID NO: 155, 0.7 µM SEQ ID NO: 163, 0.1 µM SEQ ID NO: 3, 0.1 µM SEQ ID NO: 8, 0.1 µM SEQ ID NO: 126, 0.1 µM SEQ ID NO: 130, 0.25 µM SEQ ID NO: 12, 0.2 µM control DNA, 0.3 mM dNTPs (Roche) 4 mM $MgCl_2$ (SIGMA), 2.8 units FASTSTART® Taq DNA polymerase (Roche), 100 mM Tris, pH 8.3 (EMD), 10 mM KCl (Laboratoire Mat), 5 mM $(NH_4)_2SO_4$ (SIGMA), 0.15 mg/mL BSA (SIGMA), 4% Trehalose (SIGMA), 3000 copies of internal control template DNA, 2780 copies of S. epidermidis chromosomal DNA, and either 0, 2.5, 5, 10, 15 or 20 copies MSSA chromosomal DNA (isolated from ATCC strain 25923) or 0, 2.5, 5, 10 or 20 copies of MRSA chromosomal DNA (isolated from ATCC strain 43300).

PRC reactions were performed in a SMARTCYCLER® instrument (Cepheid). Cycling parameters were as follows: 95° C. for 900 min, followed by 45 cycles of 95° C. for 5 sec, 59° C. for 15 sec and 72° C. for 20 sec. The fluorescence was continuously measured at the appropriate wavelengths, and is graphically depicted in FIGS. 2A and 2B.

Figure 2A:
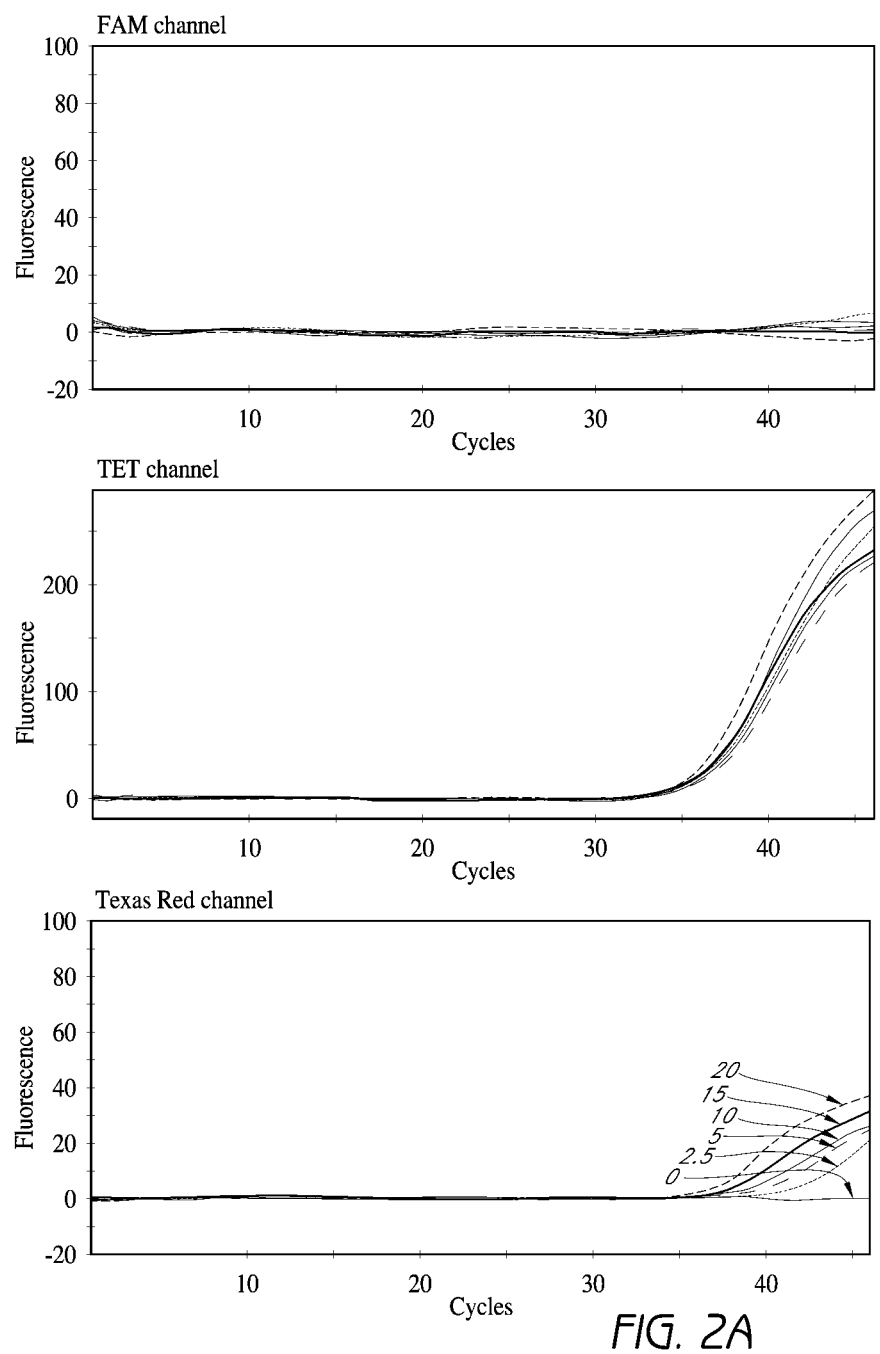
FIGS. 2A and 2B show a graphical depiction of PCR amplification curves measured from reactions containing molecular beacon probes. Reactions contained 0, 2.5, 5, 10, 15, or 20 copies of MSSA (FIG. 2A) or MRSA (FIG. 2B) template DNA, as well as 3000 copies of internal control DNA. Molecular beacon probes were added to each reaction and the fluorescence of the reactions was measured. FAM labeled probes hybridize to MRSA-specific sequences, TET-labeled probes hybridize to internal control DNA sequences, and Texas-Red-labeled probes hybridize to S. aureus-specific nuc sequences.

FIG. 2A depicts the fluorescence readings of reactions containing MSSA template DNA. Under these reaction conditions, 2.5 copies of MSSA DNA were easily detected (Texas Red Channel), demonstrating the utility of SEQ ID NOs: 3, 8 and 12 in multiplex PCR. As expected, positive signals are also present in the TET channel indicating that the internal control worked properly, and that no inhibitors were present in the reactions.

Figure 2B:
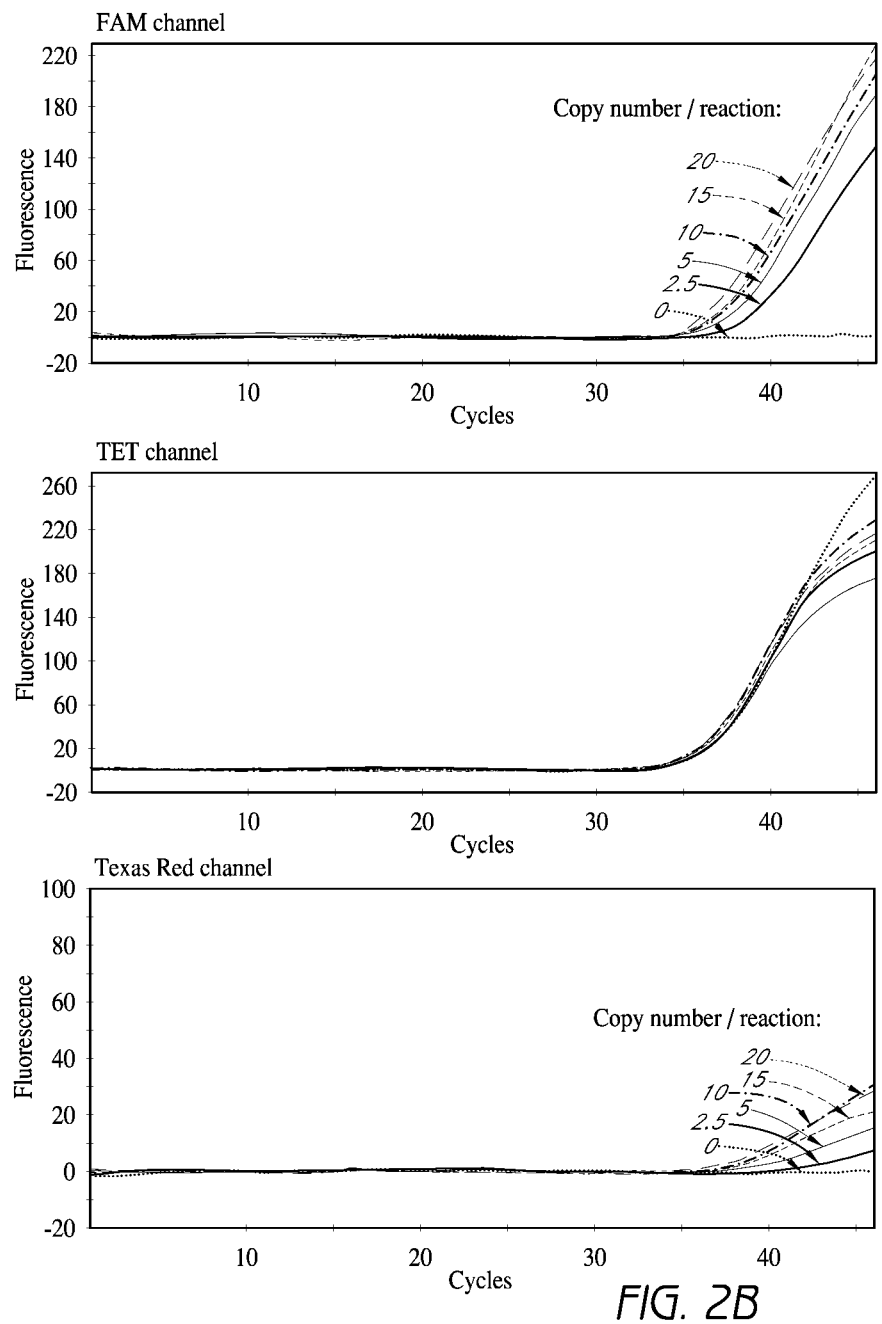

FIG. 2B depicts the fluorescence readings of reactions containing MRSA template DNA. Under these reaction conditions, 2.5 copies of MRSA DNA were easily detected (FAM channel). This demonstrates the utility of SEQ ID NOs: 99, 199, 150, 155, 144, 126, and 130 in a multiplex PCR that can detect all S. aureus strains, including MRSA. As shown in the Texas-Red channel, the nuc-specific primers and probes (SEQ ID NOs: 3, 8, and 12) detected 2.5 copies of DNA. Positive signals are also present in the TET channel, indicating that the internal control worked properly, and that no inhibitors were present in the reactions.

This example highlights the very high sensitivity obtainable with a PCR multiplex assay that amplifies MREJ sequences from MRSA and nuc sequences from S. aureus with an internal control.

EXAMPLE 3

The specificity of a multiplex PCR assay that amplifies MREJ sequences from MRSA and the nuc sequence from S. aureus was analyzed. Chromosomal DNA from 80 bacterial species other than S. aureus was used as template DNA in a multiplex PCR assay as described in Example 2. The strains tested are enumerated in Table 2.

1 ng of chromosomal DNA isolated from each species indicated in Table 1 was used in a separate reaction containing 0.9 µM SEQ ID NO: 99, 0.4 µM SEQ ID NO: 199; 0.6 µM SEQ ID NO: 144, 0.3 µM SEQ ID NO: 150, 0.2 µM SEQ ID NO: 155, 0.7 µM SEQ ID NO: 163, 0.1 µM SEQ ID NO: 3, 0.1 µM SEQ ID NO: 8, 0.1 µM SEQ ID NO: 126, 0.1 µM SEQ ID NO: 131, 0.25 µM SEQ ID NO: 11, 0.2 µM internal control DNA, 0.3 mM dNTPs (Roche) 4 mM $MgCl_2$ (SIGMA), 2.8 units FASTSTART® Taq DNA polymerase (Roche), 100 mM Tris, pH 8.3 (EMD), 10 mM KCl (Laboratoire Mat), 5 mM $(NH_4)_2SO_4$ (SIGMA), 0.15 mg/mL BSA (SIGMA), 4% Trehalose (SIGMA), 3000 copies of internal control template DNA, and 2780 copies of S. epidermidis DNA.

Each reaction was performed in triplicate. The reactions were allowed to proceed following the parameters set forth in Example 2. Table 2 summarizes the results of the reactions. No positive signal was observed in the FAM and Texas Red channels for the 80 different species tested. A positive signal was detected in the TET channel for each of the 80 different species tested, indicating that the reactions did not contain inhibitors. The algorithm of interpretation of results is summarized in Table 3.

TABLE 2

| Species | Strain number | PCR results | | |
|---|---|---|---|---|
| | | MRSA (FAM) | IC (TET) | S. aureus (Texas Red) |
| Acinetobacter baumannii | ATCC 19606 | − | + | − |
| Acinetobacter lwoffi | CDCF 3697 | − | + | − |
| Actinomyces israelii | ATCC 12102 | − | + | − |
| Actinomyces pyogenes | ATCC 19411 | − | + | − |
| Bacillus cereus | ATCC 14579 | − | + | − |
| Bacteroides fragilis | ATCC 25285 | − | + | − |
| Bifidobacterium breve | ATCC 15700 | − | + | − |
| Bordetella pertusis | ATCC 9797 | − | + | − |
| Corynebacterium genitalium | LSPQ3583 | − | + | − |
| Corynebacterium aquaticus | ATCC 14665 | − | + | − |
| Corynebacterium bovis | ATCC 7715 | − | + | − |
| Corynebacterium flavescens | ATCC 10340 | − | + | − |
| Enterobacter cloacae | ATCC 13047 | − | + | − |
| Enterococcus faecalis | ATCC 19433 | − | + | − |
| Enterococcus faecium | ATCC 19434 | − | + | − |
| Enterococcus flavescens | ATCC 49996 | − | + | − |
| Enterrococcus gallinarum | ATCC 49573 | − | + | − |
| Enterrococcus hirae | ATCC 8043 | − | + | − |
| Escherichia coli | ATCC 23511 | − | + | − |
| Helicobacter pylori | IDI-2019 | − | + | − |
| Fusobacterium nucleatum subsp. Polymorphum | ATCC 10953 | − | + | − |
| Gardnerella vaginalis | ATCC 14019 | − | + | − |
| Haemophilus influenzae | ATCC 9006 | − | + | − |
| Homo sapiens | 2.16 | − | + | − |
| Klebsiella pneumoniae | ATCC 13883 | − | + | − |
| Lactobacillus crispatus | ATCC 33820 | − | + | − |
| Listeria monocytogenes | L 374 | − | + | − |
| Micrococcus luteus | ATCC 9341 | − | + | − |
| Moraxella catarrhalis | ATCC 43628 | − | + | − |
| Neisseria gonorrhoeae | ATCC 35201 | − | + | − |
| Neisseria meningitides | ATCC 13077 | − | + | − |
| Pasteurella aerogenes | ATCC 27883 | − | + | − |
| Peptostreptococcus anaerobius | ATCC 27337 | − | + | − |
| Peptostreptococcus asaccharolyticus | LSPQ 2639 | − | + | − |
| Porphyromonas asaccharolytica | ATCC 25260 | − | + | − |
| Prevotella melaninogenica | ATCC 25845 | − | + | − |
| Propionibacterium acnes | ATCC 6919 | − | + | − |
| Proteus mirabilis | ATCC 29906 | − | + | − |
| Pseudomonas aeruginosa | ATCC 35554 | − | + | − |
| Pseudomonas fluorescens | ATCC 13525 | − | + | − |
| Salmonella typhimurium | ATCC 14028 | − | + | − |
| Serratia marcescens | ATCC 13880 | − | + | − |
| Shigella sonnei | ATCC 29930 | − | + | − |
| Staphylococcus arlettae | CCRI-9265 | − | + | − |
| Staphylococcus auricularis | R413 | − | + | − |
| Staphylococcus capitis | CCRI-9572 | − | + | − |
| Staphylococcus caprae | CCRI-9117 | − | + | − |
| Staphylococcus carnosus | R714 | − | + | − |
| Staphylococcus chromogenes | ATCC 43764 | − | + | − |
| Staphylococcus cohnii subsp. Urealyticum | R570 | − | + | − |
| Staphylococcus delphini | ATCC 49171 | − | + | − |
| Staphylococcus epidermidis | ATCC 35984 | − | + | − |
| Staphylococcus equorum | ATCC 43958 | − | + | − |
| Staphylococcus fells | ATCC 49168 | − | + | − |

TABLE 2-continued

| Species | Strain number | PCR results | | |
|---|---|---|---|---|
| | | MRSA (FAM) | IC (TET) | S. aureus (Texas Red) |
| Staphylococcus gallinarum | ATCC 35539 | − | + | − |
| Staphylococcus haemolyticus | ATCC 29970 | − | + | − |
| Staphylococcus hominis | CCRI-1347 | − | + | − |
| Staphylococcus intermedius | ATCC 29663 | − | + | − |
| Staphylococcus kloosii | ATCC 43959 | − | + | − |
| Staphylococcus lentus | ATCC 29070 | − | + | − |
| Staphylococcus lugdunensis | ATCC 43809 | − | + | − |
| Staphylococcus pasteuri | ATCC 51129 | − | + | − |
| Staphylococcus pulvereri | ATCC 51698 | − | + | − |
| Staphylococcus saprophyticus | ATCC 15305 | − | + | − |
| Staphylococcus sciuri | R573 | − | + | − |
| Staphylococcus simulans | ATCC 27848 | − | + | − |
| Staphylococcus warneri | ATCC 35985 | − | + | − |
| Staphylococcus xylosus | LSPQ2517 | − | + | − |
| Streptococcus agalactiae | ATCC 12973 | − | + | − |
| Streptococcus anginosus | ATCC 33397 | − | + | − |
| Streptococcus mitis | ATCC 49456 | − | + | − |
| Streptococcus mutans | ATCC 25175 | − | + | − |
| Streptococcus pneumoniae | ATCC 49619 | − | + | − |
| Streptococcus pyogenes | ATCC 12384 | − | + | − |
| Streptococcus salivarius | ATCC 7073 | − | + | − |
| Streptococcus sanguinis | ATCC 10556 | − | + | − |
| Streptococcus suis | ATCC 43765 | − | + | − |
| Yersinia enterocolitica | ATCC 23715 | − | + | − |
| Candida albicans | ATCC 10231 | − | + | − |
| Candida glabrata | ATCC 66032 | − | + | − |

TABLE 3

| FAM Assay Result Reported | Texas-Red Assay Result Reported | IC (TET) Result Reported | Interpretation of Result |
|---|---|---|---|
| Negative | Negative | PASS | No S. aureus DNA detected |
| Positive | Positive or Negative | N/A | MRSA DNA detected |
| Negative | Positive | N/A | S. aureus DNA detected, no MRSA DNA detected |
| Unresolved | | Fail | Unresolved-inhibitory specimen or reagent failure |

This example highlights the complete specificity reached with a PCR multiplex assay that amplifies MREJ sequences from MRSA and nuc sequence from S. aureus with an internal control.

EXAMPLE 4

The ability of a multiplex PCR assay that amplifies MREJ sequences from MRSA and nuc sequence from S. aureus to accurately detect S. aureus and identify MRSA directly from wound specimens was tested.

A multiplex PCR reaction was designed to include primers to amplify sequences specific to the MREJ regions of the most clinically relevant MRSA (e.g., primers that anneal to S. aureus species-specific orfX sequences and SCCmec sequences), as well as primers that anneal to S. aureus specific regions of the nuc gene of all S. aureus strains (e.g., MRSA and MSSA), under the same conditions. Briefly, SEQ ID NOs: 99, 199, 144, 150, 155 and 163 were used for amplification of sequences of the MREJ region of various MRSA of MREJ types i, ii, iii, iv, v, and vii. Primers that anneal to S. aureus specific regions of the nuc gene under the same conditions (SEQ ID NOs: 3 and 8) were used in the reaction for the detection of both MRSA and MSSA strains in the test reactions. Molecular beacon probes which are detectable on the SMARTCYCLER® apparatus at FAM, Texas Red and Tet channels were designed for hybridization to amplification products of the MRSA specific reactions (SEQ ID NOs: 126 and 130), nuc/S. aureus specific reactions (SEQ ID NO: 12), and the internal control, respectively.

One hundred and three wound samples were collected on patients using Amies liquid swabs (Copan Diagnostics, Inc). Samples were cultured and subcultured on blood agar plates (Becton Dickinson). Based on their morphology, suspected S. aureus were identified with a coagulase test (Jorgenson, J. H., and W. E. Kloos. 1987. Staphylococcal Infections, in B. B. Wentworth (ed.), Diagnostic procedures for bacterial infections, 7th ed., American Public Health Association, Washington, D.C.) and in some cases with latex agglutination (Staphaurex, Remel Inc.) Methicillin resistance was determined using the VITEK™ bacterial identification system (bioMérieux, Durham, N.C.).

DNA was isolated from the isolates using the IDI™ lysis kit (GeneOhm Sciences, Inc.). A swab of the isolate was broken in 1 mL of TE buffer (10 mM Tris, 1 mM EDTA, pH 8.0) and vortexed for 1 min at high speed. 50 µL of the cell suspensions were transferred to a lysis tube containing glass beads and vortexed for 5 minutes at high speed. The tubes were centrifuged at 13,000 rpms for 2 min and heated at 95° C. for 2 minutes. The tube was placed on ice until used in the reaction.

3 µL of the lysis reaction was added to a PCR mix that contained 0.9 µM SEQ ID NO: 99, 0.4 µM SEQ ID NO: 199, 0.6 µM SEQ ID NO: 144, 0.3 µM SEQ ID NO: 150, 0.2 µM SEQ ID NO: 155, 0.7 µM SEQ ID NO: 163, 0.1 µM SEQ ID NO: 3, 0.1 µM SEQ ID NO: 8, 0.1 µM SEQ ID NO: 126, 0.1 µM SEQ ID NO: 130, 0.25 µM SEQ ID NO:12, 0.2 µM internal control DNA, 0.3 µM dNTPs (Roche), 4 mM MgCl$_2$ (SIGMA), 2.8 units FASTSTART® Taq polymerase (Roche), 100 mM Tris, pH 8.3 (EMD), 10 mM KCl (LaboratoireMat), 5 mM (NH$_4$)$_2$SO$_4$ (SIGMA), 0.15 mg/mL BSA (SIGMA) 4% trehalose (SIGMA), 3000 copies internal control DNA, and 2780 copies S. epidermidis chromosomal DNA.

PCR was carried out in a SMARTCYCLER® (Cepheid) using the same cycling parameters as described in Example 2. For each specimen, the cycle threshold (CT) in FAM, Texas-Red, and TET channels was determined using the SMARTCYCLER® software. Assay results were interpreted as indicated in Table 3:

The multiplex PCR assay above is designed such that any S. aureus strain produces a positive signal in the Texas-Red channel. The presence of a clinically relevant MRSA will produce a positive signal in the FAM channel. Accordingly, a negative result in the FAM channel combined with a positive result in the Texas-Red channel is indicative of the presence of MSSA.

In instances where a discordant result appeared between culture assays described above, and the multiplex PCR reaction, Tryptic Soy Broth was added to the TE buffer tube containing the swab, and incubated overnight, at 35° C. 50 µL of the overnight culture was plated on blood agar plates and isolates were identified as MRSA, MSSA, or negative (no S. aureus).

The data collected are depicted in Tables 4A, 4B and 4C, below.

TABLE 4A

| | | (A) | | | | |
|---|---|---|---|---|---|---|
| | | PCR | | | | |
| | | MRSA | MSSA | Negative | Total | Unresolved |
| Culture | MRSA | 27 (32)* | 0 (0) | 0 (0) | 27 (32) | 1 (0) |
| | MSSA | 2 (2) | 18 (19) | 1 (0) | 21 (21) | 1 (0) |
| | Negative | 4 (0) | 1 (1) | 43 (45) | 48 (46) | 5 (4) |
| | Total | 33 (34) | 19 (20) | 44 (45) | 96 (99) | 7 (4) |

*before resolution of discordant results (after resolution of discordant results)

TABLE 4B

| | before resolution | after resolution |
|---|---|---|
| MRSA sensitivity | 100% (27/27) | 100% (32/32) |
| MSSA sensitivity | 85.7% (18/21) | 90.5% (19/21) |
| S. aureus sensitivity | 97.9% (47/48) | 100% (53/53) |
| Specificity | 89.6% (43/48) | 97.8% (45/46) |
| Unresolved | 6.8% (7/103) | 3.9% (4/103) |

TABLE 4C

| Specimen number | Culture result | Status | PCR result | | |
|---|---|---|---|---|---|
| | | | MRSA (FAM CT) | IC (TET CT) | S. aureus (Texas Red CT) |
| 1 | MSSA | MSSA | 0.0 | 0.0 | 23.5 |
| 2 | NEGATIVE | Unresolved | 0.0 | 37.5 | 0.0 |
| 3 | MSSA | MSSA | 0.0 | 0.0 | 30.5 |
| 4 | NEGATIVE | NEGATIVE | 0.0 | 37.8 | 0.0 |
| 5 | NEGATIVE | NEGATIVE | 0.0 | 37.3 | 0.0 |
| 6 | MRSA | MRSA | 25.0 | 0.0 | 24.5 |
| 7 | MRSA | MRSA | 36.0 | 0.0 | 0.0 |
| 8 | MSSA | MRSA | 30.7 | 0.0 | 33.0 |

TABLE 4C-continued

| | | | | | |
|---|---|---|---|---|---|
| 9 | MSSA | MSSA | 0.0 | 0.0 | 23.8 |
| 10 | NEGATIVE | NEGATIVE | 0.0 | 37.3 | 0.0 |
| 11 | MRSA | MRSA | 27.8 | 0.0 | 27.5 |
| 12 | NEGATIVE | NEGATIVE | 0.0 | 37.1 | 0.0 |
| 13 | NEGATIVE | NEGATIVE | 0.0 | 37.1 | 0.0 |
| 14 | MRSA | MRSA | 25.6 | 0.0 | 25.0 |
| 15 | MSSA | MSSA | 0.0 | 37.1 | 35.7 |
| 16 | NEGATIVE | NEGATIVE | 0.0 | 37.1 | 0.0 |
| 17 | MRSA | MRSA | 23.9 | 0.0 | 23.5 |
| 18 | MRSA | MRSA | 25.2 | 0.0 | 24.5 |
| 19 | MSSA | MSSA | 0.0 | 0.0 | 21.5 |
| 20 | NEGATIVE | NEGATIVE | 0.0 | 37.0 | 0.0 |
| 21 | MSSA | MSSA | 0.0 | 0.0 | 21.3 |
| 22 | NEGATIVE | NEGATIVE | 0.0 | 36.6 | 0.0 |
| 23 | MRSA | MRSA | 26.9 | 0.0 | 26.7 |
| 24 | MRSA | MRSA | 23.2 | 0.0 | 21.5 |
| 25 | MSSA | MRSA | 37.1 | 38.0 | 38.5 |
| 26 | NEGATIVE | NEGATIVE | 0.0 | 38.7 | 0.0 |
| 27 | NEGATIVE | NEGATIVE | 0.0 | 37.2 | 0.0 |
| 28 | NEGATIVE | NEGATIVE | 0.0 | 36.9 | 0.0 |
| 29 | MRSA | MRSA | 27.1 | 0.0 | 26.5 |
| 30 | NEGATIVE | NEGATIVE | 0.0 | 38.5 | 0.0 |
| 31 | NEGATIVE | NEGATIVE | 0.0 | 37.3 | 0.0 |
| 32 | NEGATIVE | NEGATIVE | 0.0 | 37.0 | 0.0 |
| 33 | NEGATIVE | NEGATIVE | 0.0 | 37.1 | 0.0 |
| 34 | NEGATIVE | Unresolved | 0.0 | 36.8 | 0.0 |
| 35 | NEGATIVE | NEGATIVE | 0.0 | 36.0 | 0.0 |
| 36 | MRSA | MRSA | 25.9 | 0.0 | 25.8 |
| 37 | NEGATIVE | NEGATIVE | 0.0 | 36.9 | 0.0 |
| 38 | NEGATIVE | NEGATIVE | 0.0 | 37.2 | 0.0 |
| 39 | MSSA | MSSA | 0.0 | 0.0 | 28.5 |
| 40 | NEGATIVE | NEGATIVE | 0.0 | 37.4 | 0.0 |
| 41 | NEGATIVE | NEGATIVE | 0.0 | 39.2 | 0.0 |
| 42 | NEGATIVE | MSSA | 0.0 | 0.0 | 34.7 |
| 43 | NEGATIVE | NEGATIVE | 0.0 | 36.9 | 0.0 |
| 44 | NEGATIVE | NEGATIVE | 0.0 | 37.3 | 0.0 |
| 45 | NEGATIVE | NEGATIVE | 0.0 | 38.5 | 0.0 |
| 46 | NEGATIVE | NEGATIVE | 0.0 | 37.5 | 0.0 |
| 47 | NEGATIVE | NEGATIVE | 0.0 | 36.7 | 0.0 |
| 48 | MSSA | MSSA | 0.0 | 36.0 | 34.9 |
| 49 | MSSA | MSSA | 0.0 | 0.0 | 29.0 |
| 50 | NEGATIVE | NEGATIVE | 0.0 | 37.7 | 0.0 |
| 51 | NEGATIVE | NEGATIVE | 0.0 | 36.8 | 0.0 |
| 52 | MRSA | MRSA | 27.6 | 0.0 | 23.8 |
| 53 | MSSA | MSSA | 0.0 | 0.0 | 25.7 |
| 54 | MSSA | MSSA | 0.0 | 34.8 | 32.8 |
| 55 | MRSA | MRSA | 24.5 | 0.0 | 24.9 |
| 56 | NEGATIVE | NEGATIVE | 0.0 | 36.5 | 0.0 |
| 57 | NEGATIVE | NEGATIVE | 0.0 | 36.7 | 0.0 |
| 58 | MRSA | MRSA | 24.3 | 0.0 | 24.0 |
| 59 | MRSA | MRSA | 22.5 | 0.0 | 21.5 |
| 60 | MRSA | MRSA | 28.9 | 0.0 | 28.7 |
| 61 | NEGATIVE | Unresolved | 0.0 | 0.0 | 0.0 |
| 62 | NEGATIVE | NEGATIVE | 0.0 | 36.7 | 0.0 |
| 63 | MRSA | MRSA | 23.9 | 0.0 | 23.5 |

TABLE 4C-continued

| | | | | | |
|---|---|---|---|---|---|
| 64 | MSSA | MSSA | 0.0 | 0.0 | 23.8 |
| 65 | MRSA | MRSA | 29.4 | 0.0 | 29.5 |
| 66 | MRSA | MRSA | 33.7 | 0.0 | 33.8 |
| 67 | NEGATIVE | NEGATIVE | 0.0 | 36.5 | 0.0 |
| 68 | NEGATIVE | NEGATIVE | 0.0 | 36.9 | 0.0 |
| 69 | MRSA | MRSA | 23.2 | 0.0 | 22.5 |
| 70 | MRSA | MRSA | 23.6 | 0.0 | 22.5 |
| 71 | MRSA | MRSA | 37.4 | 0.0 | 0.0 |
| 72 | MSSA | MSSA | 0.0 | 0.0 | 22.0 |
| 73 | NEGATIVE | NEGATIVE | 0.0 | 35.7 | 0.0 |
| 74 | MRSA | MRSA | 36.3 | 36.8 | 35.7 |
| 75 | NEGATIVE | NEGATIVE | 0.0 | 36.5 | 0.0 |
| 76 | NEGATIVE | NEGATIVE | 0.0 | 36.7 | 0.0 |
| 77 | MRSA | MRSA | 22.3 | 0.0 | 22.1 |
| 78 | NEGATIVE | NEGATIVE | 0.0 | 37.1 | 0.0 |
| 79 | NEGATIVE | NEGATIVE | 0.0 | 34.9 | 0.0 |
| 80 | NEGATIVE | NEGATIVE | 0.0 | 36.2 | 0.0 |
| 81 | MRSA | MRSA | 21.5 | 0.0 | 22.5 |
| 82 | NEGATIVE | NEGATIVE | 0.0 | 37.7 | 0.0 |
| 83 | MSSA | MSSA | 0.0 | 0.0 | 22.7 |
| 84 | MSSA | MSSA | 0.0 | 0.0 | 22.7 |
| 85 | MRSA | MRSA | 22.9 | 0.0 | 23.0 |
| 86 | NEGATIVE | NEGATIVE | 0.0 | 37.9 | 0.0 |
| 87 | MRSA | MRSA | 32.3 | 0.0 | 33.7 |
| 88 | MSSA | MSSA | 0.0 | 0.0 | 30.0 |
| 89 | MRSA | MRSA | 21.3 | 0.0 | 21.5 |
| 90 | NEGATIVE | NEGATIVE | 0.0 | 37.4 | 0.0 |
| 91 | NEGATIVE | NEGATIVE | 0.0 | 39.2 | 0.0 |
| 92 | MSSA | MSSA | 0.0 | 0.0 | 31.2 |
| 93 | MRSA | MRSA | 31.9 | 0.0 | 32.0 |
| 94 | NEGATIVE | Unresolved | 0.0 | 0.0 | 0.0 |
| 95 | MSSA | MSSA | 0.0 | 0.0 | 25.1 |
| 96 | NEGATIVE | NEGATIVE | 0.0 | 36.8 | 0.0 |
| 97 | MSSA | MSSA | 0.0 | 37.5 | 41.7 |
| 98 | MRSA | MRSA | 32.5 | 0.0 | 32.9 |
| 99 | NEGATIVE | NEGATIVE | 0.0 | 37.2 | 0.0 |
| 100 | MRSA | MRSA | 28.8 | 0.0 | 29.5 |
| 101 | MRSA | MRSA | 23.2 | 0.0 | 0.0 |
| 102 | NEGATIVE | NEGATIVE | 0.0 | 36.6 | 0.0 |
| 103 | MRSA | MRSA | 35.2 | 35.7 | 36.0 |

As shown in Tables 4A and 4B, the multiplex assay is 100% sensitive for MRSA, indicating that every positive MRSA result achieved in the PCR assay corresponded to a positive result in the culture identification, both before and after resolution. The sensitivity of the PCR assay for *S. aureus* detection after resolution was 90.5%, with 19 of 21 of MSSA strains showing a positive result in the PCR assay. Importantly, however, the two strains that were incorrectly identified as not being MSSA are strains that were formerly MSSA but lost a portion of the SCCmec element and retained the junction near orfX to which the PCR amplification primers hybridize.

Table 4C shows the individual PCR and culture results for each of the 103 wound specimens following the resolution of discordant results. The shaded entries indicate that the results obtained in the culture test and in the PCR assay were in agreement. The column labeled (CT) indicates the PCR cycle in which a positive signal becomes detectable over the background noise. As shown in the table, four samples were not able to be resolved in the PCR assay, due to the presence of reaction inhibitors in the sample.

The results above demonstrate the high sensitivity and specificity of the multiplex PCR assay applied directly to wound specimens. Accordingly, the multiplex assay offers the first convenient, reliable, sensitive, and specific assay specific for both MRSA and MSSA.

The methods, compositions, and devices described herein are presently representative of preferred embodiments, they are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Numerous literature and patent references have been cited in the present patent application. Each and every reference that is cited in this patent application is hereby expressly incorporated by reference in its entirety.

What is claimed is:

1. A method of specifically detecting the presence of a *Staphylococcus aureus* (*S. aureus*) strain and identifying a methicillin-resistant *S. aureus* strain from a sample in a single assay, comprising:
   simultaneously contacting said sample with
      at least one primer pair that is capable of amplifying a sequence from a nuc gene *S. aureus* when an *S. aureus* strain is present in the sample to produce a nuc amplicon, said primer pair comprising a first and a second nuc primer, said first and second nuc primers being between 11 and 45 nucleotides in length and being capable of annealing under PCR conditions to opposite strands of *S. aureus* chromosomal DNA within the nuc gene; and
      at least one MREJ primer pair comprising a first and second MREJ primer that is capable of amplifying a polymorphic mec right extremity junction (MREJ) sequence of a methicillin resistant *S. aureus* (MRSA) strain when an MRSA strain is present in the sample to produce an MREJ amplicon, said MREJ sequence comprising polymorphic sequences from the right extremity of an SCCmec cassette inserted into the *S. aureus* chromosome and *S. aureus* chromosomal DNA, said first and second MREJ primers being between 11 and 45 nucleotides in length and being capable of annealing under PCR conditions to opposite strands of MRSA chromosomal DNA, to create an amplification mixture,
   wherein said PCR conditions comprise 4 mM $MgCl_2$, 100 mM Tris (pH 8.3), 10 mM KCl, 5 mM $(NH_4)_2SO_4$, 0.15 mg/mL BSA, 4% trehalose at 59° C. subjecting the amplification mixture to an amplification protocol to enable amplification of both nuc and MREJ sequences, thereby producing an amplified sample; and detecting the presence and/or amount of nuc amplicons and MREJ amplicons in the amplified sample as an indication of the presence and or amount of *S. aureus* and MRSA, respectively, present in the sample.

2. The method of claim 1, wherein said nuc gene comprises SEQ ID NO: 200.

3. The method of claim 1, wherein said assay further comprises
providing an internal control nucleic acid sequence to said sample, wherein said nuc primer pair and/or said MREJ primer pair produce an internal control amplicon under said amplification protocol.

4. The method of claim 1, wherein said MREJ sequence is selected from the group consisting of an MREJ type i, type ii, type iii, type iv, type v, type vi, type vii, type viii, type ix, and type x sequence, or any combination thereof.

5. The method of claim 4, wherein said MREJ sequence is a type i sequence, wherein SEQ ID NO:14 comprises said MREJ type i sequence.

6. The method of claim 4, wherein said MREJ sequence is a type ii sequence, wherein SEQ ID NO: 23 comprises said MREJ type ii sequence.

7. The method of claim 4, wherein said MREJ sequence is a type iii sequence, wherein SEQ ID NO:43 comprises said MREJ type iii sequence.

8. The method of claim 4, wherein said MREJ sequence is a type iv sequence, wherein SEQ ID NO: 59 comprises said MREJ type iv sequence.

9. The method of claim 4, wherein said MREJ sequence is a type v sequence, wherein SEQ ID NO:65 comprises said MREJ type v sequence.

10. The method of claim 4, wherein said MREJ sequence is a type vi sequence, wherein SEQ ID NO: 69 comprises said MREJ type vi sequence.

11. The method of claim 4 wherein said MREJ sequence is a type vii sequence, wherein SEQ ID NO:70 comprises said MREJ type vii sequence.

12. The method of claim 1, wherein said detecting the presence and/or amount of nuc amplicons in the amplified sample comprises contacting the amplified sample with a nuc probe that anneals under said PCR conditions to said nuc amplicon, wherein said nuc probe comprises a detectable moiety.

13. The method of claim 1, wherein said detecting the presence and/or amount of MREJ amplicons in the amplified sample comprises contacting the amplified sample with an MREJ probe that anneals under said PCR conditions to said MREJ amplicon, wherein said MREJ probe comprises a detectable moiety.

14. The method of claim 4, wherein said MREJ sequence comprises type i, ii, iii, iv, v and vii MREJ sequences.

15. The method of claim 14, wherein said at least one MREJ primer pairs anneal under said PCR conditions to the nucleic acid sequences selected from the group consisting of:
SEQ ID NOs: 99 and 199 or the full complements of SEQ ID NOs: 99 and 199;
SEQ ID NOs: 99 and 201 or the full complements of SEQ ID NOs: 99 and 201;
SEQ ID NOs: 99 and 195 or the full complements of SEQ ID NOs: 99 and 195;
SEQ ID NOs: 99 and 155 or the full complements of SEQ ID NOs: 99 and 155; and
SEQ ID NOs: 99 and 163 or the full complements of SEQ ID NOs: 99 and 163.

16. The method of claim 1, wherein said first and second nuc primers comprise oligonucleotides that anneal under said PCR conditions to at least 11consecutive nucleotides of sequences selected from the group consisting of:
SEQ ID NOs: 1 and 6, or the full complements of SEQ ID NOs: 1 and 6;
SEQ ID NOs: 2 and 5, or the full complements of SEQ ID NOs: 2 and 5;
SEQ ID NOs: 2 and 6, or the full complements of SEQ ID NOs: 2 and 6;
SEQ ID NOs: 3 and 7, or the full complements of SEQ ID NOs: 3 and 7;
SEQ ID NOs: 4 and 7, or the full complements of SEQ ID NOs: 4 and 7; and
SEQ ID NOs: 4 and 8, or the full complements of SEQ ID NOs: 4 and 8.

17. The method of claim 16, wherein said nuc primer pair comprises a first primer that anneals under said PCR conditions to SEQ ID NO: 1, or the complement of SEQ ID NO: 1 and a second primer that anneals under said PCR conditions to SEQ ID NO: 6 or the complement of SEQ ID NO: 6.

18. The method of claim 17, further comprising providing a probe that anneals under said PCR conditions to a sequence selected from the group consisting of SEQ ID NO: 9, SEQ ID NO: 10, the full complement of SEQ ID NO: 9, and the full complement of SEQ ID NO: 10.

19. The method of claim 16, wherein said nuc primer pair comprises a first primer that anneals under said PCR conditions to SEQ ID NO: 3 or the full complement of SEQ ID NO: 3, and a second primer that anneals under said PCR conditions to SEQ ID NO: 8 or the full complement of SEQ ID NO: 8.

20. The method of claim 19, further comprising providing a probe that anneals under said PCR conditions to a sequence selected from the group consisting of SEQ ID NO: 11, SEQ ID NO: 12, the full complement of SEQ ID NO.: 11, and the full complement of SEQ ID NO: 12.

21. The method of claim 13, wherein said MREJ probe comprises an oligonucleotide that anneals under said PCR conditions to at least 11 consecutive nucleotides of a sequence selected from the group consisting of: SEQ ID NO:126, 128, 130, 131, 204, the full complement of SEQ ID NO: 126, the full complement of SEQ ID NO: 128, the full complement of SEQ ID NO: 130, the full complement of SEQ ID NO: 131, and the full complement of SEQ ID NO: 204.

* * * * *

UNITED STATES PATENT AND TRADEMARK OFFICE
CERTIFICATE OF CORRECTION

| | | |
|---|---|---|
| PATENT NO. | : 8,518,646 B2 | Page 1 of 1 |
| APPLICATION NO. | : 11/959337 | |
| DATED | : August 27, 2013 | |
| INVENTOR(S) | : Jean et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1255 days.

Signed and Sealed this
Twenty-first Day of April, 2015

Michelle K. Lee
*Director of the United States Patent and Trademark Office*